US011471460B2

(12) United States Patent
DePamphilis et al.

(10) Patent No.: US 11,471,460 B2
(45) Date of Patent: Oct. 18, 2022

(54) AUTOPHAGY MODULATORS FOR USE IN TREATING CANCER

(71) Applicant: The United States of America, as represented by the Secretary, Department of Health and Human Services, Bethesda, MD (US)

(72) Inventors: Melvin L. DePamphilis, Olney, MD (US); Gaurav Sharma, New Delhi (IN); Juan Jose Marugan, Gaithersburg, MD (US); Marc Ferrer, Potomac, MD (US); Ajit Roy, Rockville, MD (US)

(73) Assignee: The United States of Americans represented by the Secretary, Department of Health and Human Services, Bethesda, MD (US)

( * ) Notice: Subject to any disclaimer, the term of this patent is extended or adjusted under 35 U.S.C. 154(b) by 179 days.

(21) Appl. No.: 16/883,046

(22) Filed: May 26, 2020

(65) Prior Publication Data

US 2020/0369649 A1   Nov. 26, 2020

Related U.S. Application Data

(63) Continuation-in-part of application No. PCT/US2018/062866, filed on Nov. 28, 2018.

(60) Provisional application No. 62/593,579, filed on Dec. 1, 2017.

(51) Int. Cl.
| | |
|---|---|
| *A61K 31/53* | (2006.01) |
| *A61P 35/00* | (2006.01) |
| *A61K 31/506* | (2006.01) |
| *C07D 239/50* | (2006.01) |
| *C07D 251/54* | (2006.01) |
| *C07D 403/12* | (2006.01) |

(52) U.S. Cl.
CPC .......... *A61K 31/53* (2013.01); *A61K 31/506* (2013.01); *A61P 35/00* (2018.01); *C07D 239/50* (2013.01); *C07D 251/54* (2013.01); *C07D 403/12* (2013.01)

(58) Field of Classification Search
CPC .. C07D 239/50; C07D 251/54; C07D 403/12; A61K 31/53; A61K 31/506; A61P 35/00
See application file for complete search history.

(56) References Cited

FOREIGN PATENT DOCUMENTS

| CN | 102659765 A | 9/2012 |
| WO | 2015/124120 A1 | 8/2015 |
| WO | 2016/204988 A1 | 12/2016 |

OTHER PUBLICATIONS

Bissig et al., "PIKfyve activity regulates reformation of terminal storage lysosomes from endolysosomes," *Traffic*, 18:747-757 (2017).
Cai et al., "PIKfyve, a class III PI-kinase, is the target of the small molecular IL12/23 inhibitor apilimod and a new player in toll-like receptor signaling," *Chem. Biol.*, 20(7):912-921 (2013).
Chen et al., "Identification of Novel Vacuolin-1 Analogues as Autophagy Inhibitors by Virtual Drug Screening and Chemical Synthesis," *Molecules*, 22:891 (2017).
Compton et al., "Active vacuolar H+ ATPase and functional cycle of Rab5 are required for the vacuolation defect triggered by PtdIns(3,5)P$_2$ loss under PIKfyve or Vps34 deficiency," *American Journal of Physiology Cell Physiology*, 311(3):C366-C377 (2016).
Davidson et al., "Critical Functions of the Lysosome in Cancer Biology," *Annu. Rev. Pharmacol. Toxicol.*, 57:481-507 (2017).
Davis et al., "Comprehensive analysis of kinase inhibitor selectivity," *Nat. Biotechnol.*, 29(11):1046-1051 (2011).
De Lartigue et al., "PIKfyve Regulation of Endosome-Linked Pathways," *Traffic*, 10:883-893 (2002).
European Patent Office, International Search Report in International Patent Application No. PCT/US2018/062866, dated Mar. 14, 2019 (5 pp.).
European Patent Office, Written Opinion in International Patent Application No. PCT/US2018/062866, dated Mar. 14, 2019 (10 pp.).
Gayle et al., "Identification of apilimod as a first-in-class PIKfyve kinase inhibitor for treatment of B-cell non-Hodgkin lymphoma," *Blood*, 129(13):1768-1778 (2017).
Goodall et al., "Development of potent autophagy inhibitors that sensitize oncogenic BRAF V600E mutant melanoma tumor cells to vemurafenib," *Autophagy*, 10(6):1106-1136 (2014).

(Continued)

*Primary Examiner* — Deepak R Rao
(74) *Attorney, Agent, or Firm* — Leydig Voit and Mayer, Ltd.

(57) ABSTRACT

Disclosed is method for treating cancer in a mammal, comprising administering to a mammal in need thereof a compound of the formula:

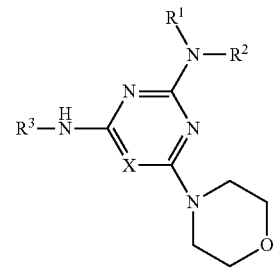

wherein $R^1$, $R^2$, and $R^3$ are as defined herein, wherein the cancer is an autophagy-dependent cancer, in an amount sufficient to induce autophagy in the cell and cause the death of cancer cells. Also disclosed is a method for selectively killing cancer cells in a patient afflicted with cancer, comprising administering to the mammal, wherein the cancer cells are autophagy-dependent cancer cells, in an amount sufficient to induce autophagy in the cells and cause the death of the cancer cells.

8 Claims, 32 Drawing Sheets

(56) References Cited

OTHER PUBLICATIONS

Jefferies et al., "A selective PIKfyve inhibitor blocks PtdIns(3,5)$P_2$ production and disrupts endomembrane transport and retroviral budding," *EMBO Reports*, 9(2):164-170 (2008).
Lee et al., "High-throughput screening for genes that prevent excess DNA replication in human cells and for molecules that inhibit them," *Methods*, 57(2):234-248 (2012).
Marino et al., "Autophagy is a Protective Mechanism for Human Melanoma Cells under Acidic Stress," *The Journal of Biological Chemistry*, 287(36):30664-30676 (2012).
Martin et al., "Inhibition of PIKfyve by YM-201636 Dysregulates Autophagy and Leads to Apoptosis-Independent Neuronal Cell Death," *PLoS One*, 8(3):e60152 (2013).
Mulcahy Levy et al., "Autophagy inhibition overcomes multiple mechanisms of resistance to BRAF inhibition in brain tumors," *eLife*, 6:019671 (2017).
Pellegrini et al., "Acidic extracellular pH neutralizes the autophagy-inhibiting activity of chloroquine," *Autophagy*, 10(4):562-571 (2014).
Piao et al., "Targeting the lysosome in cancer," *Ann. NY Acad. Sci.*, 1371(1):45-54 (2016).
Rebecca et al., "A unified approach to targeting the lysosome's degradative and growth signaling roles," *Cancer Discov.*, 7(1):1266-1283 (2017).
Sano et al., "Vacuolin-1 inhibits autophagy by impairing lysosomal maturation via PIKfyve inhibition," *FEBS Letters*, 590:1576-1585 (2016).
Zheng et al., "Synthesis and antitumor evaluation of a novel series of triaminotriazine derivatives," *Bioorganic & Medicinal Chemistry*, 15:1815-1827 (2007).
Zhu et al., "An Image Based, High-Throughput, Screening Assay for Molecules That Induce Excess DNA Replication in Human Cancer Cells," *Mol. Cancer Res.*, 9(3):294-310 (2011).

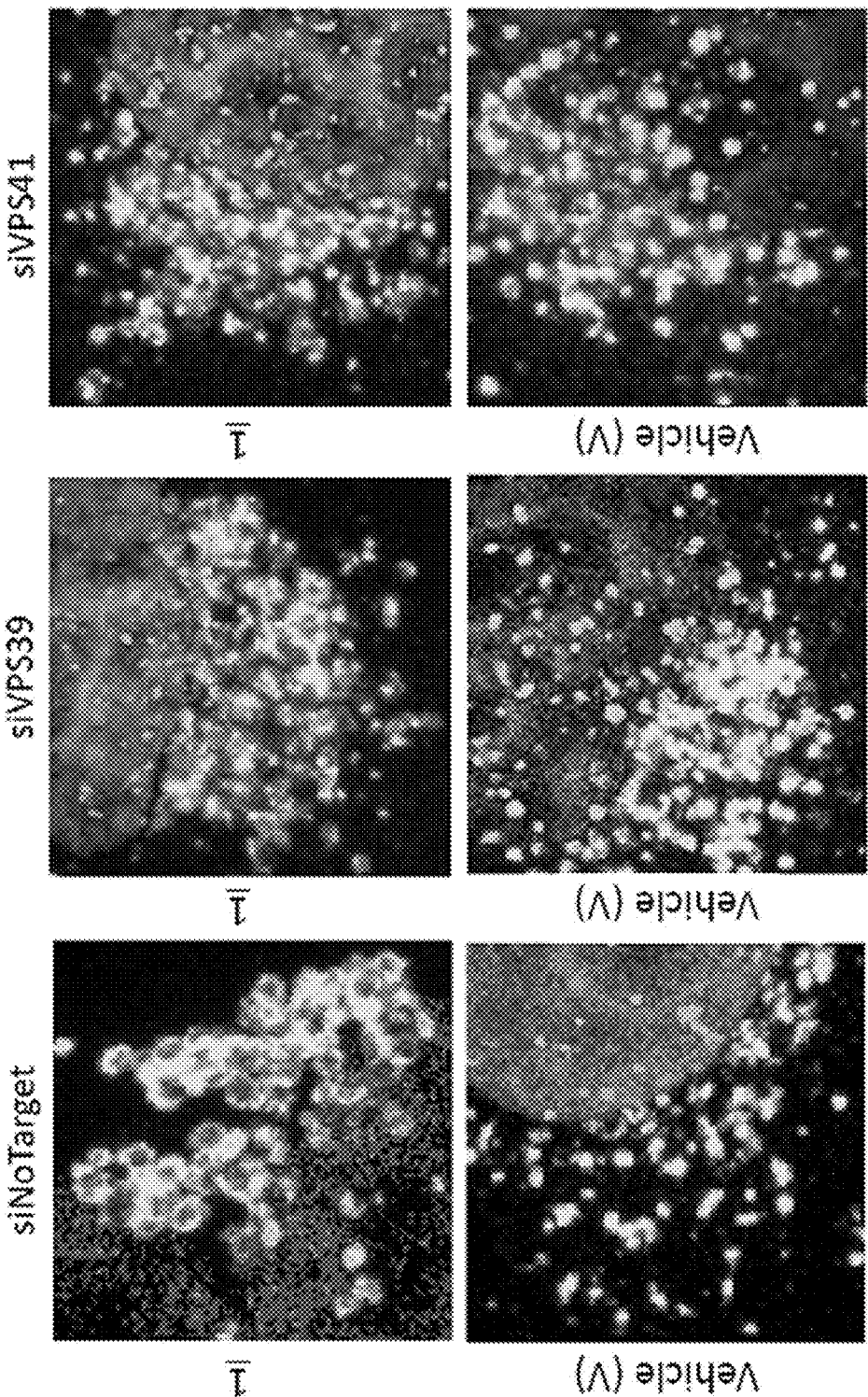

Ratio Metric Analysis of Lysosomal pH (Oregon Green Dextran)
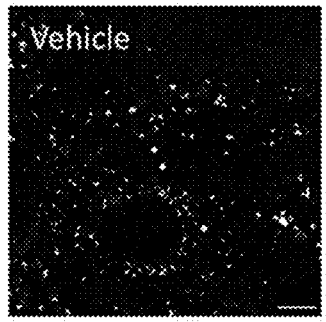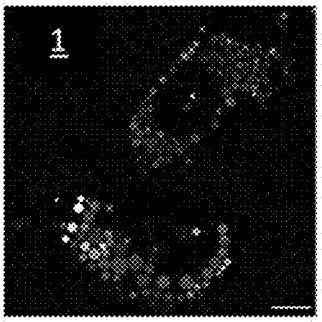
| Treatment | pH ± SEM |
|---|---|
| Vehicle | 5.3 ± 0.05 |
| Compound 1 | 5.0 ± 0.04 |
| NH₄Cl | 5.7 ± 0.05 |
FIG. 8A
LysoTracker staining
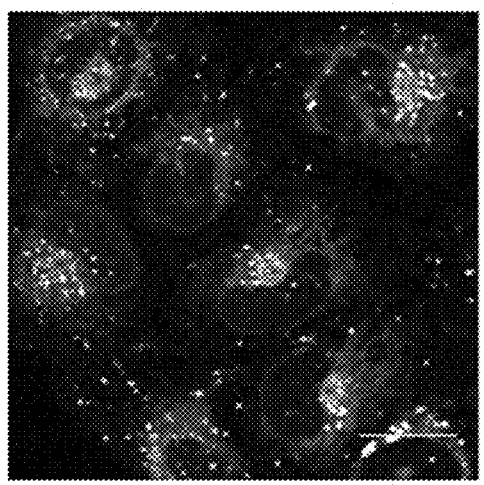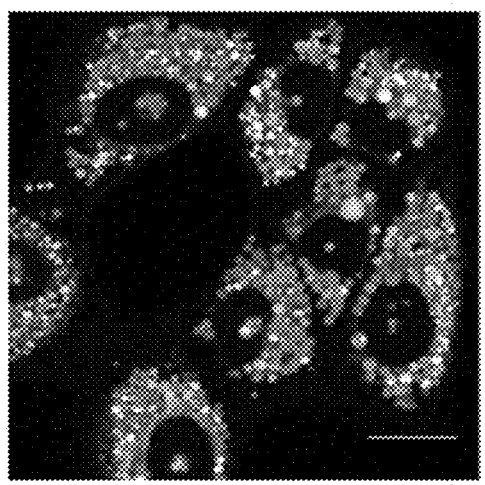
FIG. 8B

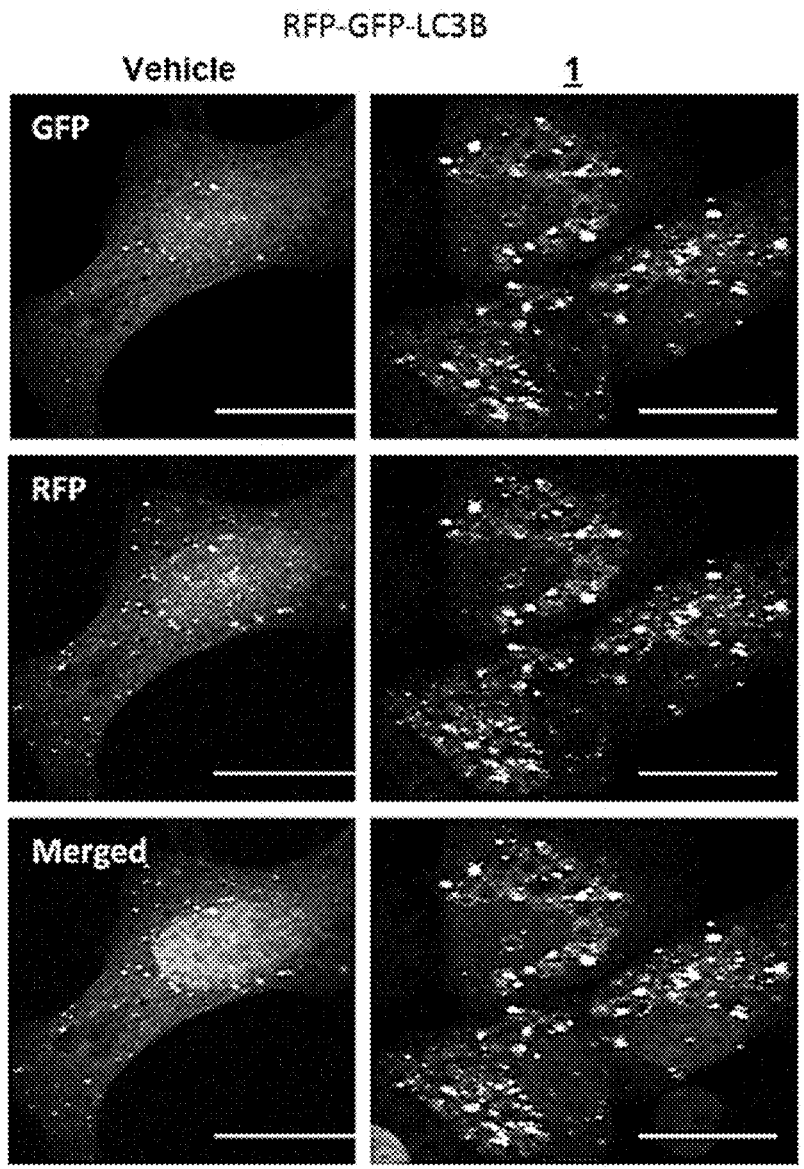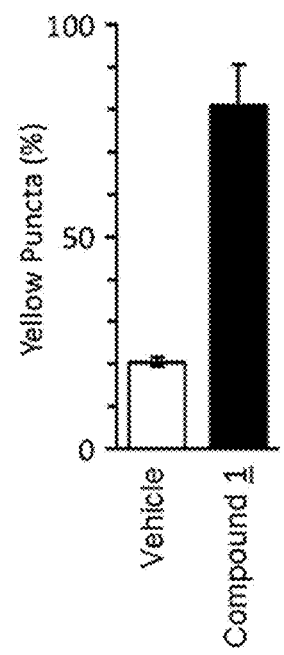
FIG. 12A  FIG. 12B

| Compound | Kd (nM) ± range | | | PIP4K2C /PIKfyve |
|---|---|---|---|---|
| | PIKfyve | PIP4K2C | MTOR | |
| 1 | 0.93 ±0.03 | 340 ±75 | 7200 ±750 | 366 |
| 4 | 1.6 ±0.2 | 24000 ±3000 | 25000 ±6500 | 15000 |
| 5 | 4.8 ±0.05 | 9200 ±100 | 10000 ±750 | 1917 |
| 3 | 11 ±0 | 990 ±225 | 60000 ±0 | 90 |
| 2 | 16 ±1 | 20000 ±0 | >60000 ±0 | 1250 |

| Human Cell Lines | Compounds Effective Concentration (EC) and Inhibitory Concentration (IC₅₀) in µM ||||||||
|---|---|---|---|---|---|---|---|---|
| | Vacuolization (EC) | Proliferation (IC₅₀) ||| Viability (IC₅₀) ||| Ratio HCQ, CQ / 1 |
| | 1 | HCQ | CQ | 1 | HCQ | CQ | 1 | |
| Melanoma A-375 | ≤0.1 | 0.01-0.1 | 1-10 | 1-10 | 0.01 | 3.2 | 1.8 | 180-320 |
| Melanoma M321 | ≤0.1 | 0.01-0.1 | 1-10 | 1-10 | 0.40 | 3.89 | 4.2 | 105-97 |
| Colorectal carcinoma SW480 | ≤0.1 | 0.1-0.5 | >10 | >10 | 0.31 | >10 | >10 | >32 |
| Colorectal carcinoma HCT116 | ≤0.1 | 0.1-0.5 | 1-10 | 1-10 | 0.37 | 9.5 | 9.5 | 26 |
| Osteosarcoma U2OS | ≤0.1 | 0.1-0.5 | 1-10 | 1-10 | 0.34 | 5.7 | 5.0 | 15-17 |
| Melanoma MEWO | ≤0.1 | 1-10 | 1-10 | 1-10 | 1.5 | 7.5 | 5 | 3-5 |
| Colon carcinoma RKO | ≤0.1 | 0.1-0.5 | 1-10 | 1-10 | 7.9 | >10 | 10 | ~2 |
| Melanoma M229 | ≤0.1 | 1-10 | 1-10 | 1-10 | 2.9 | >10 | 3.8 | 1.5-3.5 |
| Melanoma G-361 | ≤0.1 | 1-10 | 1-10 | 1-10 | ? | ? | ? | 1 |
| Breast Adenocarcinoma MDA-MB-231 | ≤0.1 | 1-10 | 1-10 | 1-10 | >10 | >10 | >10 | 1 |
| Breast Adenocarcinoma MCF7 | ≤0.1 | 1-10 | 1-10 | 1-10 | >10 | >10 | >10 | 1 |
| Embryonic Kidney 293T | ≤0.1 | >10 | >10 | >10 | >10 | >10 | >10 | 1 |
| Foreskin Fibroblasts HFF | ≤0.1 | >10 | >10 | >10 | >10 | >10 | >10 | 1 |

FIG. 18

AUTOPHAGY MODULATORS FOR USE IN TREATING CANCER

CROSS-REFERENCE TO A RELATED APPLICATION

This patent application is a continuation-in-part of International Application No. PCT/US2018/062866, filed Nov. 28, 2018, which claims the benefit of U.S. Provisional Patent Application No. 62/593,579, filed Dec. 1, 2017, the disclosures of which are incorporated by reference for all purposes.

STATEMENT REGARDING FEDERALLY SPONSORED RESEARCH AND DEVELOPMENT

This invention was made with Government support under project number Z01HD000506 AND Z01HD000507 by the National Institutes of Health, National Institute for Child Health and Human Development and the National Center for Advancing Translational Sciences. The Government has certain rights in the invention.

BACKGROUND OF THE INVENTION

Autophagy is a ubiquitous cytoplasmic process for collecting and degrading damaged or redundant cellular components in response to demands for energy and nutrients. Since cell growth and proliferation of cancers frequently depend upon autophagy for survival, selective killing of cancer cells might be accomplished through inhibition of autophagy (Cantwell-Dorris, E. R. et al., *Mol Cancer Ther* 10, 385-394 (2011); Guo, J. Y. et al., *Genes Dev* 25, 460-470 (2011); Strohecker, A. M. et al., *Cancer Discov* 4, 766-772 (2014)). Deletion of the essential autophagy genes in mouse models for $KRASG12^D$- and BRAFV600-Edriven cancers results in arrest of tumor cell proliferation, cell death, progression to more benign disease, and extends lifespan (Xie et al., 2015). Similar results have been seen in humans by inhibiting autophagy with chloroquine (Levy, J. M. et al., *Cancer Discov* 4, 773-780 (2014); Mulcahy Levy, J. M. et al., *Autophagy* 10, 2077-2078 (2014); Mulcahy Levy, J. M. et al., *Elife* 6 (2017)), suggesting $BRAF^{V600}E$ tumor cells are especially dependent on autophagy compared to their BRAF counterparts. In fact, the $BRAF^{V600E}$ mutation has been reported in breast cancer (13%), malignant melanoma (40%-70%), colorectal carcinoma (5%-22%) thyroid papillary carcinoma (36%-53%), glioma (11%), ovarian serous carcinoma (30%), lung adenocarcinoma (4%) and hairy cell leukemia (100%) (Jung, Y. Y. et al., *Int J Clin Exp Pathol* 9, 1545-1556 (2016)). In addition, inhibition of autophagy in conjunction with targeted cancer chemotherapy can increase the efficacy of the chemotherapy (Mulcahy Levy et al. (2017); Vogl, D. T. et al., *Autophagy* 10, 1380-1390 (2014)). Therefore, drugs that can selectively arrest and kill autophagy-dependent cells with little or no harm to normal cells will have wide application in cancer therapy.

Current efforts to utilize autophagy inhibition in cancer chemotherapy have relied on chloroquine and its derivatives (Compton, L. M. et al., *Am J Physiol Cell Physiol* 311, C366-377 (2016); Levy et al. (2014); Mulcahy Levy et al. (2014); Mulcahy Levy et al. (2017); Mushtaque, M. et al., *Eur J Med Chem* 90, 280-295 (2015); Rangwala, R. et al., *Autophagy* 10, 1391-140 (2014); Vogl et al. (2014)), and new chloroquine derivatives are in development (Goodall, M. L. et al., *Autophagy* 10, 1120-1136 (2014)). These drugs diffuse into acidic compartments where they are protonated and trapped, thereby decreasing lysosomal acidity and rendering pH dependent lysosomal hydrolases nonfunctional Consequently, autophagy-mediated cell survival is impaired, and tumor cells treated with chloroquine are less able to withstand therapeutic treatments and are therefore sensitized to therapy (Amaravadi, R. K. et al., *J Clin Invest* 117, 326-336 (2007); Ma, X. H. et al., Clin Cancer Res 17, 3478-348 (2011); Yang, S. et al., Genes Dev 25, 717-729 (2011)).

Cancer cells, however, can survive acidic stress by upregulating autophagy, suggesting that interrupting autophagy with chloroquine might not be achieved in an acidic tumor microenvironment. Therefore, therapeutic strategies that disrupt multiple events in lysosome homeostasis are required in order to suppress nutrient recovery and energy production (Pellegrini P et al., *Autophagy* 2014; 10: 562-71; Marino ML et al., *J. Biol. Chem.* 2012; 287:30664-76; Piao S, et al., *Ann N Y Acad Sci* 2016; 1371: 45-54; Davidson S M et al., *Annu Rev Pharmacol Toxicol* 2017; 57: 481-507; Rebecca V W et al., *Cancer Discov* 2017; 7: 1266-83). The foregoing shows that there exists an unmet need for treating cancer, particularly by selectively blocking autophagy in autophagy-dependent cancer cells.

BRIEF SUMMARY OF THE INVENTION

The invention provides a method for treating cancer in a mammal, comprising administering to a mammal in need thereof a compound or salt of the formula:

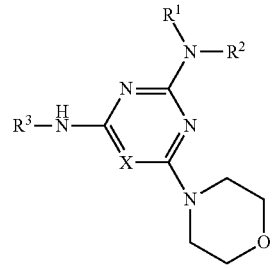

wherein $R^1$ and $R^2$ are independently H, optionally substituted $C_1$-$C_6$ alkyl, or optionally substituted $C_6$-$C_{10}$ aryl, or wherein $R^1$ and $R^2$, taken together with the N to which they are attached, form a 5- or 6-membered heterocyclyl ring, $R^3$ is optionally substituted $C_6$-$C_{10}$ aryl or a group of the formula: $R^4CH=N-$ wherein $R^4$ is $C_6$-$C_{10}$ aryl, heteroaryl, or fused bicyclic heteroaryl, X is CH or N, or a tautomer thereof, or a pharmaceutically acceptable salt thereof, wherein the cancer is an autophagy-dependent cancer, in an amount sufficient to inhibit autophagy in the cell and cause the death of cancer cells.

The invention also provides a method for selectively killing cancer cells in a patient afflicted with cancer, comprising administering to the mammal a compound or salt of the formula:

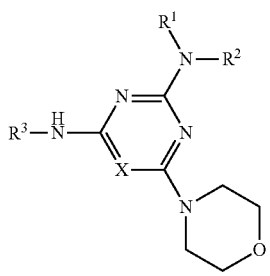

wherein $R^1$ and $R^2$ are independently H, optionally substituted $C_1$-$C_6$ alkyl, or optionally substituted $C_6$-$C_{10}$ aryl, or wherein $R^1$ and $R^2$, taken together with the N to which they are attached, form a 5- or 6-membered heterocyclyl ring, $R^3$ is optionally substituted $C_6$-$C_{10}$ aryl or a group of the formula: $R^4$CH=N— wherein $R^4$ is $C_6$-$C_{10}$ aryl, heteroaryl, or fused bicyclic heteroaryl, X is CH or N, or a tautomer thereof, or a pharmaceutically acceptable salt thereof, wherein the cancer cells are autophagy-dependent cancer cells, in an amount sufficient to inhibit autophagy in the cells and cause the death of the cancer cells.

The compounds of the invention have one or more of the following advantageous properties:

I. Compounds of this invention rapidly disrupt three events in lysosome homeostasis in a manner that is compound dependent, concentration dependent, time dependent and reversible.
  A. They inhibit lysosome fission via tubulation without preventing homotypic lysosome fusion, thereby inducing accumulation of enlarged lysosomes, and preventing lysosome turnover.
  B. They impaired trafficking of molecules into lysosomes without altering lysosomal acidity, thereby disrupting lysosomal function.
  C. They inhibit heterotypic fusion between lysosomes and autophagosomes, thereby blocking autophagic flux.
II. Compounds of this invention bind specifically to the PIKFYVE phosphatidylinositol kinase and inhibit its activity.
III. Compounds of this invention can selectively inhibit the proliferation and reduce the viability of autophagy-dependent human cancer cells under conditions where autophagy-independent human cells continue to proliferate.
  A. Viability of autophagy-dependent human cancer cells is reduced up to 1000-times more than viability of normal human cells.
  B. Autophagy-dependent melanoma cells treated with these compounds form tumors in nude mice at half the rate of untreated cells.
IV. Given the properties outlined above, compounds of this invention are useful in the treatment of autophagy-dependent human cancers either alone or in combination with established anti-cancer therapies.

BRIEF DESCRIPTION OF THE SEVERAL VIEWS OF THE DRAWINGS

FIG. 3A shows microscopic images of U2OS cells expressing LAMP1-RFP that were cultured with 1 µM compound 1 for 40 min, during which time live cell images were collected. Arrows indicate one example of fusion between two lysosomes to produce a larger lysosome. FIG. 3B shows electron microscopic images of thin sections taken at 2 hrs of U2OS cells that were cultured as in panel A. FIG. 3C shows the section indicated in panel B enlarged 4×. Arrows indicate sites of lysosome-to-lysosome fusion.

FIG. 5A-D show that suppression of essential lysosome fusion genes by siRNA prevented lysosome enlargement by the compound 1 family. HeLa cells were transfected for 2-days, two consecutive times, with a pool of no-target siRNAs (FIG. 5A) or siRNAs targeted against the HOPS-specific subunits VPS39 (FIG. 5B) and VPS41 (FIG. 5C). Cells were then incubated for 30 min either with vehicle (V) or with 1 M compound 1. Scale bar is 10 μm. FIG. 5D shows a Western immuno-blot with non-targeting (nt) siRNA as a negative control, and GAPDH protein as an internal loading control. Thus, accumulation of enlarged lysosomes requires the HOPS complex required for homotypic fusion between lysosomes and heterotypic fusion between lysosomes and other organelles.

FIG. 6E shows bar graphs indicating the mean±SD for the lysosomal area in two independent experiments for each image. Thus, accumulation of enlarged lysosomes requires the BORC complex for homotypic fusion between lysosomes and heterotypic fusion between lysosomes and other organelles.

In FIG. 7A, U2OS cells expressing LAMP1-RFP were cultured with 0.1 μM compound 1 for 2 hrs. The cells were then washed twice with phosphate buffered saline before transferring them to fresh culture medium without compound 1 and monitored by live-cell imaging for 1 hour.

In FIG. 7B, one image in every 3 seconds was captured after compound 1 was removed. Images in the top panel begin 13 min and images in the bottom panel begin 33:36 min after compound 1 was removed. They each show a single enlarged lysosome (*) undergoing fission via tubulation. Arrows facilitate the tracking of tubule fate. The size of the lysosome at the beginning and end of each sequence is indicated. Scale bar is 20 μm.

FIG. 8A-C shows that compounds of the invention did not impair lysosomal acidity. FIG. 8A shows confocal microscopic images of human U2OS cells that were pre-loaded with Oregon Green Dextran in preparation for ratiometric analysis of the pH of individual lysosomes. U2OS cells were cultured for 4 hr with vehicle, 1 μM compound 1, or 50 mM ammonium chloride. The results of two independent experiments were averaged together. Data were analyzed by one-way ANOVA (p=0.0005) and Tukey's post-hoc test (p<0.0001). Scale bars indicate 10 μm. The results of three independent experiments were averaged together. FIG. 8B shows confocal microscopic images of U2OS cells were cultured for 4 h in the presence of either vehicle or 1 μM compound 1, and then live cells were stained with LysoTracker Green DND-26, a dye that stains acidic compartments in live cells, but fluoresces over a broad pH range. FIG. 8C shows confocal microscopic images of U2OS cells that were cultured for 4 h in the presence of either vehicle, 1 μM compound 1 or 50 nM bafilomycin A1 (BafA1), and then live cells were stained as indicated according to the manufacturer's instructions and viewed immediately. Cells that had been transfected with LAMP1-RFP expression vector were then stained with LysoSensor Green DND-189, a fluorescent probe that fluoresces only in the acidic compartments of live cells. The absence of green vacuoles confirmed that LysoSensor Green did not accumulate in the enlarged lysosomes. Bars represent 20 μm.

FIG. 10A shows that the phosphatidylethanolamine conjugate (LC3-II) of MAP1LC3A protein (LC3-I), and the SQSTM1/Ubiquitin-Binding Protein p62 (p62) are two critical autophagosome markers. FIG. 10B shows Western immunoblots of U2OS cells that were seeded in 6-well plates ($0.7×10^5$/well) and 24 hrs later was added the indicated compound to give the indicated concentration. Cells were cultured for 4 hrs before total cell extracts were subjected to Western immuno-blotting for LC3, p62 and β-actin. Blot was developed with film. FIG. 10Bi shows the ratios of LC3-II/actin and p62/actin in FIG. 10B subtracted from the compound 1 treated samples, and the results were normalized to the maximum ratio and then plotted. (C) U2OS cells were cultured for the times indicated in the presence of 1.2 µM compound 1 to produce 80% of the maximum observed in FIG. 10A. Total cell extracts were assayed at the times indicated. FIG. 10Ci shows the ratios of LC3-II/actin and p62/actin in FIG. 10C plotted as in FIG. 10Bi. All blots were stained with Ponceau S to visualize the β-actin loading control.

FIG. 11A shows U2OS cells were cultured in the presence of either vehicle or 1 µM compound 1 for 4 hrs, and then endogenous autophagosomes were identified by staining cells with fluorescent tagged anti-LC3 antibody. FIG. 11B shows U2OS cells were transfected with a baculovirus expressing GFP-LC3 and then culturing them overnight before addition of either vehicle or 1 µM compound 1. Fluorescence was analyzed by confocal microscopy 4 hrs later. FIG. 11Ai, 11Bi shows the number of LC3 and GFP-LC3 labeled puncta per cell from FIGS. 11A and 11B, respectively. LC3 puncta were quantified from 50 cells from each of three independent experiments (mean±SEM; Student's t-test, p<0.0001). Both LC3 and GFP-LC3 labeled puncta increased 6 to 8-fold in the presence of compound 1.

FIG. 12A-B shows that compounds of the invention induced accumulation of autophagosomes that were neutral pH, and therefore had not fused with acidic lysosomes. Confocal microscopic images are shown in FIG. 12A of U2OS cells expressing a modified tandem sensor RFP-GFP-tagged LC3B protein in which the green signal from a mutated GFP was suppressed in an acidic environment, with little or no effect on the red signal from RFP. Thus, autophagosomes with neutral pH would fluoresce yellow, whereas autolysosomes with acidic pH would fluoresce red. These cells were treated with either vehicle or 1 µM compound 1 for 4 hrs. The fraction of yellow puncta, representing autophagosomes with a neutral pH, was quantified in 50 cells from each of three independent experiments (mean±SEM; Student's t-test, p<0.0001) as shown in FIG. 12B. The fraction of yellow puncta increased 4-fold in the presence of compound 1 (right side graph).

FIG. 14A shows the binding affinity of 10 µM compound 1 as profiled against 468 human kinases by DiscoverX KINOMEscan (San Diego, Calif.). Compounds that bind to the active site of a protein kinase prevented the protein from binding to an immobilized active site ligand, thereby reducing the amount of protein captured on a solid support. Each kinase was tagged with a unique DNA sequence that allowed the amount of protein bound to the solid support to be quantified by PCR. The top three targets for compound 1 were PIKFYVE, PIP4K2C and MTOR. FIG. 14B shows the mean equilibrium dissociation constant (Kd) for compound 1 with PIKFYVE, PIP4K2C and MTOR as determined from two independent titration curves. Dissociation constants (Kd) were determined from the amount of kinase captured on the solid support as a function of the test compound concentration (nM) on a $\log_{10}$ scale. Mean Kd values (±range) are given for each compound. The ratio of PIP4K2C to PIKFYVE indicates the relative specificity for these two kinases.

FIG. 16A shows photographs of cells after two days to reveal cytoplasmic vacuolization. FIG. 16B shows photographs taken after seven days after the indicated compound was added and adherent cells were stained with crystal violet to reveal cell proliferation. FIG. 16C shows total cellular ATP using the CellTiter-Glo luminescent cell viability assay. To reveal viability, cells were seeded into 96-well plates (1,000 cells/well), and the indicated compound was added the following day. Cells were cultured for four days before quantification of total cellular ATP. FIG. 16D shows total live cells in each well plotted as a percentage of the number of live cells in the vehicle control. In separate 12-well plates, attached cells were collected by trypsinization, combined with unattached cells, and stained with trypan blue to identify dead cells. Vehicle was plotted as 0.001 µM compound in order to apply a logarithmic scale. Data were plotted as the mean±SEM for three independent experiments.

FIG. 17A shows photographs of cells after two days to reveal cytoplasmic vacuolization. FIG. 17B shows photographs taken after seven days after the indicated compound was added and adherent cells were stained with crystal violet to reveal cell proliferation. FIG. 17C shows total cellular ATP using the CellTiter-Glo luminescent cell viability assay. Concentration of each compound in the plate assay is indicated below the compound 1 plate. Nevertheless, HFF cells were as sensitive to cytoplasmic vacuolization by compound 1 as were melanoma A375 cells.

FIG. 18 summarizes results from 13 human cell lines. All cells were seeded at the same cell density in a rich culture medium and assayed under identical conditions. Compound 1 efficacy is the ratio of cell viability with compound 1 to cell viability with chloroquine derivatives. Autophagy-dependent cells (those sensitive to chloroquine derivatives) were up to 320-times more sensitive to compounds of the invention than autophagy-independent cells (those not sensitive to chloroquine derivatives).

FIG. 19A shows phase contrast images of melanoma A375 cells that were cultured for 8 hours with either vehicle or 10 µM compound 1. Viability was quantified by trypan blue dye exclusion method. The images confirmed the presence of cytoplasmic vacuolization occurred only in the compound 1 treated cells. FIG. 19B shows images of nude mice and tumors excised therefrom that were inoculated subcutaneously with 1×10$^6$ cells in 100 µL of ice cold DMEM and 50% Matrigel. The left flank received cells pretreated with vehicle and the right flank received cells pretreated with compound 1. At 27 days later, mice were photographed, and tumors excised. FIG. 19C shows measurements of tumor volume and mouse weight. FIG. 19D revealed that compound 1 pretreatment of cancer cells inhibited their ability to form a tumor with no ill effects on mice. Error bars indicate the SEM for 5 tumors.

FIG. 20B-C shows the expansion of preformed tumors was inhibited by compound 1 in a dose dependent manner with no exhibited ill effects to the mice (FIG. 20C). Error bars indicate the SEM for 6 tumors.

DETAILED DESCRIPTION OF THE INVENTION

Figures 1A, 1B:
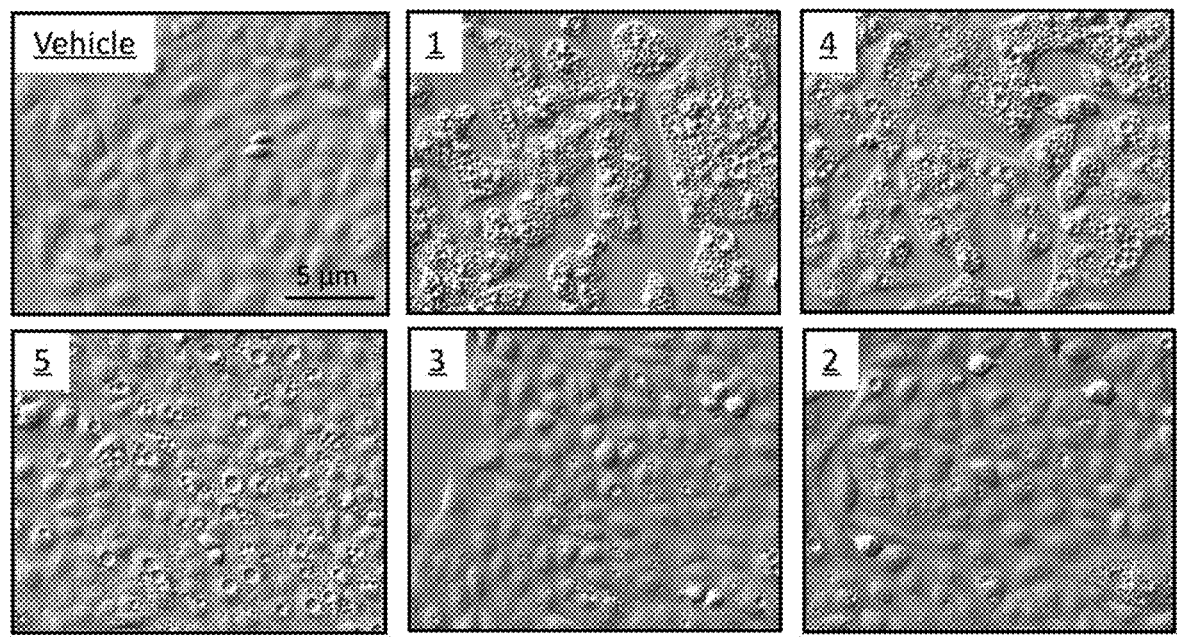
FIG. 1A shows differential interference microscopic images of osteosarcoma U2OS cells cultured for 24 hrs with 1 µM of the indicated compound. Vehicle is the concentration of DMSO that was introduced by addition of compounds. Fewer than 1% of the cells treated with vehicle exhibited a vacuole. These results demonstrate that the compounds of the invention induced accumulation of cytoplasmic vacuoles.
FIG. 1B shows that compounds of the invention effectively induced vacuoles (enlarged lysosomes) in U2OS cells within 4 hrs at the effective concentration (EC), induced accumulation of LC3-II (autophagosome marker) within 4 to 8 hrs at the half maximal effective concentration ($EC_{50}$), suppressed cell proliferation within 3 days at the half maximal inhibitory concentration ($IC_{50}$), and reduced cellular ATP levels (viability) within 4 days ($IC_{50}$). These results reveal that induction of vacuoles (enlarged lysosomes) and autophagosomes in osteosarcoma U2OS cells are accompanied by inhibition of cell proliferation and viability. These effects are dependent on the compound selected, its concentration and the length of time cells are exposed to the compound.

In accordance with an embodiment, the invention provides a method for treating cancer in a mammal, comprising administering to a mammal in need thereof a compound of the formula:

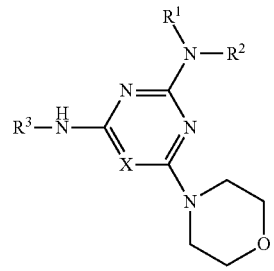

wherein $R^1$ and $R^2$ are independently H, optionally substituted $C_1$-$C_6$ alkyl, or optionally substituted $C_6$-$C_{10}$ aryl, or wherein $R^1$ and $R^2$, taken together with the N to which they are attached, form a 5- or 6-membered heterocyclyl ring, $R^3$ is optionally substituted $C_6$-$C_{10}$ aryl or a group of the formula: $R^4$CH=N— wherein $R^4$ is $C_6$-$C_{10}$ aryl, heteroaryl, or fused bicyclic heteroaryl, X is CH or N, or a tautomer thereof, or a pharmaceutically acceptable salt thereof, wherein the cancer is an autophagy-dependent cancer, in an amount sufficient to inhibit autophagy in the cell and cause the death of cancer cells.

In accordance with an embodiment, X is N.

In accordance with certain embodiments, $R^1$ and $R^2$, taken together with the N to which they are attached, form morpholinyl, and $R^3$ is optionally substituted $C_6$-$C_{10}$ aryl.

In accordance with specific embodiments, the compound is:

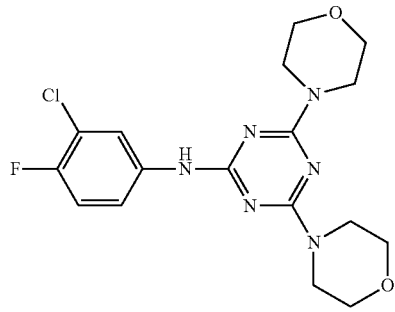

2 or

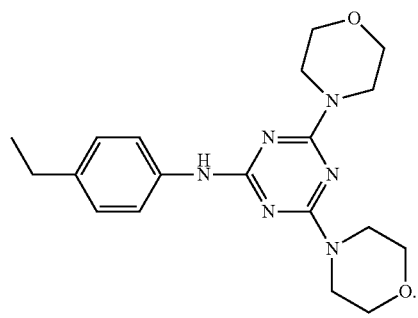

3

In accordance with certain embodiments, R³ is R⁴CH═N— or a tautomer thereof such as R⁴═CH—NH—, R¹ is H, and R² is optionally substituted $C_6$-$C_{10}$ aryl.

In accordance with a specific embodiment, the compound is:

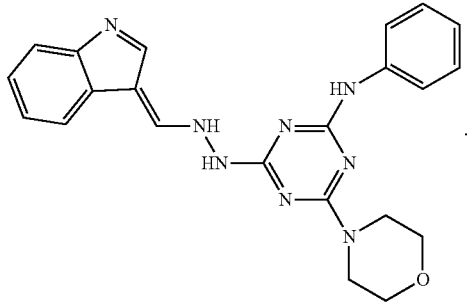

1

In accordance with an embodiment, X is CH.

In accordance with certain embodiments, R³ is R⁴CH═N— and wherein R¹ and R², taken together with the N to which they are attached, form morpholinyl.

In accordance with specific embodiments, the compound is:

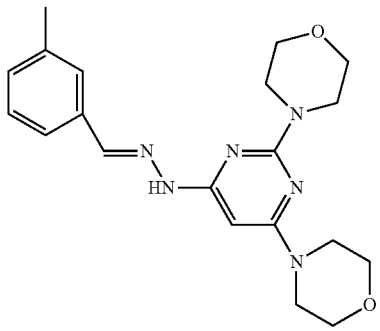

4 or

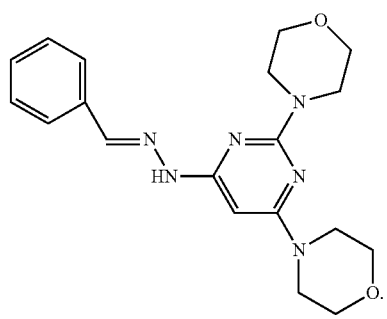

5

In certain embodiments, the cancer is a malignant, metastatic cancer.

In certain of these embodiments, the cancer is breast cancer, malignant melanoma, colorectal carcinoma, thyroid papillary carcinoma, glioma, ovarian serous carcinoma, lung adenocarcinoma, or hairy cell leukemia.

In certain preferred embodiments, the cancer comprises cells having a BRAF$^{V600E}$ mutation.

In another embodiment, the invention provides a method of selectively killing cancer cells in a patient afflicted with cancer, comprising administering to the mammal a compound of the formula:

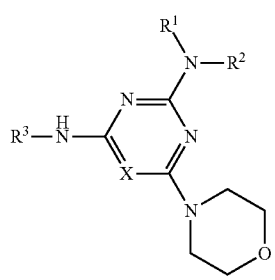

wherein R¹ and R² are independently H, optionally substituted $C_1$-$C_6$ alkyl, or optionally substituted $C_6$-$C_{10}$ aryl, or wherein R¹ and R², taken together with the N to which they are attached, form a 5- or 6-membered heterocyclyl ring, R³ is optionally substituted $C_6$-$C_{10}$ aryl or a group of the formula: R⁴CH═N— wherein R⁴ is $C_6$-$C_{10}$ aryl, heteroaryl, or fused bicyclic heteroaryl, X is CH or N,
or a tautomer thereof,
or a pharmaceutically acceptable salt thereof, wherein the cancer cells are autophagy-dependent cancer cells, in an amount sufficient to inhibit autophagy in the cells and cause the death of the cancer cells.

In certain embodiments, the cancer cells are breast cancer cells, malignant melanoma cells, colorectal carcinoma cells, thyroid papillary carcinoma cells, glioma cells, ovarian serous carcinoma cells, lung adenocarcinoma cells, or hairy cell leukemia cells.

In certain preferred embodiments, the cancer cells comprise cells having a $BRAF^{V600E}$ mutation.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2 π electrons, according to Hickel's Rule.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be an aliphatic heterocyclyl group. The heterocyclyl group can be a monocyclic heterocyclyl group or a bicyclic heterocyclyl group. Suitable bicyclic heterocyclyl groups include monocylic heterocyclyl rings fused to a $C_6$-$C_{10}$ aryl ring, for example, dihydrobenzofuran or 1,2,3,4-tetrahydroquinoline, 1,2,3,4-tetrahydroisoquinoline, or indoline. Non-limiting examples of suitable heterocyclyl groups include tetrahydrofuranyl, tetrahydropyranyl, tetrahydrothiopheneyl, pyrrolidinyl, piperidinyl, and morpholinyl. The heterocyclyl group is optionally substituted with 1, 2, 3, 4, or 5 substituents as recited herein such as with alkyl groups such as methyl groups, ethyl groups, and the like, or with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl group.

The term "heteroaryl" refers to a monocyclic or bicyclic 5- or 6-membered ring system as described herein, wherein the heteroaryl group is unsaturated and satisfies Hickel's rule. Non-limiting examples of suitable heteroaryl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, pyridazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heterocyclyl or heteroaryl group is optionally substituted with 1, 2, 3, 4, or 5 substituents as recited herein such as with alkyl groups such as methyl groups, ethyl groups, and the like, halo groups such as chloro, or hydroxyl groups, with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl or heteroaryl group, or with benzo groups, to form a group of, for example, benzofuran or indolyl.

The phrase "pharmaceutically acceptable salt" is intended to include non-toxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, such as those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (such as a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

In any of the above embodiments, the compound or salt can exist in one or more tautomeric forms. The term "tautomer" as used herein includes two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations. In an example, when $R^3$ is a group of the formula: $R^4CH=N-$ and $R^4$ includes a CH group bonded to the CH of $R^4CH=N-$, such as $-CH-CH=N-$, a tautomer can be represented by the formula: $-C=CH-NH-$. Thus, the following structural representations are tautomeric to each other:

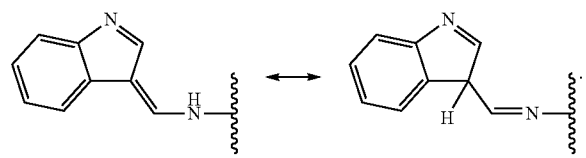 [SMILES: *N/C=C1\C=Nc2ccccc21 ; *N=CC1C=Nc2ccccc21]

The dose administered to a mammal, particularly, a human, in accordance with the present invention should be sufficient to effect the desired response. Such responses include reversal or prevention of the adverse effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the animal or mammal.

The therapeutically effective amount of the compound or compounds administered can vary depending upon the desired effects and the factors noted above. Typically, dosages can be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments, administration of the therapeutically effective amount of the compound or compounds involves administering to the subject from about 5 mg/m$^2$ to about 50 mg/m$^2$, such as from about 10 mg/m$^2$ to about 40 mg/m$^2$ per day. It is currently believed that a single dosage of the compound or compounds is suitable; however, a therapeutically effective dosage can be supplied over an extended period of time or in multiple doses per day. Thus, unit dosage forms also can be calculated using a subject's body surface area based on the suitable ranges recited above and the desired dosing schedule.

In accordance with certain embodiments, the inventive methods further comprise administering one or more additional anti-cancer agents to the mammal. The additional anti-cancer agents can be any suitable anti-cancer agents. Non-limiting examples of suitable anti-cancer agents include abarelix, aldesleukin, alemtuzumab, altretamine, amifostine, aminoglutethimide, anastrazole, arsenic trioxide, asparaginase, azacitidine, azathioprine, BCG vaccine, bevacizumab, bexarotene, bicalutamide, bleomycin sulfate, bortezomib, bromocriptine, busulfan, capecitabine, carboplatin, carmustine, cetuximab, chlorambucil, chloroquine phosphate, cladribine, cyclophosphamide, cyclosporine, cytarabine, dacarbazine, dactinomycin, daunorubicin hydrochloride, daunorubicin citrate liposomal, dexrazoxane, docetaxel, doxorubicin hydrochloride, doxorubicin hydrochloride liposomal, epirubicin hydrochloride, estramustine phosphate sodium, etoposide, estretinate, exemestane, floxuridine, fludarabine phosphate, fluorouracil, fluoxymesterone, flutamide, fulvestrant, gefitinib, gemcitabine hydrochloride, gemtuzumab ozogamicin, goserelin acetate, hydroxychloroquine, hydroxyurea, idarubicin hydrochloride, ifosfamide, imtinib mesylate, interferon alfa-2a, interferon alfa-2b, irinotecan hydrochloride trihydrate, letrozole, leucovorin calcium, leuprolide acetate, levamisole hydrochloride, lomustine, lymphocyte immune anti-thymocyte globulin (equine), mechlorethamine hydrochloride, medoxyprogestone acetate, melphalan, mercaptopurine, mesna, methotrexate, mitomycin, mitotane, mitoxantrone hydrochloride, nilutamide, oxaliplatin, paclitaxel, pegaspargase, pentostatin, plicamycin, porfimer sodium, procarbazine hydrochloride, streptozocin, tamoxifen citrate, temozolomide, teniposide, testolactone, testosterone propionate, thioguaine, thiotepa, topotecan hydrochloride, tretinoin, uracil mustard, valrubicin, vinblastine sulfate, vincristine sulfate, and vinorelbine.

When an additional anti-cancer agent is administered to the mammal, the additional anti-cancer agent can be administered at any suitable dosage, for example, at a dosage that is known to be clinically effective for the anti-cancer agent when used as a monotherapy for cancer. It is also suitable to administer the additional anti-cancer agent at a dosage that is less than or higher than a dosage when used as a monotherapy for cancer. The additional anti-cancer agent can be administered simultaneously or sequentially with one or more of the inventive compounds. Such administration regimens are well known to those of skill in the art.

The Compounds of the Invention Induced Cytoplasmic Vacuolization

A family of five small molecules that induced cytoplasmic vacuolization in human cells was discovered in a high throughput screen for compounds that induce excess DNA replication selectively in cancer cells compared to nonmalignant cells (18, 19). Of the 127 most promising candidates from the 343,078 molecules screened, 77 were rescreened at 12 different concentrations in order to confirm the primary results. Of these compounds, 40 were selected for further analysis. Unexpectedly, five of these compounds rapidly induced accumulation of cytoplasmic vacuoles that were readily visible by light microscopy (FIG. 1A). Vacuolization was induced in a wide variety of human cells, including normal mammary epithelia and fibroblasts, immortalized cells, and cells derived from human cancers and from patients with Huntington's, Parkinson's, Alzheimer's or Hutchinson-Gilford progeria disease. The potency of these molecules to induce vacuolization depended on which molecule was tested, its concentration, and the length of time that cells were cultured in its presence. The concentration required to induce vacuolization in osteosarcoma U2OS cells varied 400-fold, with the most potent, compound 1 when compared to the least potent, compound 3 (FIG. 1B).

This family of small molecules also induced accumulation of two autophagosome biomarkers, the phosphatidylethanolamine conjugate (LC3-II) of MAPILC3 protein (LC3-I), and the SQSTM1/Ubiquitin-Binding Protein p62 (p62) (examples in FIG. 10). As with vacuolization, the concentrations required to detect these effects depended on the molecule tested (summarized in FIG. 1B). The concentration required to detect accumulation of LC3-II varied by >36-fold among the five molecules. Similarly, the concentration required to inhibit cell proliferation and decrease in ATP cotent inside cell varied by 37-fold and >29-fold, respectively. Furthermore, the concentrations required to induce LC3-II accumulation, to inhibit cell proliferation, or to inhibit viability as measured by loss of ATP were greater than the concentrations required to observe vacuolization of the same cells. This difference was about 30-fold for compound 1, about 10-fold for compound 4, about 15-fold for compound 5, and two to three-fold for either compound 3 and compound 2.

Vacuolization Resulted from Lysosomal Enlargement

Figure 2A:
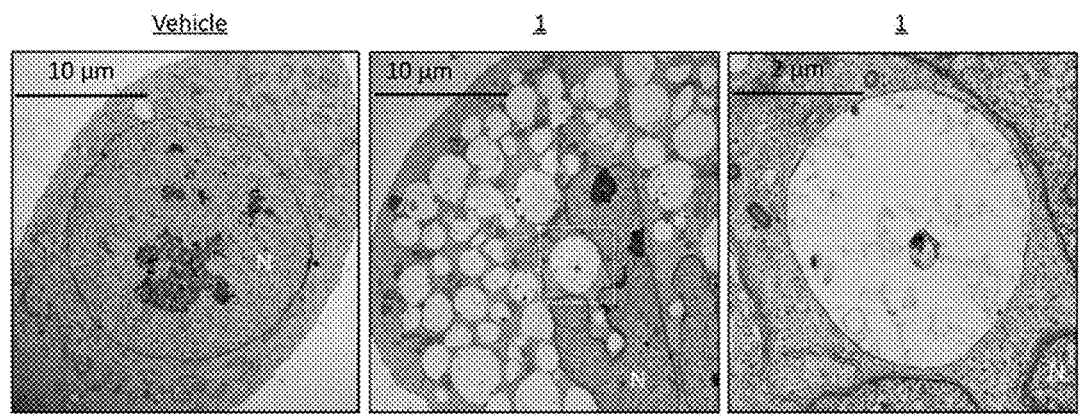
FIG. 2A shows electron microscopic analysis of thin sections of cell pellets of U2OS cells that were cultured in the presence of either vehicle or 2 µM compound 1 for 2 hrs. Nucleus is marked 'N'. Indicated vacuole in 10 µm image is magnified in 2 µm image. Thus, compounds of the invention induced accumulation of enlarged vacuoles with a single membrane, characteristic of lysosomes.
Figure 2B:
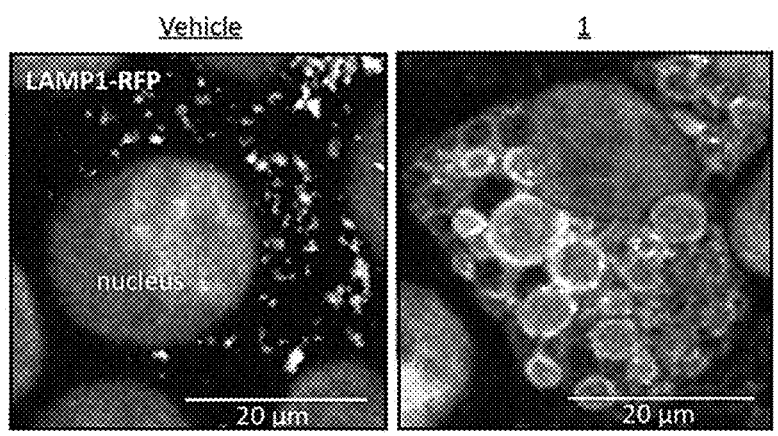
FIG. 2B shows confocal microscopy of U2OS cells that were transfected with baculovirus expressing LAMP1-RFP and then cultured overnight to label lysosomes before addition of either vehicle or 1 µM compound 1 for 4 hrs. LAMP1 protein is a lysosomal membrane marker. Nuclei were stained with DAPI. Therefore, the enlarged cytoplasmic vacuoles induced by compounds from this invention are lysosomes.
Figure 2C:
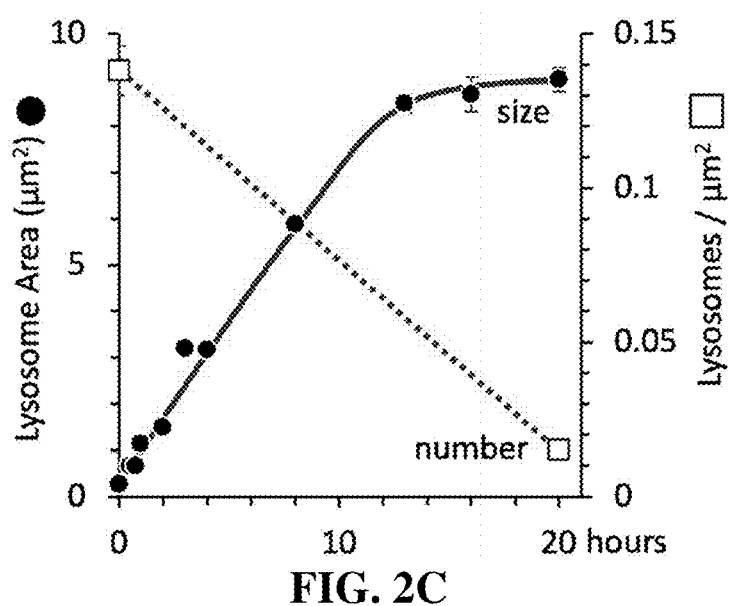
FIG. 2C shows the diameters of LAMP1-RFP-labeled vacuoles (lysosomes) from FIG. 2B as measured using image processing software with lysosomes approximated as circles. The selection of circular, enlarged, lysosomes was carried out using a size mask of 0.5 to 5.0 µm². Punctate lysosomes were selected with a size mask of 0.1 to 1.5 µm². Thresholds were the same for all images. Clustered lysosomes were not included in the size analysis. The mean area (µm²)±SEM was plotted (O). From 235 to 545 lysosomes were measured for each time point. The number of lysosomes per µm² (E) was determined at the beginning and end of this experiment and plotted on a separate Y-axis. Thus, compounds from this invention increased the size of lysosomes while decreasing the number of lysosomes in a time dependent manner.
Figure 2D:
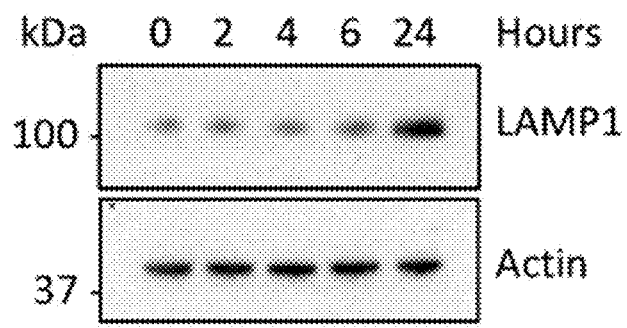
FIG. 2D shows Western immuno-blotting of U2OS cells that were seeded into 6-well plates ($10^5$ cells/well) and cultured overnight before adding 1 µM compound land culturing for the times indicated. LAMP1 protein was identified in total cell lysates β-actin was used as a loading control.
Figure 2E:
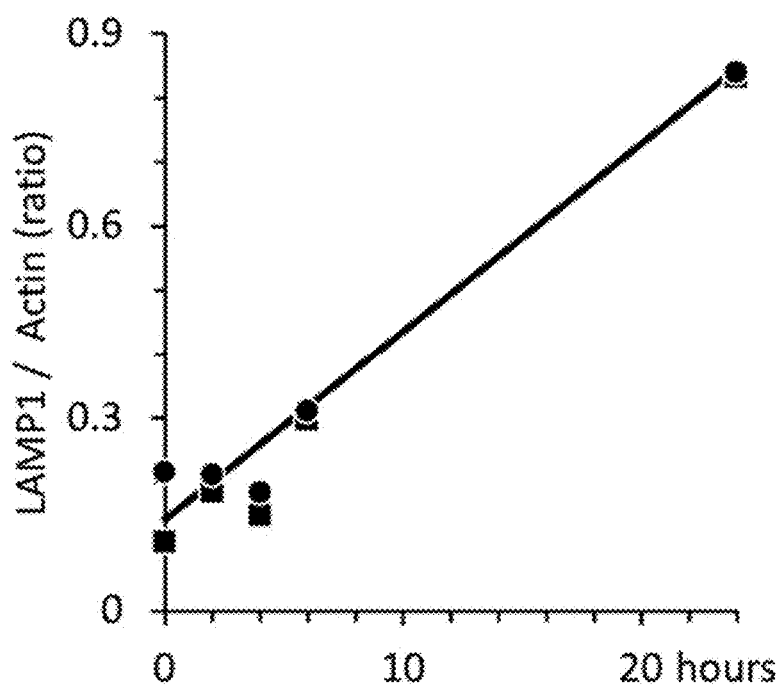
FIG. 2E shows the ratios of LAMP1 protein to β-actin as determined by densitometry for two independent experiments. Taken together with data in FIG. 2C, the increase in LAMP1 protein suggests that new lysosomes are synthesized over time and then fuse together.

The compounds of the invention rapidly induced accumulation of vacuoles in human cells that were visible by light microscopy (FIG. 1A), which were subsequently identified as enlarged lysosomes. Electron microscopy of cells treated with compound 1 revealed the accumulation of large empty vacuoles with a single membrane (FIG. 2A). Fluorescence microscopy showed that these vacuoles were labeled with RFP-tagged LAMP1 (LAMP1-RFP) (FIG. 2B), thereby identifying them as enlarged lysosomes. The size of LAMP1-labeled vacuoles increased 9-fold within 20 hours as the number of detectable lysosomes decreased by an equivalent amount (FIG. 2C). Western immuno-blotting analysis revealed a comparable increase in the cellular level of endogenous LAMP1 protein (FIG. 2D, E), revealing that compound 1 did not prevent lysosome synthesis. Therefore, the accumulation of enlarged lysosomes must have resulted either from increased lysosome fusion, or from decreased lysosome fission.

Lysosomal Enlargement Required Homotypic Lysosome Fusion

Figure 3A:
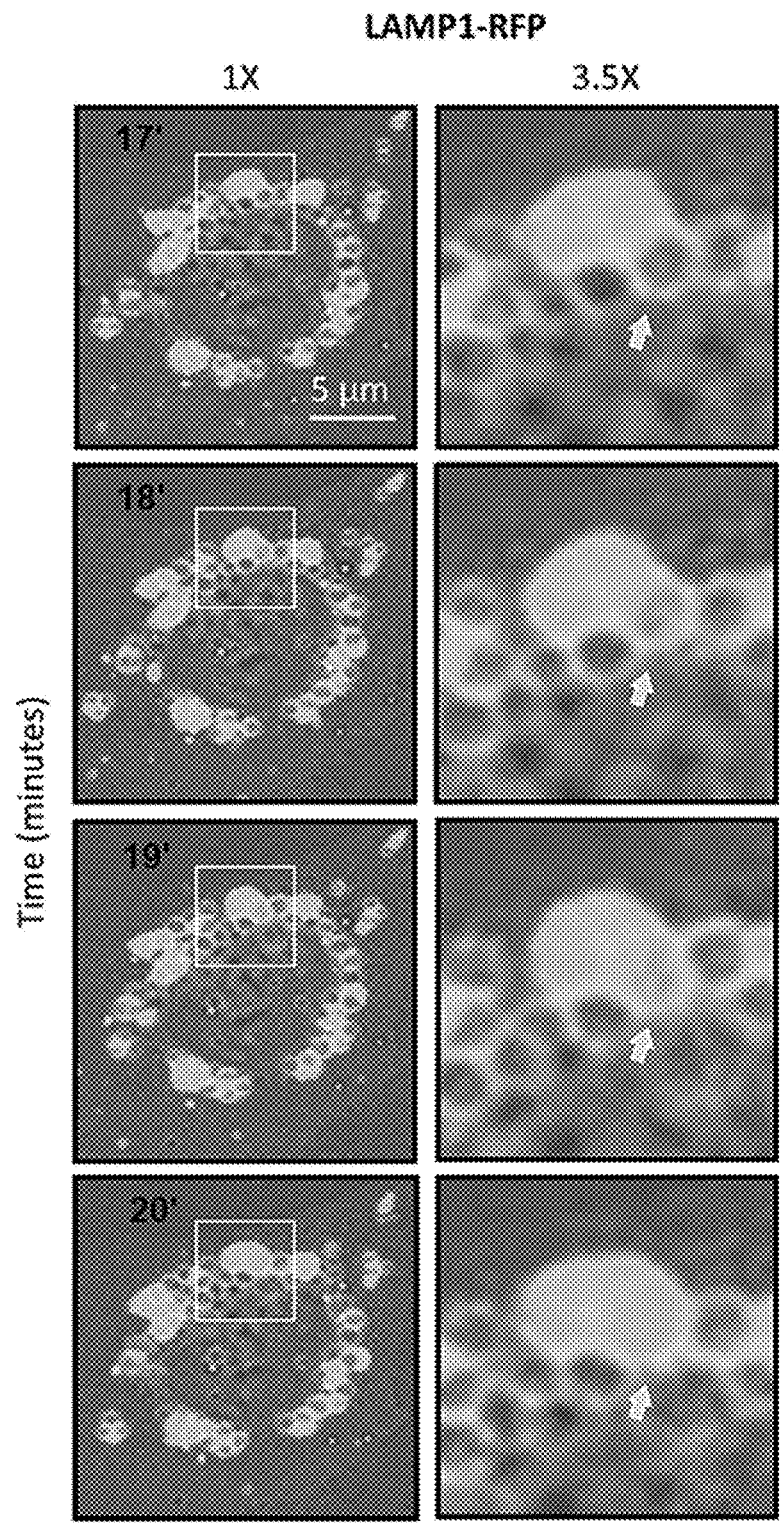
FIG. 3A-C show that enlarged lysosomes resulted from homotypic lysosome fusion. Compound 1 inhibited lysosomal fission without effecting homotypic lysosomal fusion.
Figure 3B:
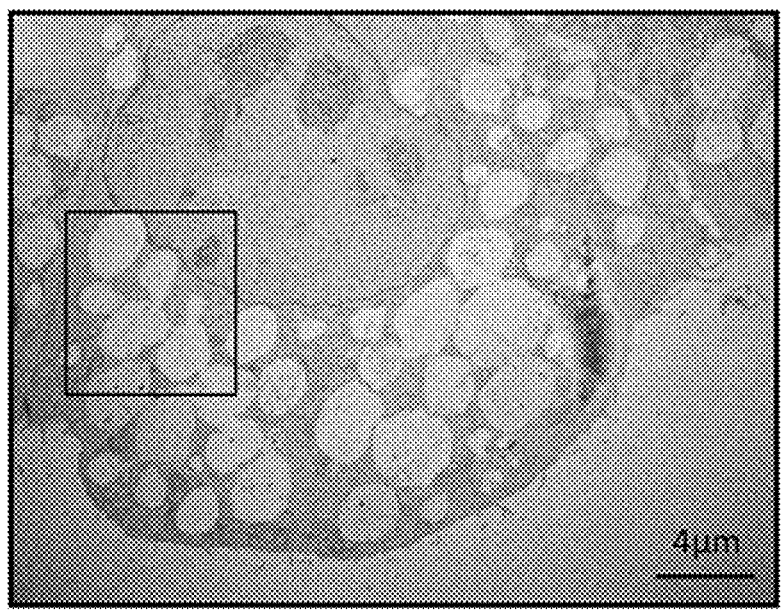

The size of cytoplasmic vesicles is the result of a tightly controlled balance between fusion and fission (20). To determine whether or not lysosomal enlargement involved homotypic lysosome fusion, cells were transfected with a LAMP1-RFP expression vector and then treated with compound 1, as in FIG. 2B. Time-lapse imaging of live cells expressing LAMP1-RFP protein revealed that lysosomes were undergoing homotypic fusion in the presence of compound 1. For example, in one 3-minute segment from this video, a large red lysosomal mass can be seen fusing with an adjacent enlarged lysosome (FIG. 3A). Electron micrographs of thin sections through these cells revealed structures consistent with lysosomes undergoing fusion (FIG. 3B, C).

Figure 5D:
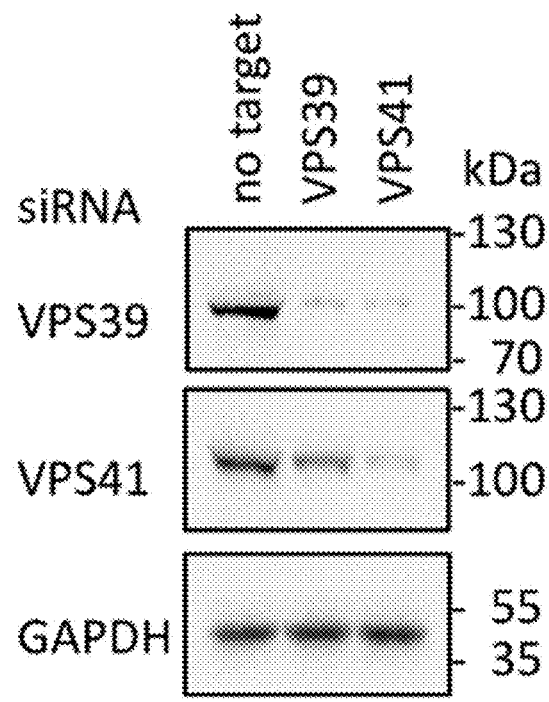
Figure 5E:
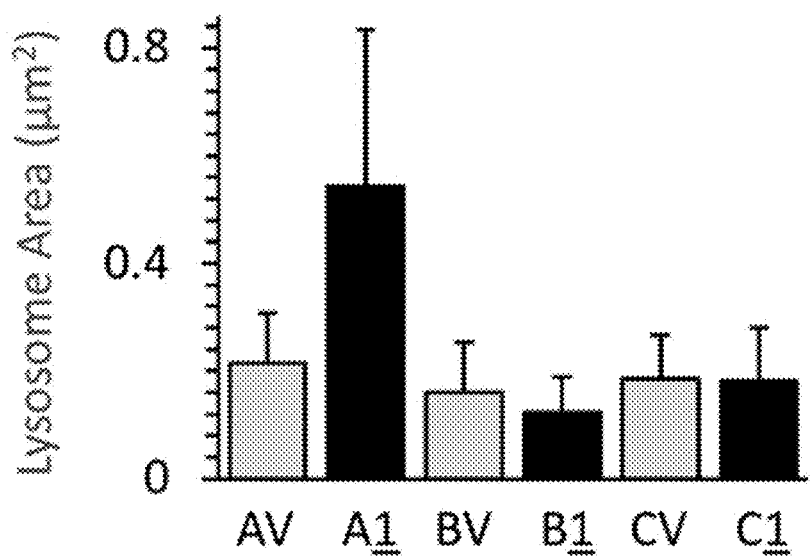
FIG. 5E shows quantitation of lysosome area for FIG. 5A-C.
Figure 6A:
FIG. 6A-E shows that ablation of an essential lysosome fusion gene prevented lysosome enlargement by the compounds of the invention. Wild-type HeLa cells (FIGS. 6A and 6B) and a derivative HeLa cell line in which the BORCS5 gene was ablated (FIGS. 6C and 6D) were cultured for 30 minutes in the presence of either vehicle (FIGS. 6A and 6C) or 1 μM compound 1 (FIGS. 6B and 6D). Scale bar is 10 μm.
Figure 6B:
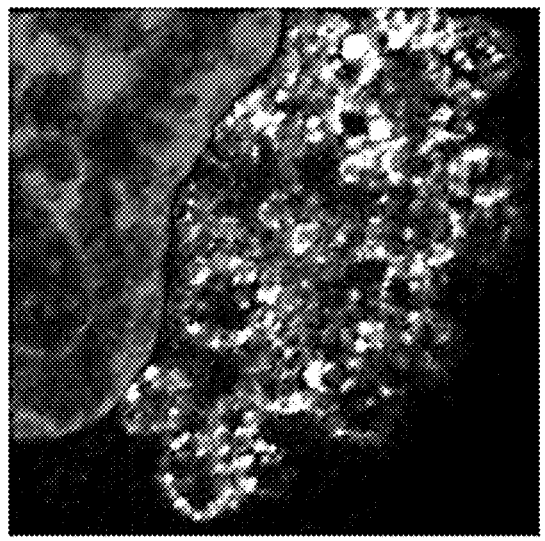
Figure 6C:
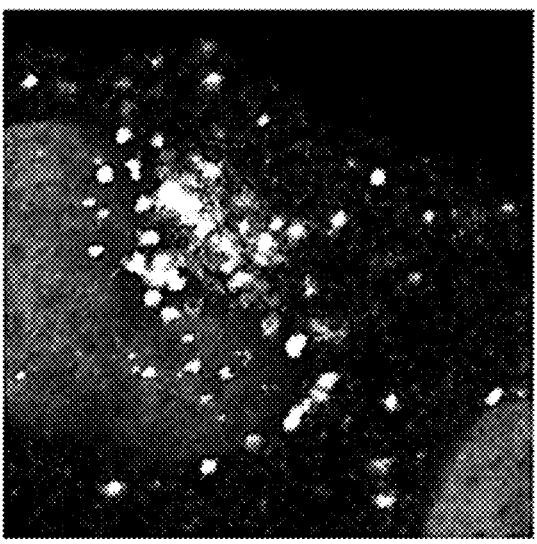
Figure 6D:
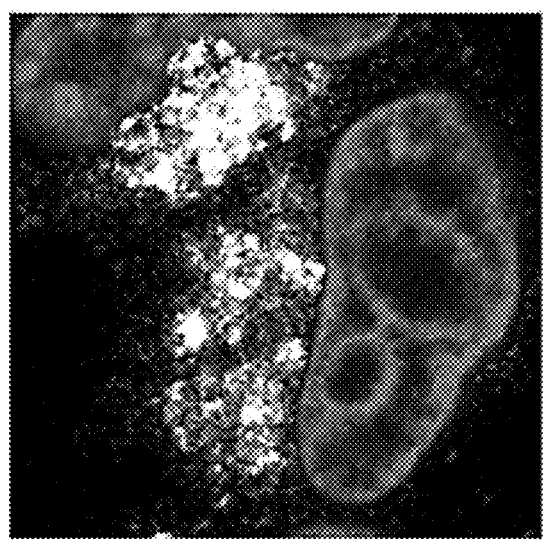
Figure 6E:
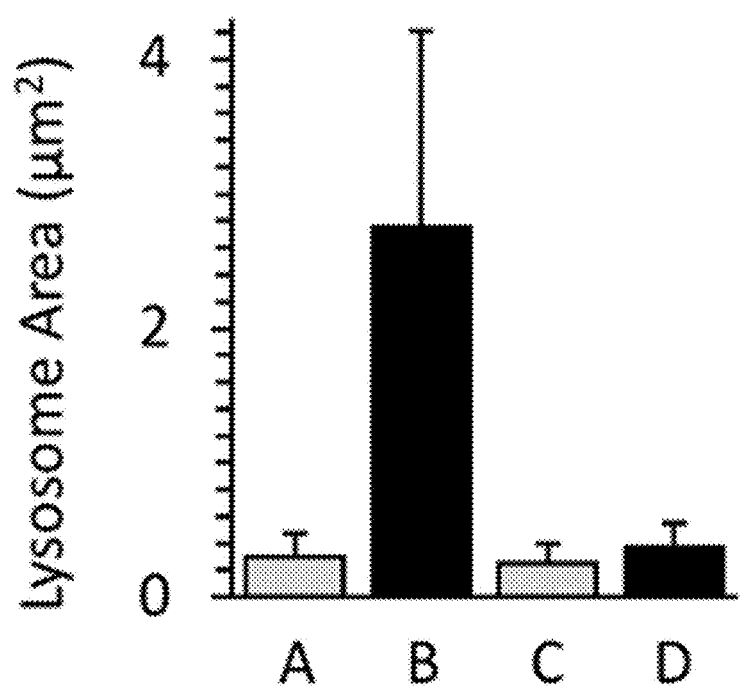

Homotypic fusion between lysosomes and heterotypic fusion between lysosomes and other organelles involves assembly of a trans-SNARE complex and the function of several regulators, including the multisubunit HOPS and BORC complexes (21-27). Therefore, to determine whether or not compound 1-induced lysosomal enlargement also required these proteins, cells were challenged by three different manipulations. First, cells were treated briefly with N-ethylmaleimide (NEM) in order to irreversibly inactivate the 'N-ethylmaleimide sensitive factor' (NSF) required for SNARE complex disassembly and recycling (28, 29) (enlargements FIG. 4A-E). Second, cells were transfected with siRNAs targeting the HOPS subunits VPS39 and VPS41 (21) in order to suppress expression of these subunits before adding either vehicle or compound 1 to the culture medium (FIG. 5). Finally, cells lacking the BORCS5 (aka myrlysin) subunit of BORC (21) were cultured in the presence of either vehicle or compound 1 and then stained with anti-LAMP1 antibody (FIG. 6). Staining for endogenous LAMP1 showed that all of the above treatments reduced swelling of lysosomes induced by compound 1. Taken together, these experiments demonstrated that ongoing lysosome fusion was a prerequisite for compound 1-induced lysosome enlargement and concomitant aggregation on the perinuclear area.

Enlarged Lysosomes Resulted from Reversible Inhibition of Lysosome Fission

Figure 7A:
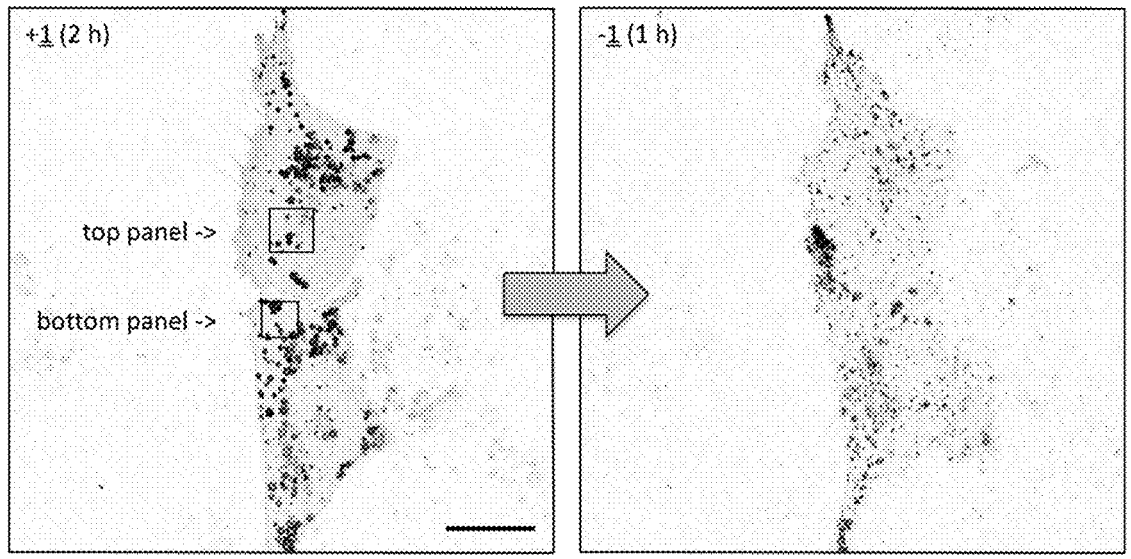
FIGS. 7A and 7B shows micrographs of enlarged lysosomes that formed in the presence of compound 1 which underwent fission via tubulation when compound 1 was removed.
Figure 7B:
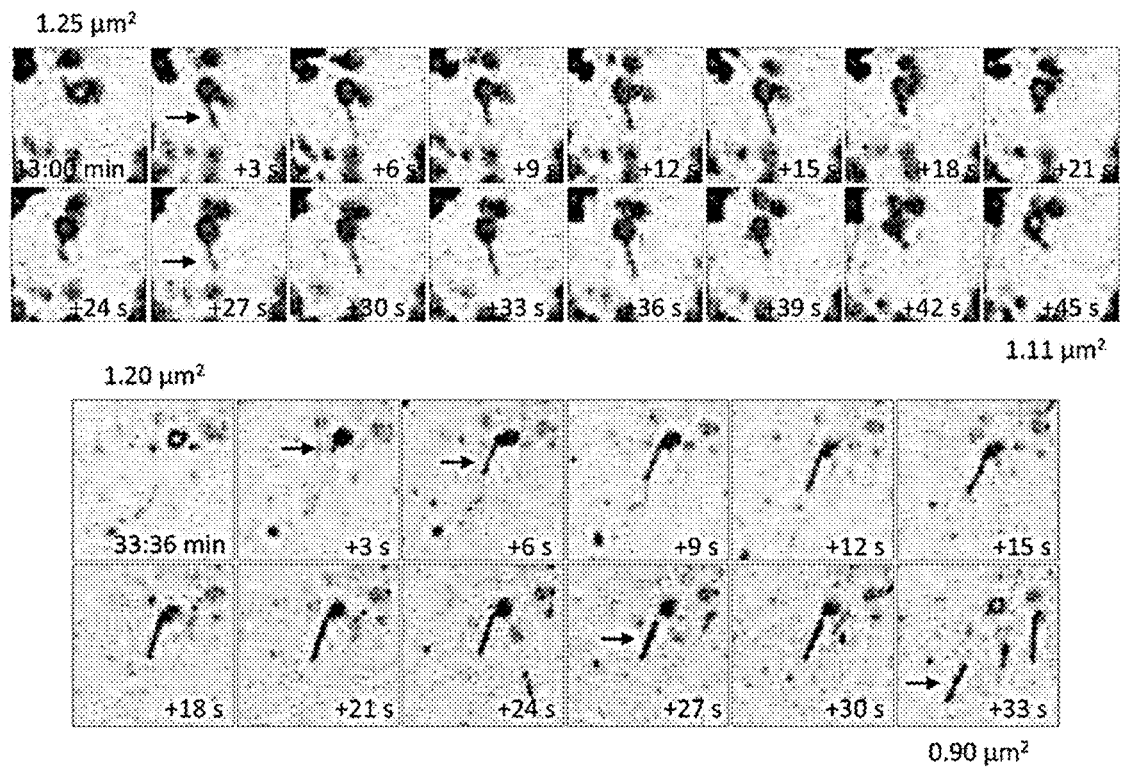

Cells cultured in the presence of any member of the compound 1-family for 24 hours accumulated vacuoles, and when these cells were then transferred to fresh culture medium without the compound present, the vacuoles disappeared. Moreover, time lapse microscopy of live cells expressing LAMP1-RFP protein demonstrated that the enlarged lysosomes that accumulated in the presence of compound 1 as cytoplasmic vacuoles reverted into small fluorescent puncta when cells were transferred to fresh culture medium without compound 1. Enlarged lysosomes quickly began undergoing fission into smaller lysosomes, a process that occurred at 3 to 6 second intervals. Lysosomal motility and size reverted to their original state within one hour. Multiple events of lysosome tubules budding from single lysosomes could be observed throughout the field of view (FIG. 7). When compound 1 was removed, the removal of membrane from single enlarged lysosomes in the form of tubules led to the reduction of the size of the lysosome, thereby demonstrating that compounds of the invention inhibited lysosome fission.

Lysosomal Enlargement Impaired Trafficking Not Acidification

Lysosomes have an acidic lumen (pH 4.5-5.0) and contain approximately 60 different soluble hydrolases that are active only under these conditions (30). To determine whether or not lysosomal enlargement induced by the compounds of the invention altered lysosomal acidification, the pH of individual lysosomes was quantified using a ratiometric protocol. Lysosomes in U2OS cells were preloaded with Oregon Green 488 dextran, and the cells were then cultured in the presence of 1 μM compound 1 for 4 hours before measuring the ratio of fluorescence at two separate wavelengths. Compound 1 did not affect lysosomal acidity significantly (FIG. 8A). Fluorescent images of the cells confirmed that compound 1 treated cells contained enlarged lysosomes.

Figure 8C:
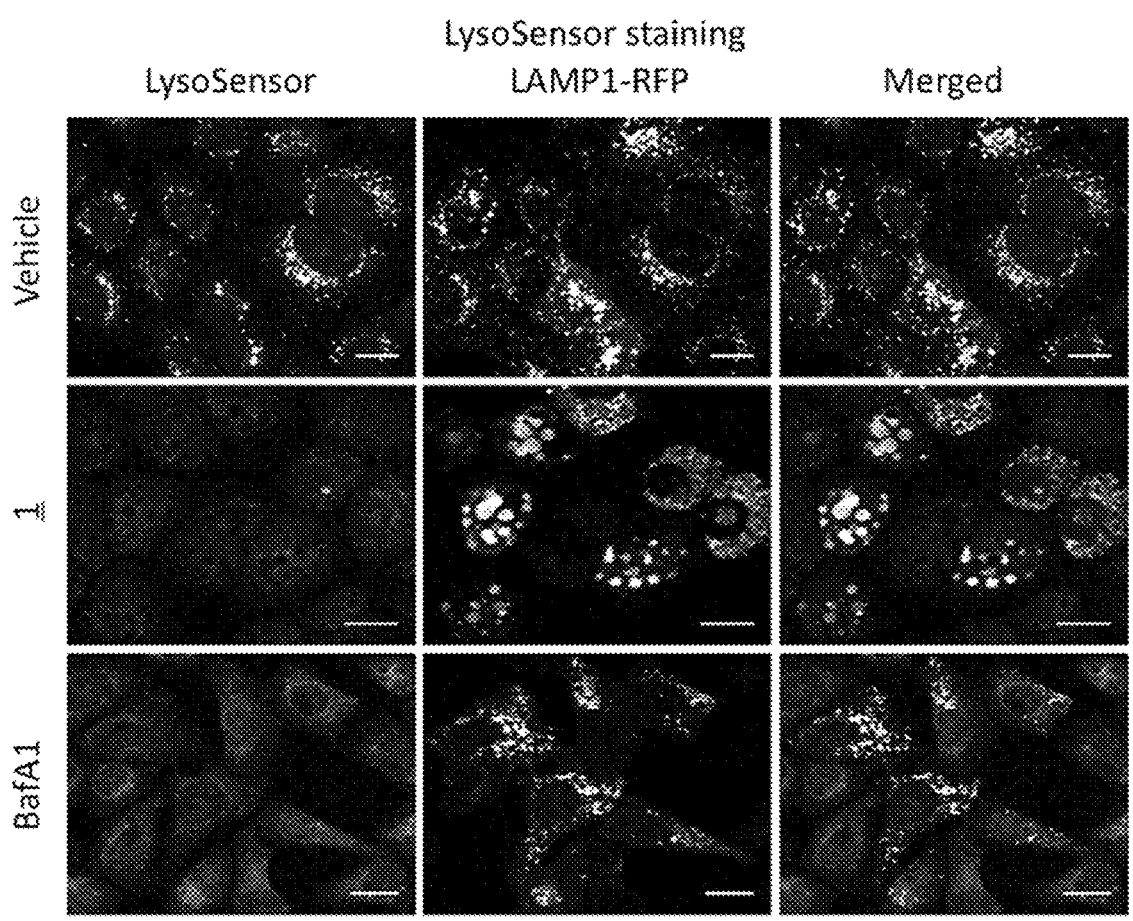
Figure 9A:
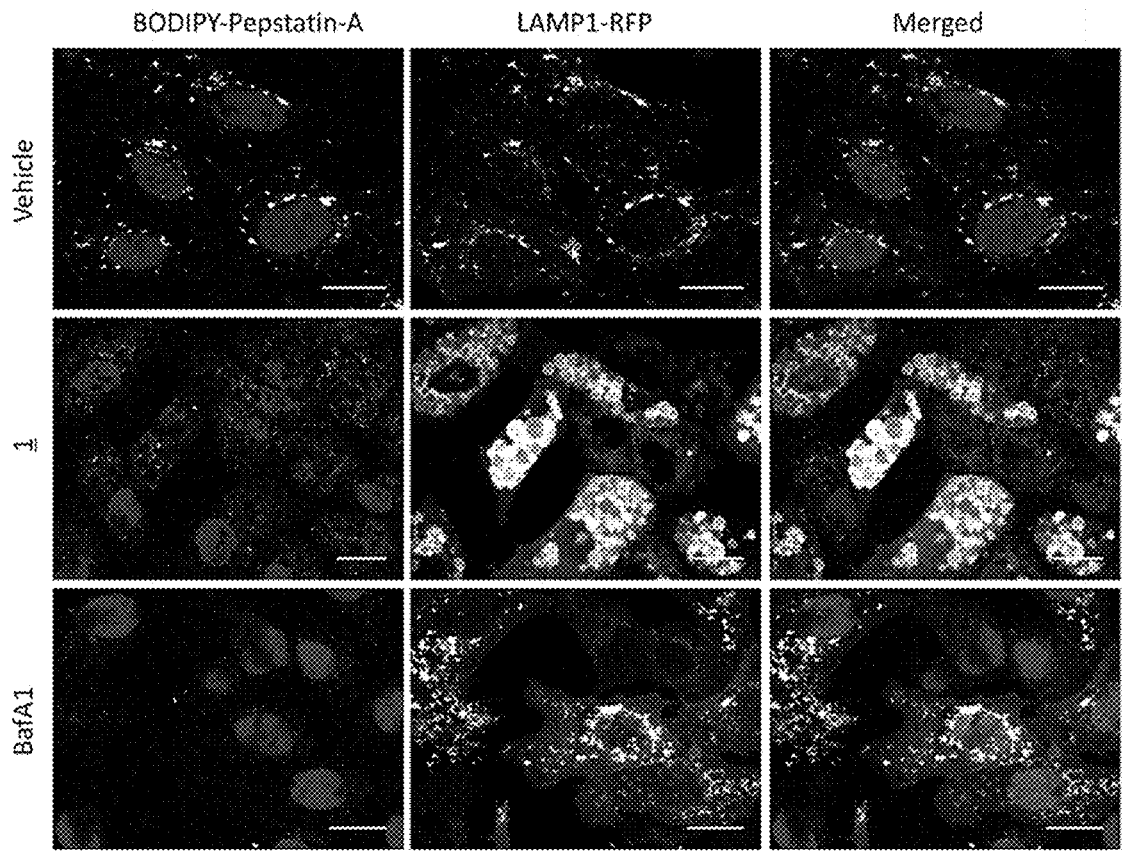
FIG. 9A shows confocal microscopic images of U2OS cells that were cultured for 4 h in the presence of either vehicle, 1 μM compound 1 or 50 nM bafilomycin A1 (BafA1), and then live cells were stained as indicated according to the manufacturer's instructions and viewed immediately. Cells that had been transfected with LAMP1-RFP expression vector were then stained with BODIPY-FL-Pepstatin-A, a green-fluorescent probe that stains lysosomes in live cells by binding selectively to mature cathepsin D (CTSD) at acidic pH. Nuclei were stained with DAPI, and cells were visualized by confocal microscopy. The absence of green vacuoles revealed either that BODIPY-FL-Pepstatin-A did not accumulate in the enlarged lysosomes. Bars represent 20 μm.

To confirm these results, lysosomal acidity was evaluated in compound 1 treated U2OS cells by several additional methods. LysoTracker Green DND-26, a fluorescent probe commonly used for staining acidic compartments in live cells (32), gave results consistent with those obtained by ratiometric analysis (FIG. 8B). Since the pKa for LysoTracker was not available, U2OS cells were also stained with LysoSensor Green DND-189, a fluorescent probe with a pKa-5.2 that fluoresces only in the acidic compartments of live cells (FIG. 8C). As expected, LysoSensor Green produced green puncta throughout the cytoplasm of cells cultured with vehicle that were largely coincident with RFP-LAMP1 labeled puncta in the same cells, but not in cells treated with bafilomycin-A1, a specific inhibitor of the vacuolar-ATPase essential for lysosome acidification[33]. However, LysoSensor Green did not produce green puncta in cells treated with compound 1. Similar results were obtained with BODIPY FL-pepstatin A (FIG. 9A), a green-fluorescent probe that stains lysosomes in live cells by binding selectively to mature cathepsin D at pH 4.5 (34). These results suggested that compound 1 induced lysosomal enlargement accompanied by lysosomal deacidification.

A simple explanation for this conundrum arose when cells were stained with Acridine Orange. In acidic compartments, Acridine Orange emits orange fluorescence, whereas in neutral pH environments, it emits green fluorescence (35). Acridine Orange also emits green fluorescence when bound to double-stranded DNA and orange fluorescence when bound to single-stranded DNA or RNA. Thus, in cells cultured with the vehicle, nuclear DNA appeared as bright intense green and cytoplasm appeared as light speckled green, but lysosomes were detected easily as bright orange puncta (FIG. 9C). In stark contrast, some of vacuoles in cells treated with compound 1 stained orange, but most of them were devoid of any fluorescence. Since the pKa of Acridine Orange is 9.65, it should fluoresce in cells wherever it accumulates. Moreover, the metachromatic shift observed when Acridine Orange accumulates in vesicles results from its increased concentration rather than a decrease in pH (35). Therefore, the accumulation of dark vacuoles revealed that Acridine Orange was eventually excluded from lysosomes as they continued to undergo homotypic fusion in the absence of fission. This exclusion mechanism readily accounted for the absence of lysosome staining by either LysoSensor or BODIPY FL-pepstatin A.

Figure 9B:
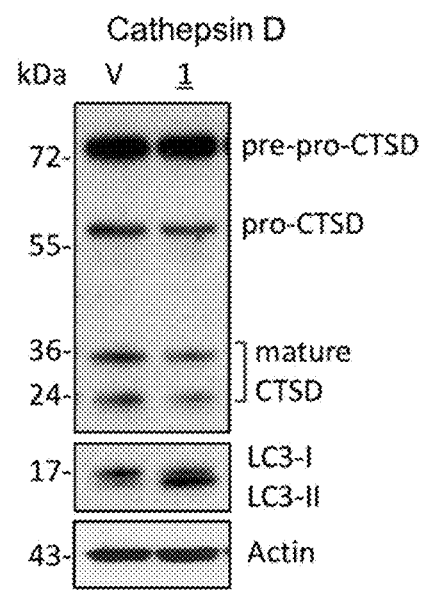
FIG. 9B shows Western immuno-blots of U2OS cells that were cultured for 4 h with vehicle (V) or compound 1. Mature and immature cathepsin D (CTSD), LC3-I, LC3-II, and β-actin proteins were identified by Western immuno-blotting, under the same conditions, and detected with specific antibodies and by co-fractionation with molecular mass markers (kDa). Cathepsin D maturation via proteolysis requires acidity.
Figure 9C:
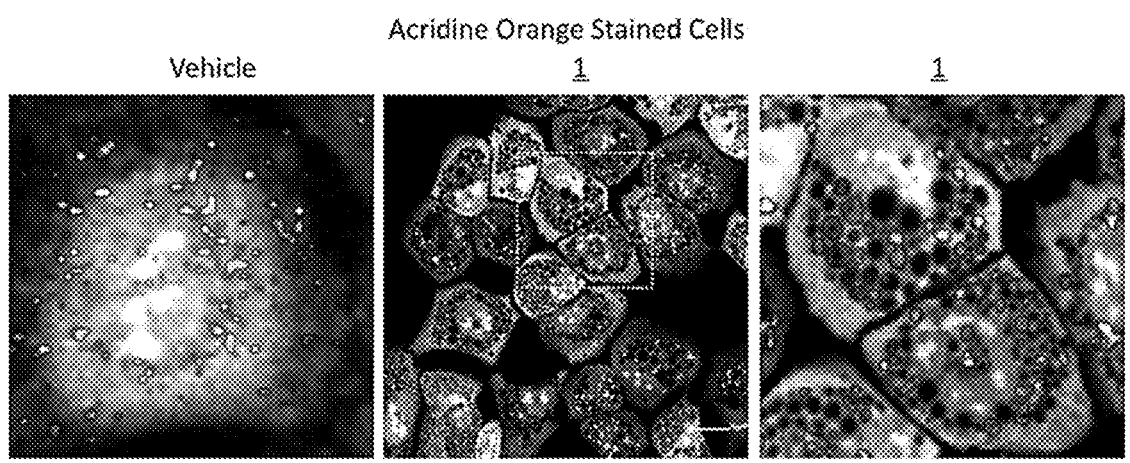
FIG. 9C shows that compounds of the invention impaired trafficking of molecules into lysosomes without altering lysosomal acidity. Micrographs of U2OS cells that were cultured for 4 h in the presence of either vehicle, 1 μM compound 1, and then live cells were stained with Acridine Orange according to the manufacturer's instructions and viewed immediately by confocal microscopy at 40×. In acidic compartments, Acridine Orange emits orange fluorescence, whereas in neutral pH environments, it emits green fluorescence. The absence of fluorescence in enlarged vacuoles reveals compartments that excluded acridine orange. Bar represents 20 μm.

To determine whether or not the compound 1-family affected enzymatic activities in lysosomes, the distribution of cathepsin D was examined before and after treatment of U2OS cells with compound 1 (FIG. 9B). Cathepsin-D is synthesized on the rough endoplasmic reticulum as a pre-pro-enzyme that undergoes several proteolytic cleavages during biosynthesis to produce the mature form (36). The 52 kDa pro-cathepsin-D is targeted to lysosomes, where it is cleaved into a mature enzyme consisting of two chains, 34 kDa and 14 kDa in size. The cellular levels of mature cathepsin D in compound 1-treated cells were about 50% of vehicle treated cells, suggesting that compound 1 impaired trafficking of pro-cathepsin into lysosomes (FIG. 9B).

Figure 10A:
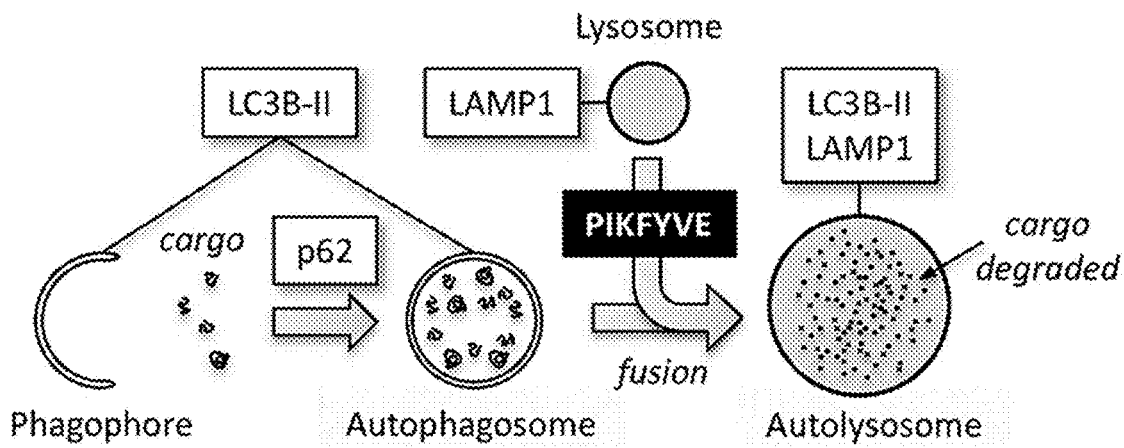
FIGS. 10A-C, 10Bi, and 10Ci show that compounds of the invention induced accumulation of autophagosome associated proteins as a function of compound concentration and time of exposure.

The Compounds of the Invention Induced Accumulation of Autophagosomal Biomarkers Autophagy begins with the formation of a double membrane structure that engulfs cargoes such as mitochondria, peroxisomes, ribosomes, and protein aggregates to form autophagosomes, a process requiring approximately 10 minutes (37) (FIG. 10A). LC3-II is recruited to autophagosome membranes, and p62 is an autophagy receptor that interacts directly with LC3-II as well as with ubiquitinated proteins. Autophagosomes survive for 10 to 25 minutes (38, 39) before fusing with lysosomes to form autolysosomes, which proceed to degrade the cargo. The entire process, termed autophagic flux, is active throughout the cell cycle (40).

Figure 10B:
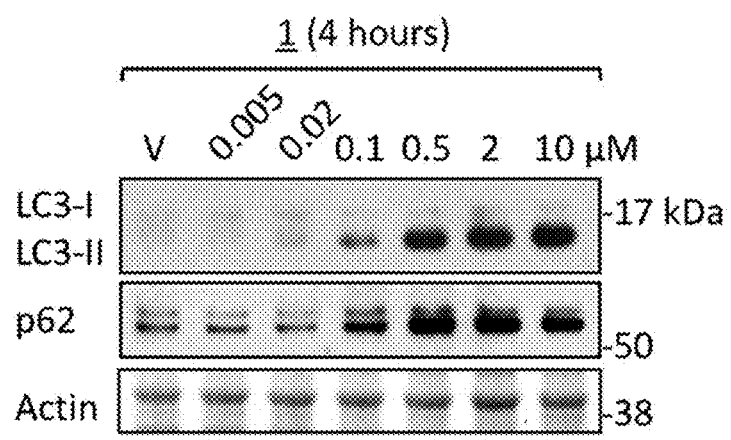
Figure 10C:
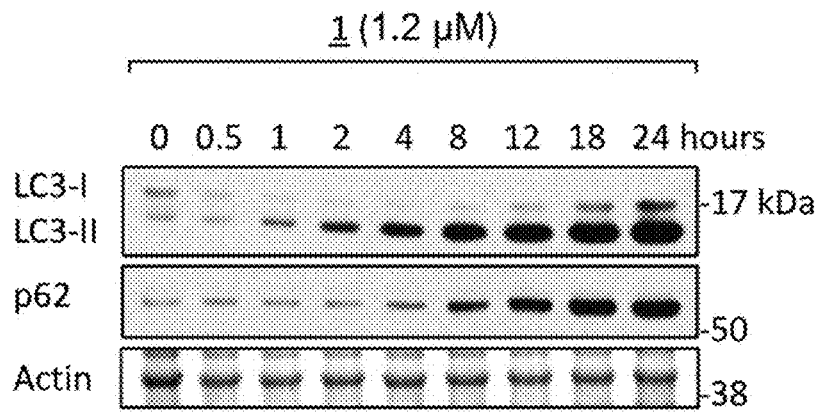
Figure 10B:
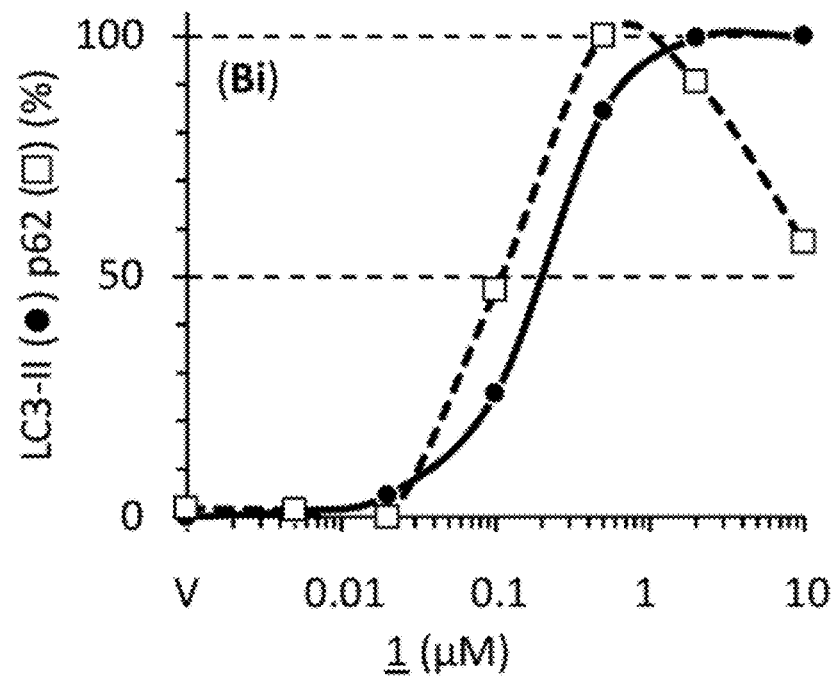
Figure 10C:
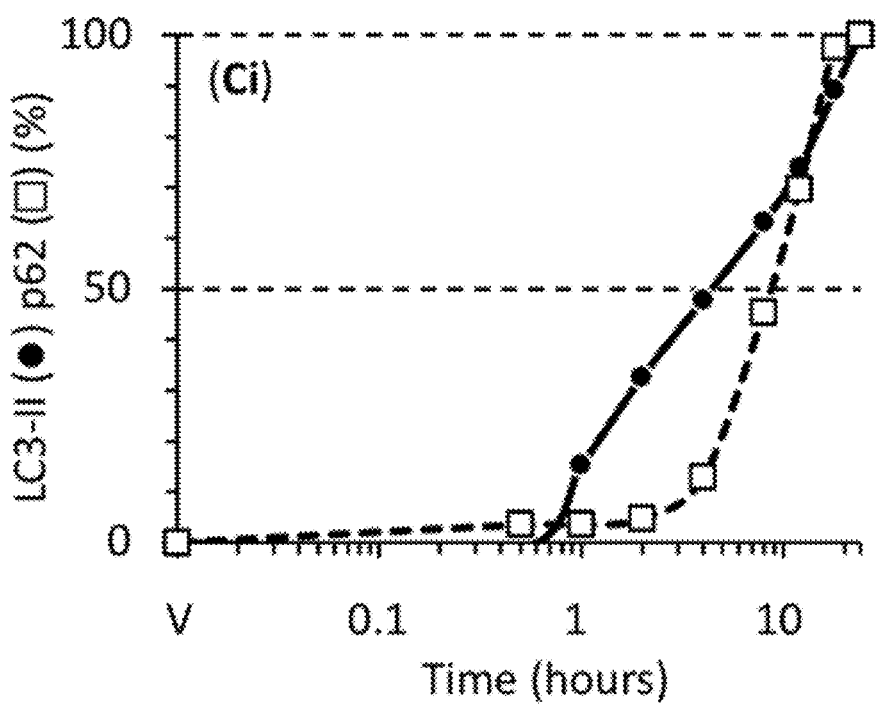

Under the same conditions in which the compound 1-family induced the accumulation of cytoplasmic vacuoles, Western immuno-blotting analysis revealed a concentration-dependent increase in the amount of LC3-II and p62, as illustrated using compound 1 (FIG. 10), as well as a time-dependent accumulation of LC3-II and p62 in which p62 accumulation was delayed about 3 hours relative to LC3-II (FIG. 10B, Bi). These results were consistent with the accumulation of autophagosomes. However, whereas 80% of the cells were vacuolated by 4 hours in 0.01-0.1 µM compound 1, near maximum levels of LC3-II accumulation required 0.1-0.5 µM compound 1 (FIG. 10C, Ci). Thus, inhibition of lysosome fission was at least 5-fold more sensitive to compound 1 than accumulation of autophagosomes. Nevertheless, the accumulated LC3-II and p62 proteins, like accumulated enlarged lysosomes, returned to their baseline values within 24 hours when compounds of the invention were removed (data not shown), demonstrating that the ability of the compounds of the invention to induce accumulation of autophagosomes, like their ability to induce accumulation of enlarged lysosomes, was readily reversible.

Figure 11A:
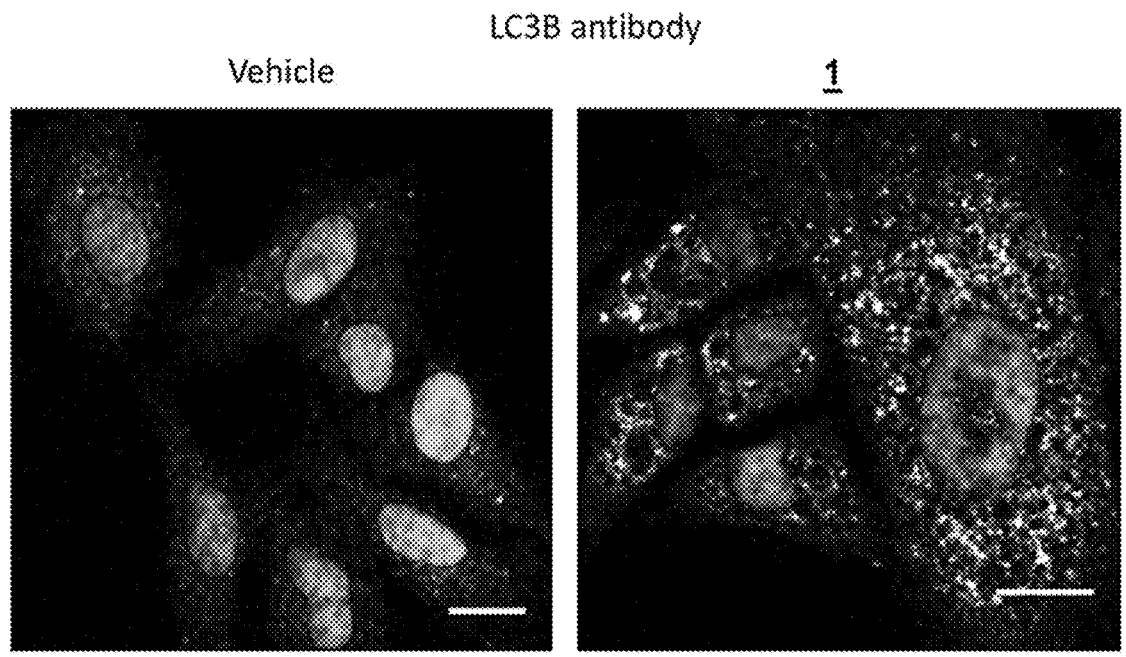
FIG. 11A-B, Ai, and Bi show compounds of the invention induced accumulation of autophagosomes.
Figure 11B:
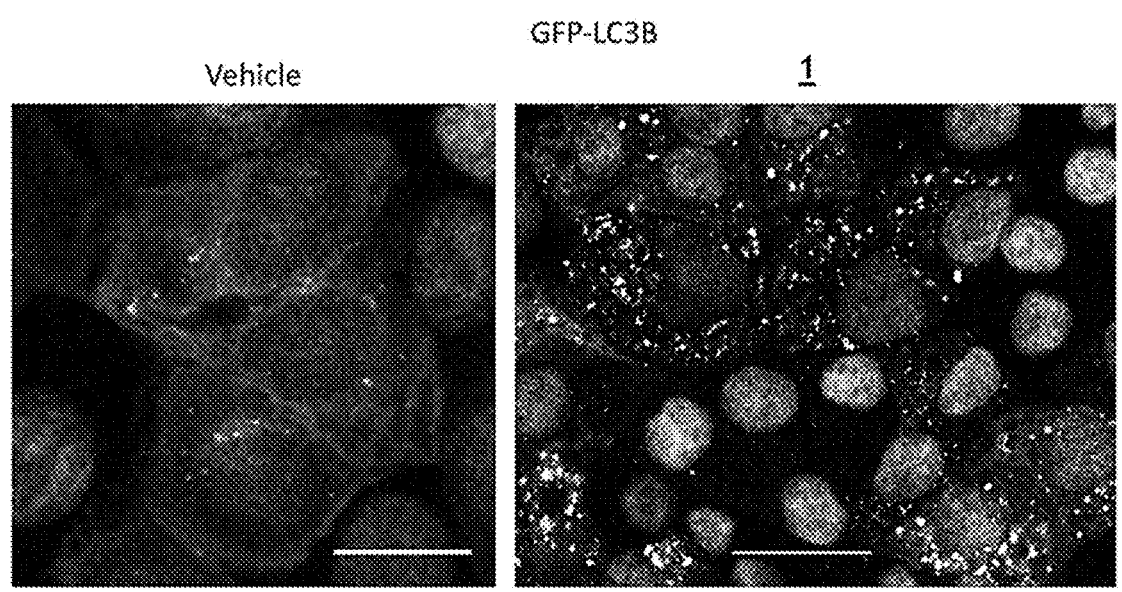
Figure 11A:
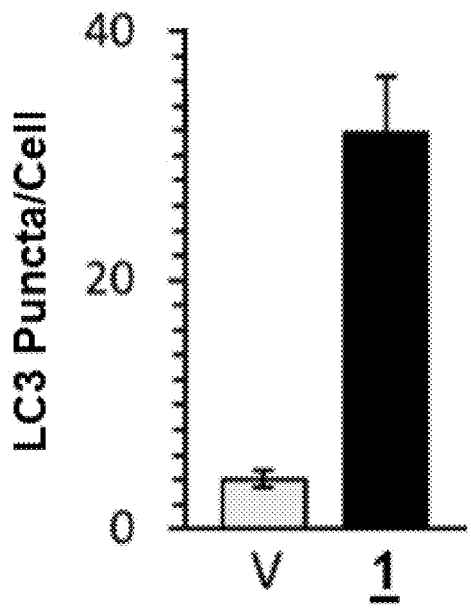
Figure 11B:
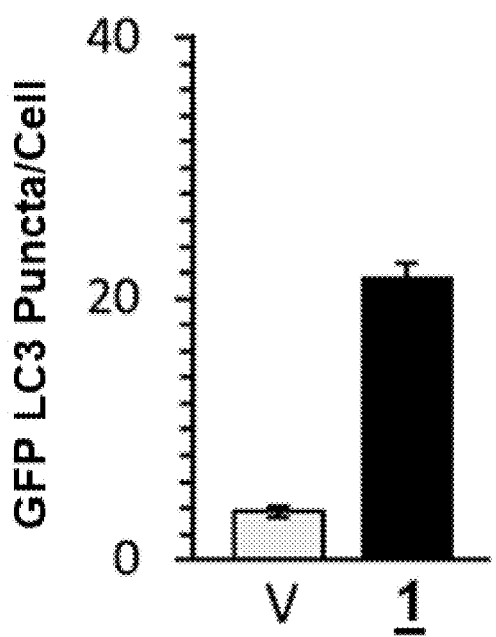

The Compounds of the Invention Prevented Heterotypic Fusion of Lysosomes with Autophagosomes In addition to enlarged lysosomes, electron microscopy of cells treated briefly with compound 1-family compounds revealed vesicular structures consistent with early and late stages in autophagy. Moreover, immuno-fluorescence microscopy revealed the presence of autophagosomes containing ubiquitinated cargos. LC3 puncta were evident either by staining cells with LC3 antibody, or by ectopic expression of GFP-tagged LC3, and compound 1 treated cells contained about 5-times the number of LC3 puncta than cells treated with vehicle (FIG. 11A). Moreover, cells ectopically expressing both GFP-tagged LC3 and RFP-tagged p62 accumulated both green and red puncta that co-localized to produce yellow puncta (FIG. 11B).

To determine whether the accumulation of autophagosomes resulted from induction of autophagy or from disruption of autophagic flux, cells were transfected with a vector expressing a modified tandem sensor RFP-GFP-tagged LC3B protein in which the green signal from a mutated GFP was suppressed in an acidic environment, with little or no effect on the red signal from RFP[41]. Therefore, in merged images, only red puncta indicated acidic autolysosomes; yellow puncta indicated either autophagosomes or non-acidic autolysosomes. Thus, normal autophagic flux is characterized by the presence of both red and yellow puncta, whereas disruption of autophagic flux produces yellow puncta.

When cells were cultured with compound 1, the fraction of yellow puncta increased 4-fold. Both red and yellow puncta were evident in cells treated with vehicle and in cells treated with compound 1, but when the colors were merged at least 80% of the puncta in cells treated with compound 1 were yellow (FIG. 12). Therefore, the compounds of the invention disrupted autophagic flux by preventing formation of an acidic environment.

Figure 13A:
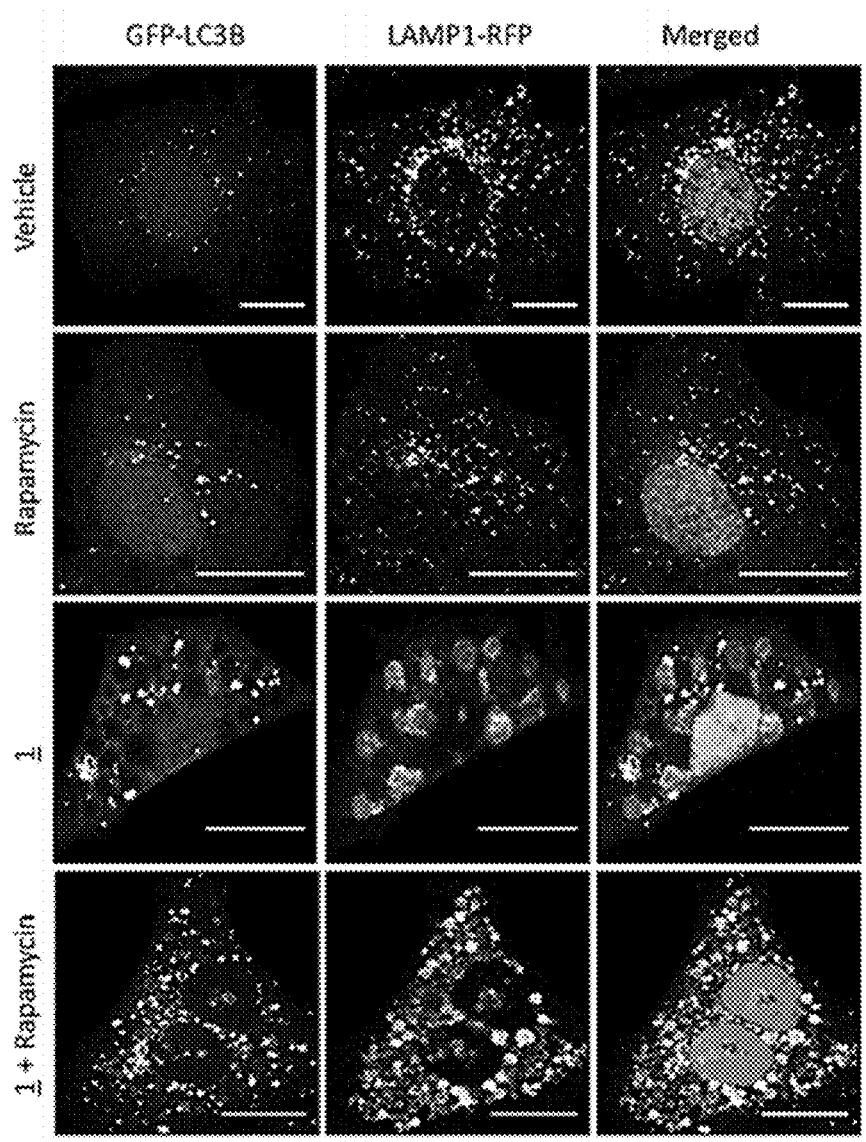
FIG. 13A-B confirms that compounds of the invention prevented accumulation of autolysosomes (autophagosomes fused with lysosomes). Confocal microscopic images are shown in FIG. 13A of U2OS cells that were co-transfected with a GFP-LC3B expression vector to label autophagosomes green and a LAMP1-RFP expression vector to label lysosomes red. Cells were then treated for 4 hrs with 1 µM rapamycin to induce autophagy, or with 1 µM compound 1 to disrupt autophagy, or with both 1 µM rapamycin and 1 µM compound 1. Cells were then fixed and viewed by confocal microscopy. Nuclei were stained with DAPI. Since rapamycin did not induce accumulation of either enlarged lysosomes or enlarged autophagosomes, visual quantitation of yellow puncta in merged images underestimates the result compared with the fraction of colocalized LAMP1-RFP and GFP-LC3B puncta per cell detected with ImageJ software as shown in FIG. 13B. The mean±SEM results from 50 cells is given for two independent experiments.
Figure 13B:
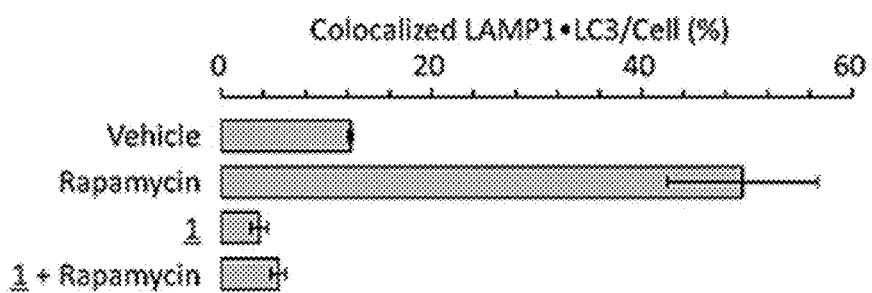

To determine whether or not the absence of an acidic environment resulted from failure of lysosomes to fuse with autophagosomes, cells were transfected with both GFP-LC3 and LAMP1-RFP expression vectors, and then cultured for 4 hours in the presence of vehicle, rapamycin, or both rapamycin and compound 1 (FIG. 13). Rapamycin is an established inducer of autophagy (42, 43). As expected, rapamycin induced accumulation of GFP-LC3 labeled autophagosomes (green), some of which were autolysosomes, as shown by co-localization with LAMP1-RFP on control cells. In contrast, GFP-LC3 and LAMP1-RFP labeled different populations of vesicles in cells cultured with either compound 1 or rapamycin and compound 1, despite the fact that the density of autophagosomes was at least 3-fold greater. Taken together, these experiments demonstrated autophagosomes accumulated in the presence of compound 1, because they failed to fuse with lysosomes.

The Compounds of the Invention and Bafilomycin-A1 Have Different Mechanisms

Bafilomycin-A1 (BafA1) is a specific inhibitor of the V-ATPase that disrupts autophagic flux by inhibiting both lysosome acidification and fusion of autophagosomes with lysosomes to form autolysosomes, two properties that are shared by the compounds of the invention, but BafA1 does not induce accumulation of large vacuoles (44, 45).

Therefore, to compare compounds of the invention directly with BafA1, GFP-LC3 and LAMP1-RFP proteins were expressed in U2OS cells, and the cells were then cultured in the presence of BafA1 compound 1, or both BafA1 and compound 1 (data not shown). The results confirmed that BafA1 did not induce formation of enlarged lysosomes, and that neither BafA1 nor compound 1 induced accumulation of autolysosomes. However, the LC3 puncta that accumulated in the presence of compound 1 were distinctly larger than those that accumulated in the presence of BafA1, suggesting that compound 1 promoted aggregation of autophagosomes. Electron microscopy of cells cultured in compound 1 and BafA1 revealed double membrane autophagosomes as well as small empty single membrane vacuoles ~0.1 µm in diameter, characteristic of lysosomes (46).

To evaluate this hypothesis, the cellular levels of LC3 protein in BafA1 and compound 1 treated cells were compared. BafA1 induced the accumulation of LC3-II above the level observed either in control cells or in cells treated with rapamycin. A comparable increase in LC3-II was induced by compound 1. However, addition of BafA1 to cells cultured in the presence of compound 1 did not significantly alter the level of LC3-II. Thus, both BafA1 and compounds of the invention caused accumulation of autophagosomes, but only compounds of the invention caused aggregation of autophagosomes and accumulation of enlarged lysosomes.

BafA1 also has been shown to prevent formation of cytoplasmic vacuoles that are induced by inhibition of the PIKFYVE phosphoinositide kinase (47). To determine whether or not BafA1 also prevented induction of the cytoplasmic vacuoles that are induced by the compounds of the invention, U2OS cells were cultured in the presence of BafA1, compound 1, or both BafA1 and compound 1. The results revealed that BafA1 prevented induction of vacuole accumulation by the compounds of the invention, suggesting that the compounds of the invention inhibited PIKFYVE activity.

Figures 14A, 14B:
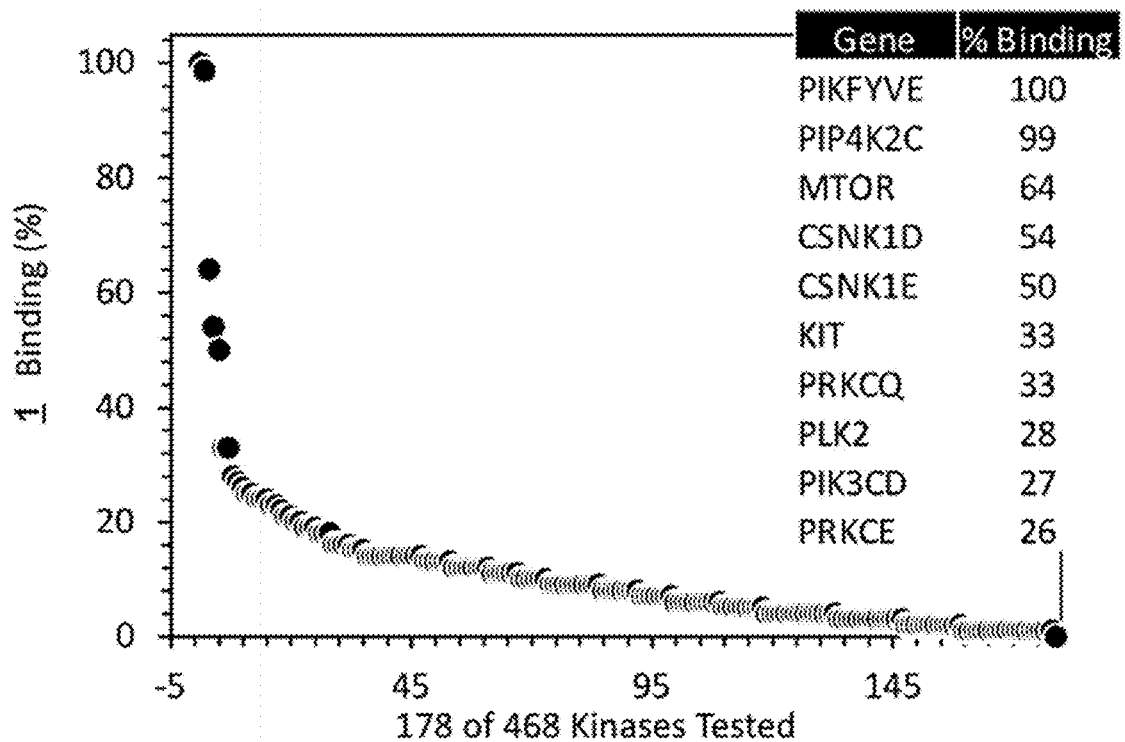
FIG. 14A-B shows that compounds of the invention bound specifically to the PIKFYVE phosphoinositide kinase protein with different affinities.

The Compounds of the Invention Selectively Inhibited the PIKFYVE Phosphoinositide Kinase The ability of BafA1 to prevent the compounds of the invention from inducing accumulation of enlarged lysosomes, and the similarity of the compounds of the invention to molecules that bind protein kinases (48) suggested that the compounds of the invention might inhibit phosphatidylinositol kinases. To address this hypothesis, a panel of 468 human kinases were screened for their ability to bind compound 1. In the presence of 10 µM compound 1, ten candidates had binding affinities for compound 1 of 25% or greater (FIG. 14). The top two candidates were PIKFYVE (phosphoinositide kinase FYVE-type zinc finger containing) and PIP4K2C (phosphatidylinositol-5-phosphate 4-kinase). PIKFYVE is a kinase that is essential for mouse development (49) and that prevents endosome enlargement and cytoplasmic vacuolization (50, 51). PIP4K2C is a kinase that is not essential for mouse growth and viability, but it is essential for the immune system (52), mTORC1 signaling (53), and regulation of autophagy (54). The third candidate was MTOR, a kinase that regulates autophagy (55). Therefore, the binding constants (Kd) for all five members of the compound 1-family were determined for each of these three proteins from two independent titration curves, as shown for compound 1. The results (FIG. 14B) revealed that compounds of the invention bound PIKFYVE 340 times better than PIP4K2C and 7200 times better than MTOR. The Kd values with PIKFYVE for all five molecules ranged from 1 nM (compound 1) to 16 nM (compound 3), and the binding of all five molecules to PIKFYVE was ~300 times greater than to PIP4K2C and ~7000 times greater than to MTOR. Therefore, of 468 human kinases, the entire compounds of the invention bound specifically to PIKFYVE, with compound 1 as the most potent member, and compound 4 the most specific.

Figure 15A:
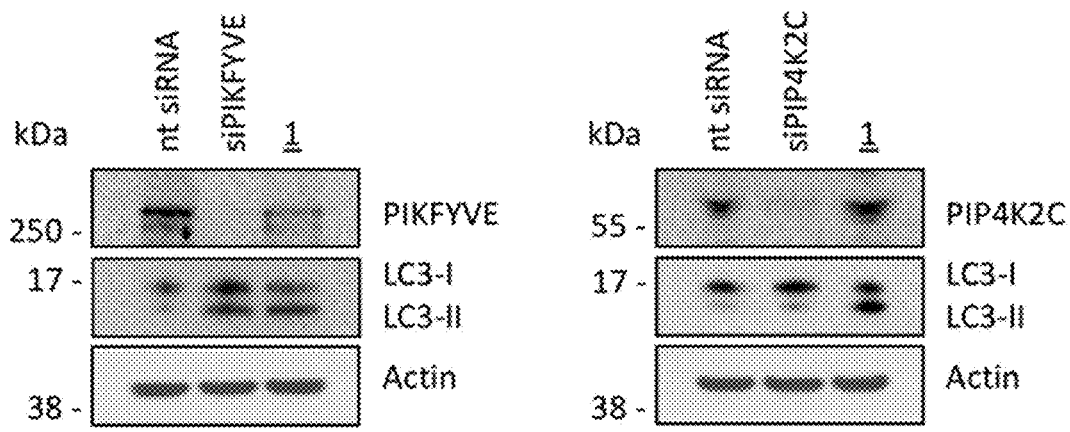
FIG. 15A shows that suppression of PIKFYVE expression induces accumulation of LC3-II, whereas suppression of PIP4K2C expression does not. Western Immunoblots are shown of U2OS cells that were cultured overnight, and then transfected for 7 hrs with 50 pmol siRNA targeted against either PIKFYVE or PIP4K2C mRNA according to the manufacturer's instructions. Cells were then cultured for 36 hrs, and then total cell extracts were subjected to Western immuno-blotting. As a control, cells were also cultured in the presence of 0.1 µM compound 1 for the same length of time.
Figure 15B:
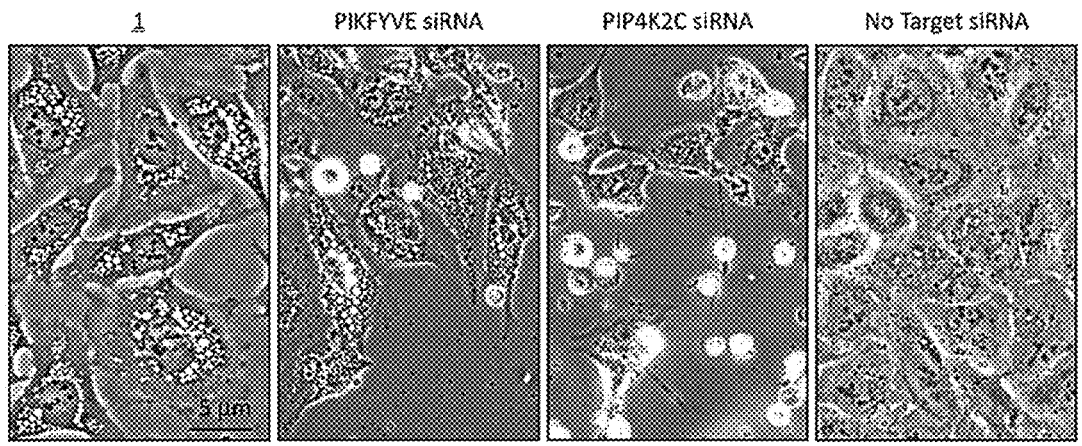
FIG. 15B shows that suppression of PIKFYVE expression induces accumulation of cytoplasmic vacuoles, whereas suppression of PIP4K2C expression does not. Images from phase contrast microscopy (40×) of the cells in FIG. 15A reveal the extent of cytoplasmic vacuolization. Therefore, the biological effects of compounds of the invention were not due to inhibition of PIP4K2C.

To determine which kinase was responsible for the effects of compound 1, U2OS cells were treated with siRNAs targeting either PIKFYVE or PIP4K2C. Although expression of both PIKFYVE and PIP4K2C were strongly suppressed, only siRNAs against PIKFYVE were equivalent to compound 1 at promoting LC3-II accumulation (FIG. 15A), and inducing cytoplasmic vacuolization (FIG. 15B). In fact, siPIP4K2C caused U2OS cells to detach from the plate and shrink in size. Those cells that remained attached contained no more vacuoles than observed using 'no target' siRNA.

Figure 15C:
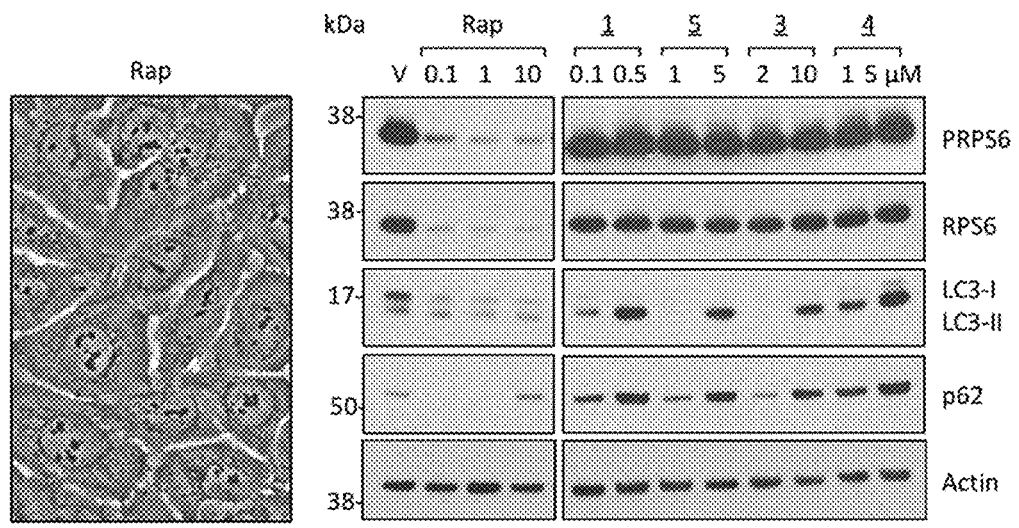
FIG. 15C shows that the biological effects of compounds of the invention were not due to inhibition of MTOR. U2OS cells were cultured for 24 hrs in the presence of vehicle (V), or the indicated concentrations of either rapamycin (Rap), or compounds 1, 3, 4, or 5. Rapamycin is a specific inhibitor of MTOR. Whole cell extracts were then subjected to western immuno-blotting for LC3, p62, ribosomal protein S6 (RPS6) and its phosphorylated form (PRPS6). β-Actin was included as a loading control. The positions of molecular mass markers are indicated (kDa). The MTOR signal transduction pathway activates the protein kinase RPS6KB1, which phosphorylates RPS6 protein and suppresses translation of the RPS6 gene. As expected, rapamycin inhibited expression of both RPS6 and phosphorylated RPS6 (PRPS6), thereby confirming that rapamycin inhibited MTOR activity. However, rapamycin did not induce cytoplasmic vacuolization, LC3-II expression, or p62 expression, thereby confirming that rapamycin was not the target of compounds of the invention.

Treatment of U2OS cells with rapamycin, a specific inhibitor of MTOR activity (56), also did not induce vacuolization (FIG. 15C), and it did not cause cells to detach and die, although it did inhibit their proliferation. Moreover, compounds of the invention did not inhibit MTOR activity. The MTOR signal transduction pathway activates the protein kinase RPS6KB1, which phosphorylates RPS6 protein and suppresses translation of the RPS6 gene (57). As expected, rapamycin inhibited expression of both RPS6 and phosphorylated RPS6 (PRPS6) (FIG. 15C). In contrast, none of the compounds of the invention affected the levels of either RPS6 or PRPS6, whereas they did induce accumulation of LC3-II and p62. Therefore, the compounds of the invention did not inhibit MTOR activity. Taken together, these results demonstrated that the compounds of the invention primarily, if not exclusively, disrupted lysosome homeostasis by inhibiting PIKFYVE activity.

The Compounds of the Invention Selectively Killed Autophagy-Dependent Cancer Cells The multiple disruptions of lysosome homeostasis induced by the compounds of the invention suggested that these-compounds would inhibit proliferation or viability of autophagy-dependent cells. To test this hypothesis, the effects of compound 1 on the vacuolization, proliferation and viability of melanoma A375 cells were compared with the effects of the lysosomal inhibitors hydroxychloroquine (HCQ) and chloroquine (CQ). Melanoma A375 cells are homozygous for the Braf$^{V600E}$ mutation and have been termed 'autophagy-addicted', because ablation of genes essential for autophagy in models of Braf$^{V600E}$-driven cancer impairs mitochondrial metabolism and increases the survival of Braf$^{600E}$ tumor-bearing mice (7, 58). Consequently, A375 cells require autophagy for cell growth, proliferation, and viability even when cultured in a rich medium, as evidenced by its sensitivity to hydroxychloroquine (HCQ) and chloroquine (CQ) (59).

Figure 16A:
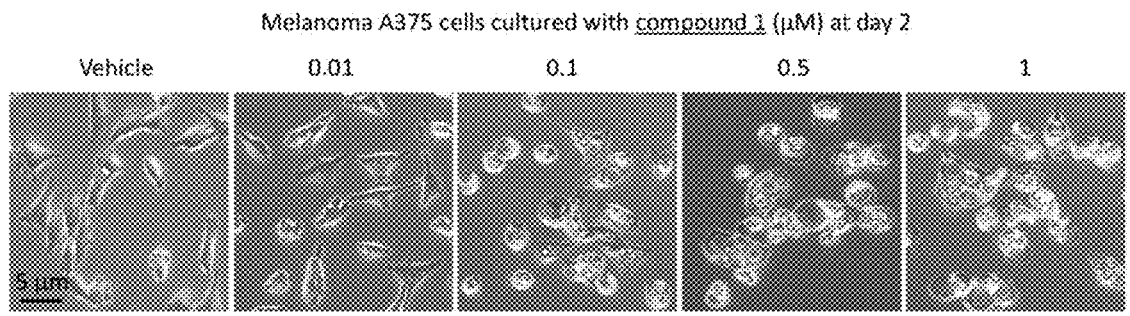
FIG. 16A-D show that compounds of the invention killed autophagy-dependent cells. Human melanoma A375 cells were seeded into 12-well plates (1,000 cells/well) and cultured for 1-day before adding compound 1, hydroxychloroquine (HCQ), or chloroquine (CQ) to give the concentrations indicated.
Figure 16B:
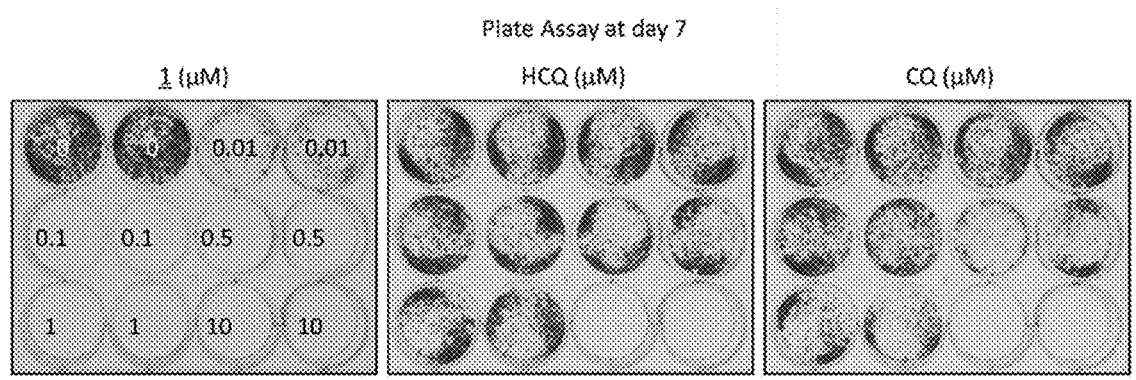
Figure 16C:
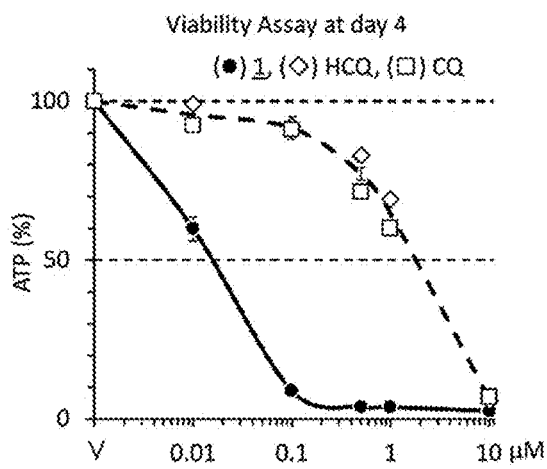
Figure 16D:
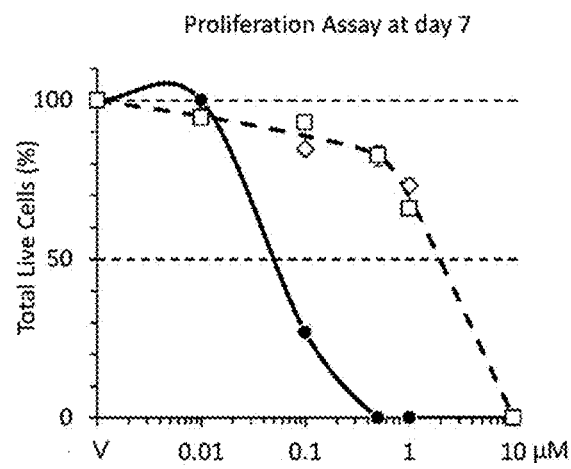
Figure 19A:
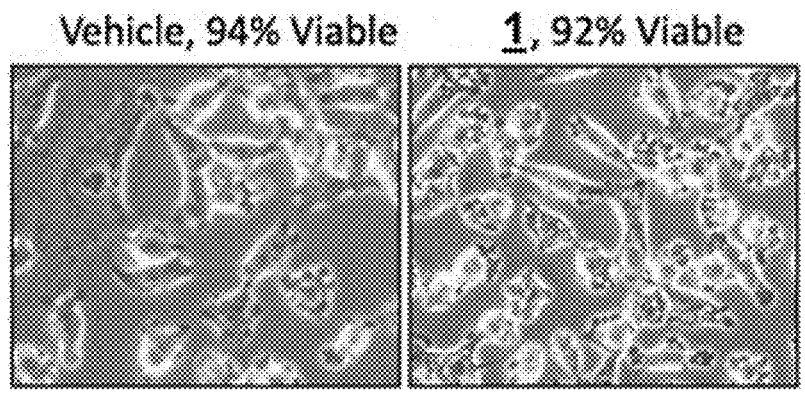
FIG. 19A-D show that compounds of the invention display anti-melanoma tumor activity.
Figure 19B:
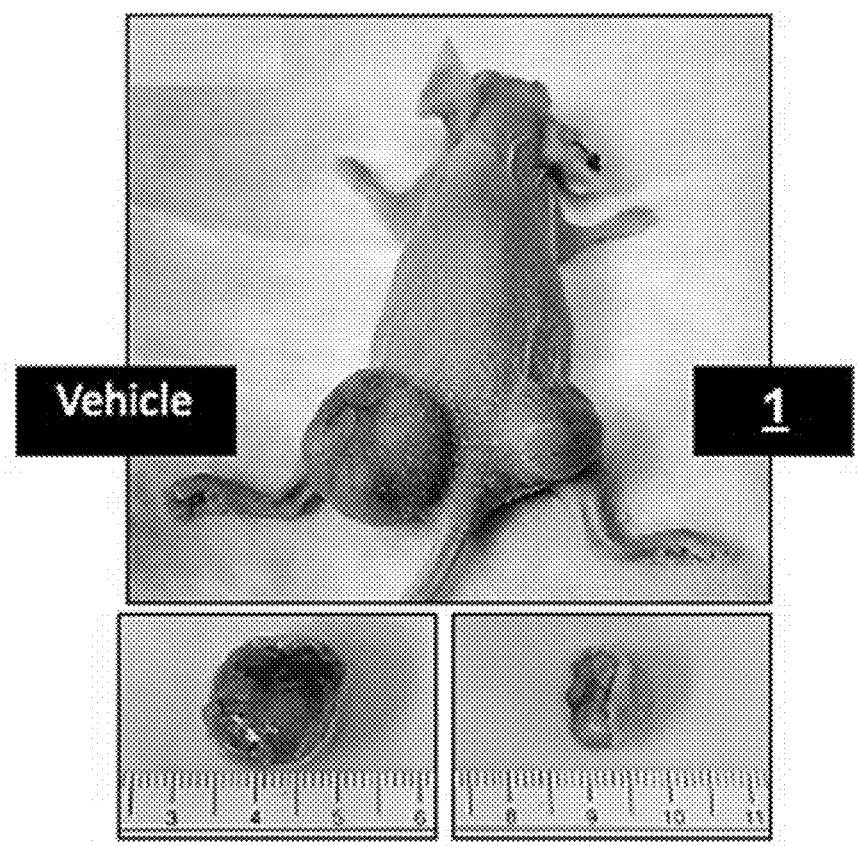
Figure 19C:
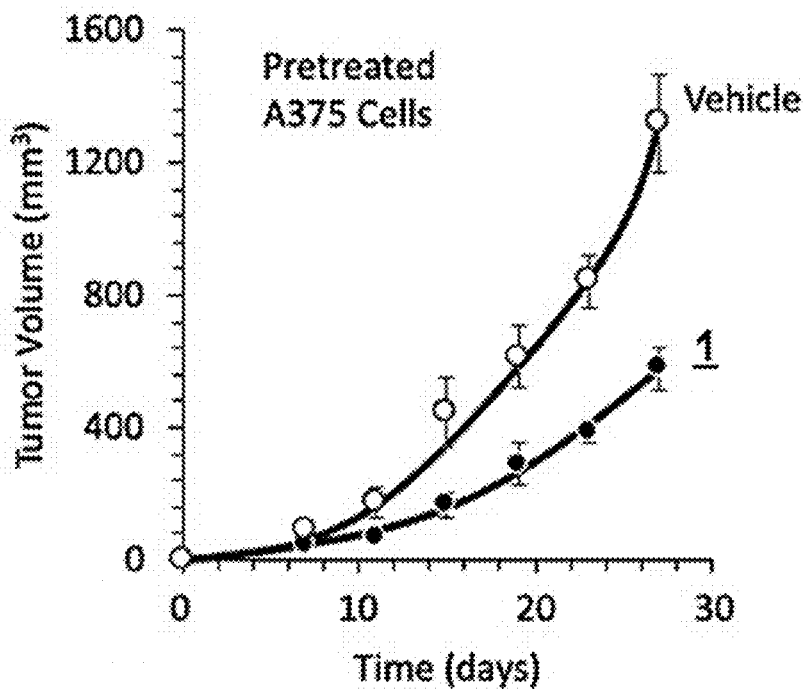

Cells were seeded at a low density (250 cells/cm$^2$) to insure multiple rounds of proliferation. As expected, compound 1 induced extensive cytoplasmic vacuolization in A375 cells (FIG. 16A), an event not observed with either HCQ or CQ. However, all three compounds inhibited A375 cell proliferation, as evident from plate assays (FIG. 16B), although compound 1 was at least 100-times more effective than either HCQ or CQ. Moreover, compound 1 was at least 100-times more lethal than either HCQ or CQ, as evident from the release of cells into the medium within two days (FIG. 16A), the loss of cellular ATP within four days (FIG. 16C), and the loss live cells within seven days, as identified by staining with trypan blue (FIG. 16D). These results confirmed that melanoma A375 cell viability not only required functional lysosomes, but it was exquisitely sensitive to compounds that disrupted multiple events in lysosome homeostasis. The viability of melanoma A375 cells was at least 300 times more sensitive to compounds of the invention than to HCQ. Similar results were obtained with Melanoma M321 cells (data not presented), both of which are homozygous for the BRAF(V600E) mutation. Although compounds of invention show the appearance of vacuoles in normal Human Foreskin Fibroblast (HFF) cells when compared to CQ and HCQ, it was resistant to compound 1 mediated cell inhibition (FIG. 17). As expected, compound 1 inhibited the ability of melanoma A375 cells to produce a tumor in immuno-compromised mice (FIG. 19B).

The osteosarcoma U2OS cells used to characterize compounds of the invention in this study do not harbor a Braf or Kras mutation (60), and they have not been reported to be autophagy-dependent. Nevertheless, HCQ and CQ inhibited U2OS cell growth and proliferation as well as viability without inducing vacuolization, and compound 1 was 21-times more effective than either HCQ or CQ at inhibiting U2OS cell proliferation, and 13-times more effective at reducing viability. Similar results were obtained with colon carcinoma cells and melanoma cells that are not homozygous for the BRAF(V600E) mutation (FIG. 18).

Figure 17A:
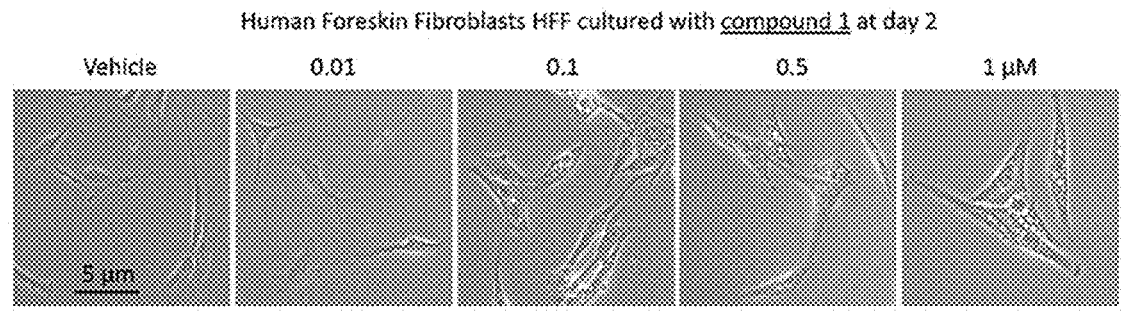
FIG. 17A-C show that compounds of the invention neither inhibited proliferation nor reduced viability of cells that were not autophagy-dependent. In comparison to melanoma A375 cells, human foreskin fibroblasts HFF cells were insensitive to inhibition of either proliferation or viability compound 1, Hydroxychloroquine (HCQ), or Chloroquine (CQ), as assayed in FIG. 17A.
Figure 17B:
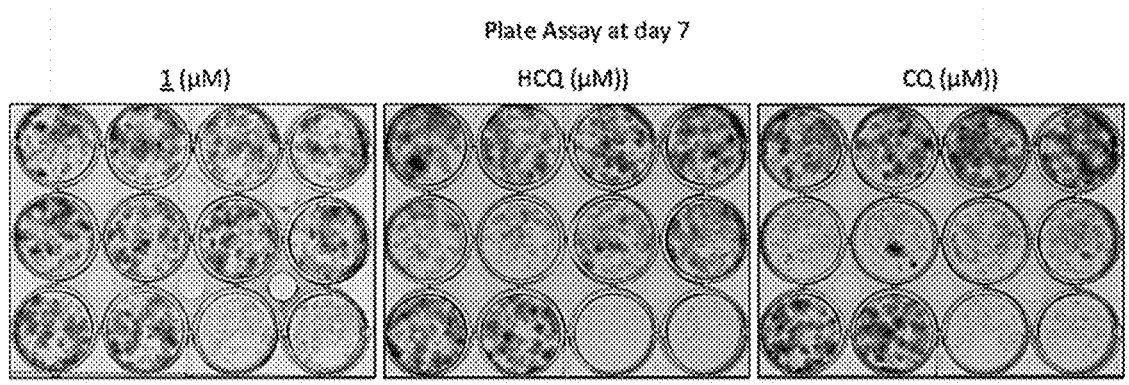
Figure 17C:
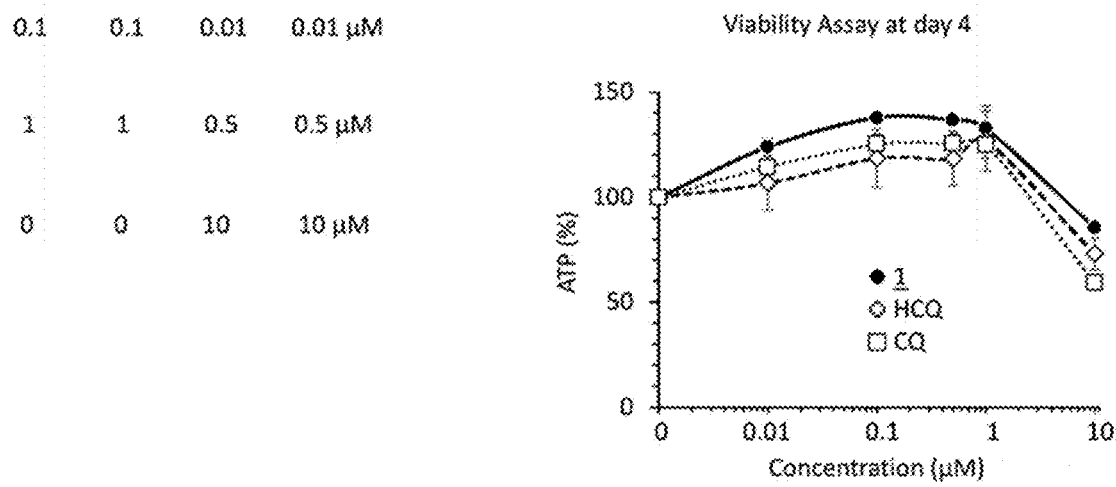
Figure 19D:
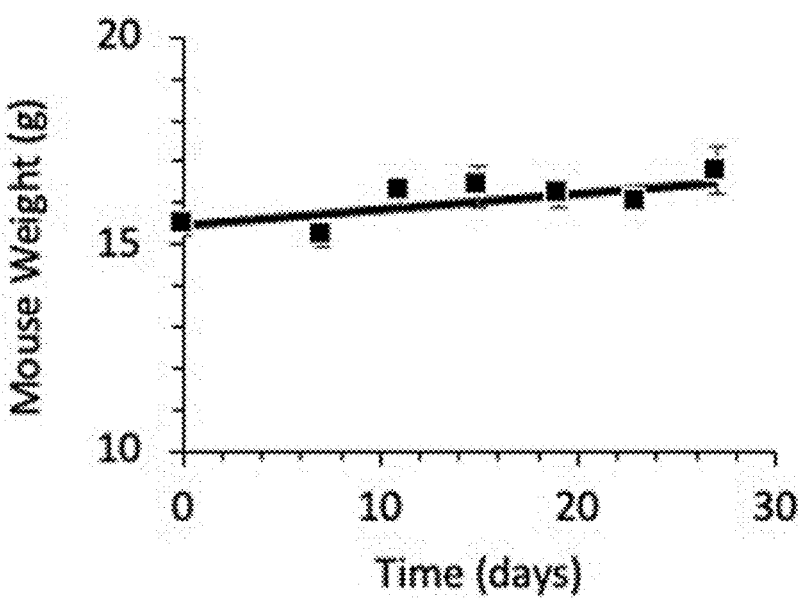
Figure 20A:
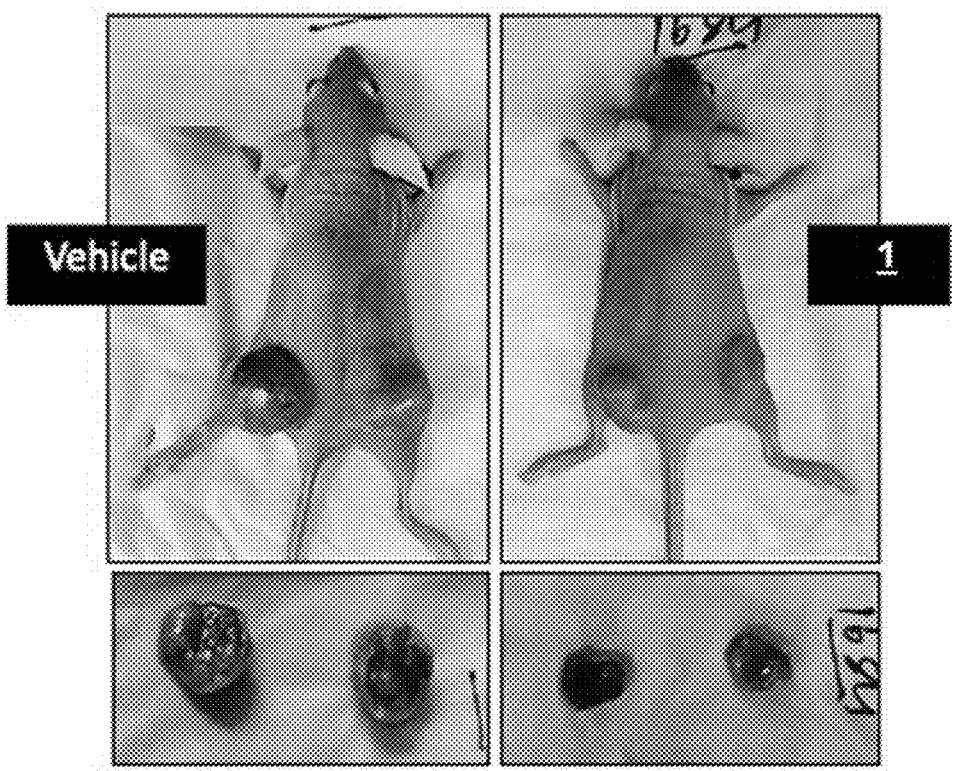
FIG. 20A-C show that compound 1 inhibited expansion of a preformed tumor that arose from cancer cells. (A) Melanoma A375 cells were cultured to 80% confluency and then inoculated subcutaneously into both flanks of inbred nude mice. Palpable tumors (~40-50 mm$^3$) appeared within 7 days. (B) Either vehicle or 20 or 40 mg of compound 1 per kg of the mouse was injected intraperitoneally each day for a period of 14 days. Compound 1 was dissolved in sunflower seed oil. Tumors were excised on day 21. Images of vehicle and compound 1-treated mice are shown in FIG. 20A.
Figure 20B:
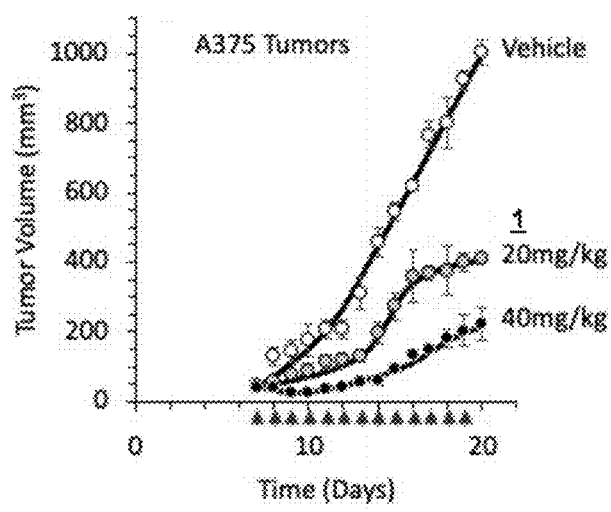

In contrast to autophagy-dependent cancer cell lines, the $EC_{50}$ values for compound 1, HCQ, or CQ on human foreskin fibroblasts were all greater than 10 μM (FIG. 17A-C). This was also true for embryonic kidney cells and breast adenocarcinoma cells (FIG. 18). Thus, although sub-micromolar levels of compound 1 induced comparable levels of vacuolization in all of the cell lines tested, autophagy-dependent cancer cells, such as melanoma A375 cells, were as much as 1000× more sensitive to compound 1 than were non-malignant human cells, thereby providing proof-of-principle that the compounds of the invention have therapeutic potential in the treatment of autophagy-dependent cancers. In fact pretreatment of melanoma A375 cells with the 10 uM of compound 1 for 8 hrs regressed the tumor formation in immunocopromised mice (FIG. 19A-D). Intraperitoneal administration of increase amount of compound 1 (i.e. 20 and 40 mg/kg wt) both in inbreed and outbreed immunocompromised mice with a predeveloped tumor (40-50 mm), everyday for a period of 14 days was observed to reduce the tumor growth progression drastically without any ill effects on mice (FIG. 20-22). This study corroborate the previously described in vitro growth inhibitory property of compound 1 against cancer cells and further strengthen its use as an anticancer agent either alone or in combination with other chemotherapeutic compounds.

Summary & Discussion

These Compounds Selectively Inhibit the PIKFYVE Phosphoinositide Kinase

PIKFYVE is a lipid kinase targeted to the cytoplasmic face of endosomal membranes via interactions between the FYVE domain and phosphatidylinositol-3-phosphate (PI3P). PIKFYVE phosphorylates PI3P to generate phosphatidylinositol 3,5-biphosphate ($PI(3,5)P_2$), and plays a crucial role in the regulation of endosome trafficking (61, 63). Screening a panel of 468 human kinases against 10 μM compound 1 identified PIKFYVE as the primary target. Subsequent determination of the dissociation constant for each of the compounds of the invention revealed that PIKFYVE was the only high-affinity target among this group. The ability of the compounds of the invention to induce accumulation of large cytoplasmic vacuoles was consistent with previous reports of PIKFYVE inhibition by specific chemicals, by siRNA, and by PIKFYVE mutations (47, 62-66). Reduction of the compounds of the invention induced vacuolization in the presence of BafA1, an inhibitor of the vacuolar-ATPase, further confirmed that the compounds of the invention were 'PIKFYVE inhibitors (47).

Two previously reported PIKFYVE inhibitors are members of the compounds of the invention. Vacuolin and compound 1 share in common the 1,3,5-triazin-2-amine core with a morpholine adduct at position 6, and Apilimod and NDF share in common the 3-methylbenzaldehyde (6-morpholin-4-ylpyrimidin-4-yl)hydrazine core. A third PIKFYVE inhibitor, YM201636 is only distantly related to the compounds of the invention in that it shares the 1,3-diazine ring core with a morpholine adduct at position 4; the adducts at position 2 and 5,6 are quite different. As expected, all three of these PIKFYVE inhibitors were effective at inhibiting proliferation of melanoma A375 cells, although they differed in efficacy by 30-fold.

These Compounds Disrupt Lysosome Homeostasis

Previous studies have shown that inhibition of PIKFYVE by either chemical or genetic means results in the accumulation of large cytoplasmic vacuoles, identified in various reports as endosomes (67-69), exosomes (70, 71), lysosomes (63, 72, 73), or autophagosomes (62, 74). Thus, PIKFYVE appeared to play multiple roles in membrane vesicle trafficking. The results presented here show that the presently disclosed family of PIKFYVE inhibitors disrupts three specific events in lysosome homeostasis. (1) They inhibit lysosome fission but not homotypic lysosome fusion, thereby causing accumulation of enlarged lysosomes and preventing lysosome turnover. (2) They impair trafficking of molecules into lysosomes, thereby impairing lysosome function, although they do not decrease lysosome acidity. (3) They prevent heterotypic fusion between lysosomes and autophagosomes, thereby preventing degradation of autophagic cargoes.

With compound 1, vacuoles could be detected by light microscopy in U2OS cells within 20 minutes, accumulation of LC3-II and p62 within 4 hours, and inhibition of cell proliferation within 24 to 48 hours. The vacuoles identified here were subsequently shown to be enlarged lysosomes that did not fuse with autophagosomes. Moreover, they resulted from lysosome fusion in the absence of lysosome fission, and the enlarged lysosomes differed from normal lysosomes in their ability to restrict entry of some molecules, but not others. Thus, lysosome homeostasis was disrupted by these molecules at three specific events: lysosome fission, traffic into lysosomes, and fusion with autophagosomes. All three disruptions were detected with each of the five members of the compounds of the invention, and their relative potencies at inducing formation of large cytoplasmic vacuoles, accumulation of LC3-II and p62, arrest of cell proliferation, and loss of cell viability were compound 1>compound 4>compound 5>compound 3 or compound 2 (FIG. 1C).

These Compounds Selectively Inhibit Lysosome Fission and Heterotypic Lysosome Fusion Lysosome homeostasis depends on continued homotypic lysosome fusion and fission (20). The results presented here show that PIKFYVE is essential for lysosome fission, but not for homotypic lysosome fusion. This finding accounts for the widely reported observation that inhibition of PIKFYVE resulted in the accumulation of enlarged cytoplasmic vacuoles. The results presented here further show that PIKFYVE is also essential for fusion between lysosomes and autophagosomes. This result is consistent with previous studies showing that heterotypic lysosome fusion events require a delicate balance between PT3P and PI(3,5)P$_2$ on the lysosomal membrane, a balance that is established by the PIKFYVE phosphoinositide kinase and the inositol polyphosphate-5-phosphatase E (75, 76). Therefore, PIKFYVE is required for direct fusion between lysosomes and autophagosomes. In addition, impaired lysosome fission might exacerbate inhibition of heterotypic fusion events by restricting trafficking between lysosomes and other membrane vesicles.

Inhibition of lysosome fission by compounds of the invention was evident from the fact that LAMP1 synthesis was not disrupted, but the size of LAMP1-labeled vacuoles increased dramatically, with a concurrent decrease in the number of lysosomes (FIG. 2). Live cell imaging revealed that lysosomes fused together in the presence of a compound of the invention to produce enlarged lysosomes (FIG. 3), and then dissolve into masses of puncta when the compound was removed. High resolution live cell imaging revealed individual lysosomes undergoing fission via tubulation upon removal of compound 1 (FIG. 7). Lysosome tubules serve as a platform for lysosome reformation, a process through which membrane lipids and proteins are recycled via membrane fission (77). These results are consistent with a role for phosphatidylinositol-3,5-bisphosphate (the product of PIKFYVE activity) in lysosome tabulation (78).

Figure 3C:
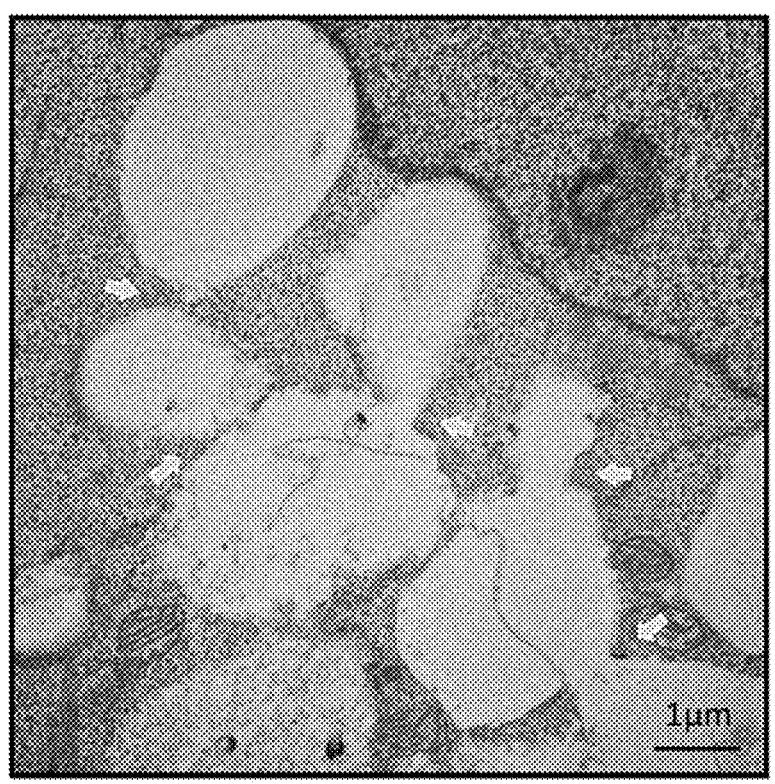
Figure 4A:
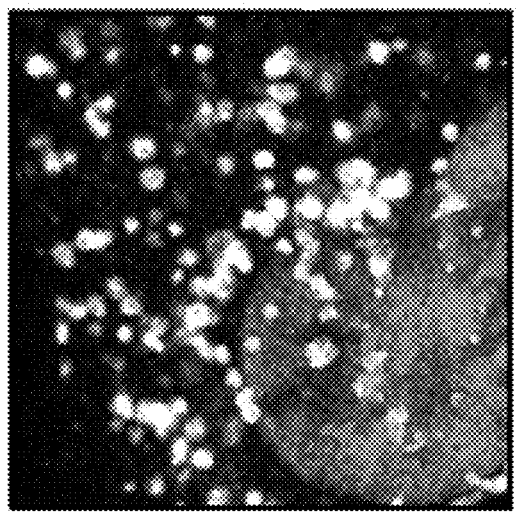
FIG. 4A-D show fluorescent images as viewed by confocal microscopy of HeLa cells that were cultured for 10 min in the presence of either vehicle (FIG. 4A), 10 μM N-ethylmaleimide (NEM) (FIG. 4B), or 1 μM compound 1 (FIG. 4C) before washing them with phosphate buffered saline. Fresh medium was then added containing either vehicle or 1 μM compound 1 (FIG. 4D) and the cells were cultured for 1-hr. Cells were then stained with anti-LAMP1 antibody, a fluorescent-conjugated secondary antibody to identify lysosomes, and DAPI to identify nuclei. Scale bar is 5 μm. Thus, accumulation of enlarged lysosomes requires the NEM sensitive factor required for SNARE complex disassembly and recycling.
Figure 4B:
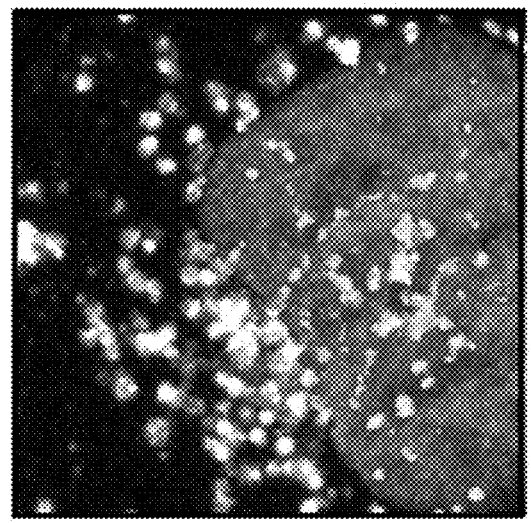
Figure 4C:
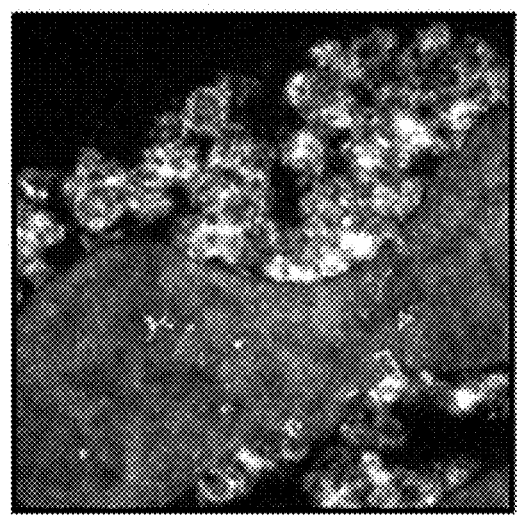
Figure 4D:
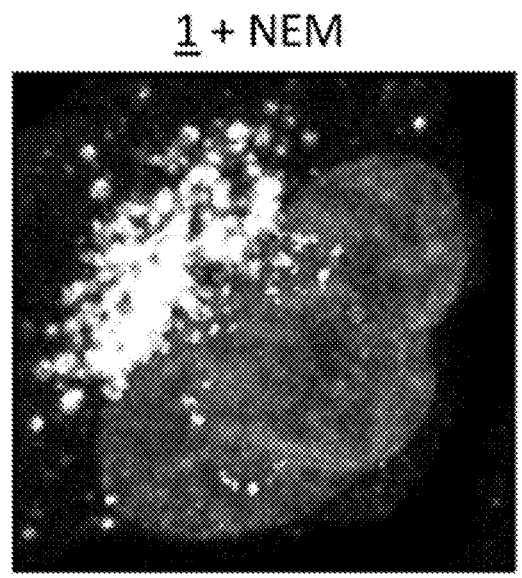
Figure 4E:
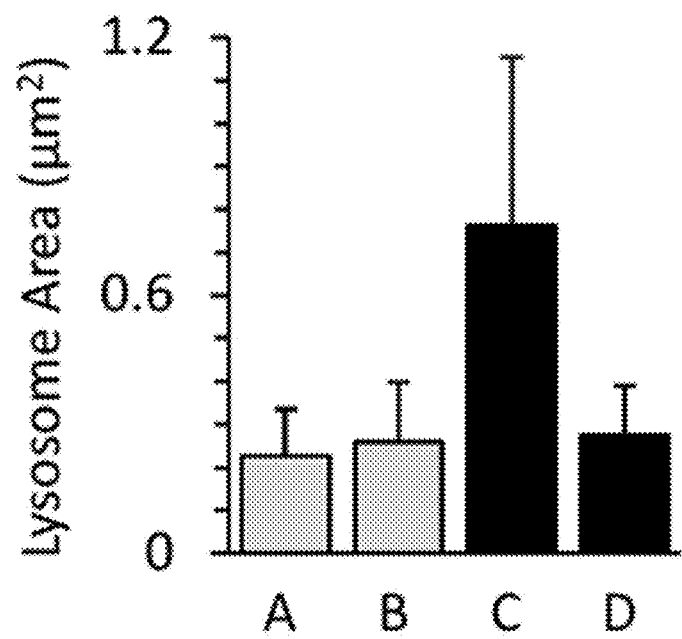
FIG. 4E shows quantitation of lysosome area for FIG. 4A-C.

Inhibition of lysosome fusion to autophagosomes was evident from the fact compounds of the invention rapidly induced accumulation of autophagosomal markers LC3-II and p62 (FIG. 10), and LC3 as cytoplasmic puncta (FIG. 11). Electron microscopy confirmed the accumulation of vesicular structures consistent with early and late stages in autophagy (FIG. 3). Cells transfected with a vector expressing a modified tandem sensor RFP-GFP-tagged LC3B protein in which the green signal from a mutated GFP was suppressed in an acidic environment revealed that autophagosomes did not mature into autolysosomes in the presence of compound 1 (FIG. 12), and cells transfected with both GFP-LC3 and LAMP1-RFP expression vectors revealed that the absence of an acidic environment resulted from failure of lysosomes to fuse with autophagosomes (FIG. 13).

Previous studies have shown that heterotypic lysosome-to-autophagosome fusion requires NSF, the HOPS complex, and the BORC complex (21, 79). The N-ethylmaleimide sensitive factor (NSF) is a AAA ATPase that promotes disassembly of trans-SNARE complexes for reutilization of the SNAREs in further rounds of fusion (80). HOPS is essential to tether the opposing membranes and orchestrate SNARE-dependent fusion, and BORC is required for recruitment of HOPS to lysosomes and for lysosome positioning (81). Each of these components was required for compound 1-induced lysosome enlargement (FIG. 4). These results extended previous studies by showing that lysosomal enlargement required components of the SNARE fusion machinery that are essential for both homotypic and heterotypic lysosome fusion events.

Although PIKFYVE was not essential for homotypic lysosome fusion, PIKFYVE was essential for heterotypic fusion of lysosomes to autophagosomes, and perhaps lysosome-to-endosome fusion, as well (62). However, inhibition of autolysosome formation by the compounds of the invention required about 10-times higher concentrations than required to prevent lysosome fission. Nevertheless, specific inhibition of PIKFYVE by the compounds of the invention still occurred at these concentrations (FIG. 1B) and resulted in the accumulation of LC3-II and p62 (FIG. 10), as previously reported using other methods for PIKFYVE inhibition (62, 64, 82, 85). Furthermore, co-localization of fluorescent-tagged LC3 and p62 proteins in situ confirmed the accumulation of autophagosomes in the absence of autolysosomes (no figure describing colocalization of LC3 and p62 in the figure file). The absence of autolysosomes was further demonstrated by the accumulation of a tandem RFP-GFP-LC3B protein in which the pH sensitive GFP remained unquenched, thereby confirming a nonacidic environment, and by the fact that LC3-labeled puncta did not co-localize with LAMP1-labeled enlarged lysosomes (FIG. 13). Similar results have also been reported for Vacuolin.

These Compounds Impaired Lysosomal Trafficking

Previous studies on the importance of PIKFYVE in maintaining lysosomal acidity resulted in apparently contradictory conclusions. Some studies concluded that PIKFYVE was not essential to maintain lysosomal acidity either in yeast or in RAW264.7 cells, a macrophage-like mouse cell line, whereas other studies concluded that PIKFYVE was required to maintain lysosome acidification in rat neuronal dendrites, mouse fibroblasts and human HeLa cervical adenocarcinoma cells. These studies, however, not only utilized cells from different species, but different PIKFYVE inhibitors and different methods of analyses. For example, analysis of lysosomal pH in HeLa cells using both a ratiometric method and LysoSensor concluded that Vacuolin-1 reduced lysosomal acidity from pH 4.8 to pH5.3.

In the present study, a ratiometric analysis of lysosomes preloaded with Oregon Green Dextran revealed that inhibition of PIKFYVE with either compound 1 did not result in deacidification of lysosomes in human U2OS osteosarcoma cells (FIG. 8A). These results were consistent with the fact that LysoTracker stained all of the lysosomes in compound 1-treated U2OS cells, although to varying extents (FIG. 8B). Therefore, inhibition of PIKFYVE, as confirmed by the rapid accumulation of enlarged lysosomes, did not cause lysosome deacidification. However, it did impair trafficking of molecules into lysosomes.

The ratiometric method revealed a mean pH of 5.3 for lysosomes in untreated U2OS cells and 5.0 for lysosomes in compound 1 treated U2OS cells (FIG. 8). Therefore, LysoSensor, with a pKa of 5.2, should have stained lysosomes under both conditions. Similarly, BODIPY-Pepstatin-A, which binds specifically to mature cathepsin D at acidic pH, should also have stained both untreated and treated cells. The fact that both of these agents stained lysosomes only in untreated cells strongly suggests that their ability to enter the enlarged lysosomes of treated cells was impaired.

This conclusion was confirmed in two ways. First, Acridine Orange stained lysosomes in untreated U2OS cells, and it stained a few of the smaller lysosomes in compound 1 treated cells. However, most of the enlarged lysosomes in compound 1 treated cells were neither red nor green; they were empty of dye (FIG. 9C). In contrast, analysis of autophagy using the red-to-green fluorescence intensity ratio from Acridine Orange measured with accuracy the increase in autophagy induced by starvation or rapamycin, and the reduction in autophagy produced by BafA1 or depletion of Beclin1 or ATG7 without encountering 'black holes'. Second, the fraction of mature cathepsin D was reduced in U2OS cells treated with compound 1 (FIG. 9B). Taken together, these results reveal that lysosomes in both U2OS and RAW cells treated with PIKFYVE inhibitors are dysfunctional, not because they are no longer acidic, but because traffic into these vesicles is impaired. Given the facts that the efficacy of the PIKFYVE inhibitors disclosed herein varied at least 400-fold (FIG. 1B), that their efficacy was time and concentration dependent and reversible, and that the sensitivity of different human cell lines to compound 1 varied as much as 1000-fold (FIG. 18), it would be surprising if the effects of PIKFYVE inhibition were not sensitive to experimental conditions.

Although the mechanism by which PIKFYVE inhibitors impair the ability of molecules to enter lysosomes is unknown, it does not involve inhibiting V-ATPase, because BafA1 (a specific inhibitor of V-ATPase activity) prevents lysosome acidification without inducing lysosomal enlargement. In yeast, vacuole fusion requires the physical presence of V-ATPase, but not its pump activity, whereas fission requires V-ATPase activity. If the same were true in mammals, BafA1 would have been expected to cause lysosomal enlargement. The fact that BafA1 prevented the compounds of the invention from inducing lysosomal enlargement (FIG. 9A) confirmed that V-ATPase is required for lysosomal enlargement when PIKFYVE activity is suppressed and suggests that V-ATPase is required for homotypic lysosome fusion. In *Drosophila*, however, lysosomal acidification is not a prerequisite for heterotypic lysosome fusion, because V-ATPase-deficient lysosomes can fuse with autophagosomes and endosomes. BafA1 prevents autophagosome-lysosome fusion in *Drosophila* cells by depletion of the calcium ion pump SERCA, a secondary target of BafA1.

These Compounds Exhibit Therapeutic Potential Against Autophagy-Dependent Cancer Cells Activation and inhibition of autophagy are of significant interest as potential therapeutic approaches to infection, inflammation, immunity, and neurodegenerative diseases (Walter, C. et al., Neuropharmacology 108:24-38 (2016); Deretic, V. et al., Nat Rev Immunol 13:722-37 (2013)). However, the role of autophagy in cancer remains paradoxical. In non-malignant cells, autophagy promotes genomic stability by maintaining homeostasis, thereby suppressing cancer, but in malignant cells, autophagy promotes cancer by allowing them to proliferate and migrate under conditions where normal cells become quiescent [reviewed in Kimmelman 2017; Nyfeler 2016; Mainz 2017; Mowers 2017]. Therefore, systemic disruption of autophagy by experimental gene ablation or naturally occurring gene mutations can lead to cancer (Mathew 2009; Degenhardt 2006; Liu 2015; Karantza-Wadsworth 2007), whereas pharmacologic inhibition of autophagy in humans with either hydroxychloroquine or chloroquine, alone or in combination with chemotherapy, causes tumor shrinkage [reviewed in Levy 2017; Chude CI 2017].

Disclosed herein is a method of treating autophagy-dependent human cancers. The ability of the inventive family of PIKFYVE inhibitors to effectively disrupt multiple events in lysosome homeostasis presumably accounts for the fact that compound 1 was at least 300× more effective at killing autophagy-addicted melanoma cells than the lysosome deacidifiers HCQ and CQ, two drugs currently used in clinical trials to disrupt autophagy by inhibiting the ability of lysosomes to degrade proteins. Moreover, compound 1 inhibited tumor formation of autophagy-addicted cancer cells in xenografts. Compound 1 was still 20× more effective than HCQ and CQ at arresting the growth and proliferation of cancer cells that depend on autophagy, but that are not addicted. Non-malignant human cells were unaffected by compound 1 at concentrations 1000× greater than required to kill autophagy-addicted cells. These results suggest that the multiple disruptions in lysosome homeostasis induced by compound 1 provide enhanced therapeutic potential over drugs that disrupt autophagy at a single event. The fact that concentrations of compound 1 that could arrest or kill autophagy-dependent cancer cells had little, if any, effect on cell proliferation or viability of nonmalignant cells strongly support further investigation into the application of PIKFYVE inhibitors in cancer chemotherapy.

Submicromolar concentrations of the inventive compounds inhibited autophagy-dependent cells such as melanoma A375 and osteosarcoma U2OS in proportion to their efficacy at disrupting autophagy. In the presence of 0.1 $\mu$M compound 1, cytoplasmic vacuolization reduced the proliferation rate of U2OS cells, but killed Melanoma A375 cells. Compound 1 also inhibited melanoma A375 cells from producing a tumor xenograft. In contrast, autophagy-independent cells such as foreskin fibroblasts and embryonic kidney cells were resistant to micromolar concentrations of the inventive compounds. These results provide proof that the inventive compounds are therapeutically useful.

Treatment of Mice with Compound 1 Inhibited Melanoma Tumor Formation and Progression To determine whether or not compound 1 could inhibit progression of a tumor that arose from autophagy-dependent cancer cells, melanoma A375 cells were pretreated with either vehicle or compound 1 and then assayed for their ability to produce a tumor. Pretreatment consisted of culturing A375 cells for 8 hours with 10 $\mu$M compound 1. The cells were then recovered by trypsinization and their viability confirmed by trypan blue exclusion. Cells treated with vehicle were 94% viable and displayed no cytoplasmic vacuolation, whereas cells treated with compound 1 were 92% viable and displayed cytoplasmic vacuolation (FIG. 19A). The cells were then inoculated subcutaneously into the flanks of immuno-compromised mice. Both sets of pretreated cells formed tumor xenografts, but those pretreated with compound 1 were decidedly less efficient (FIG. 19B,C). The mice exhibited no ill effects (FIG. 19D). These results demonstrated that if compound 1 inhibited PIKFYVE, as evidenced by cytoplasmic vacuolation, then tumor formation was inhibited.

Figure 20C:
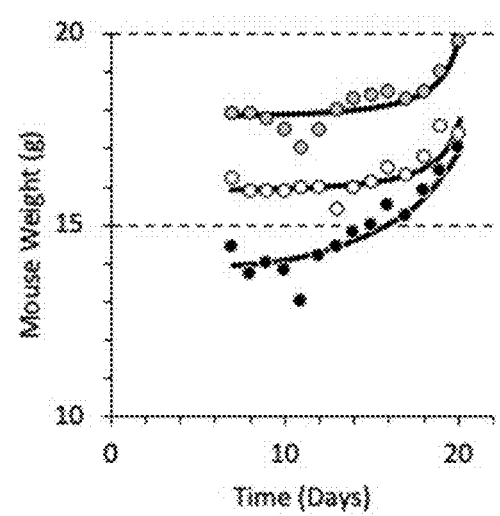

To determine whether or not compound 1 could inhibit expansion of a preformed tumor that arose from autophagy-dependent cancer cells, melanoma A375 cells were inoculated into the flanks of immuno-compromised mice and allowed to form a palpable tumor. Mice were then injected intraperitoneally once a day with varying amount of compound 1. The results demonstrated that expansion of preformed tumors was inhibited by compound 1 in a dose dependent manner (FIG. 20A,B). The mice exhibited no ill effects (FIG. 20C).

Figure 21A:
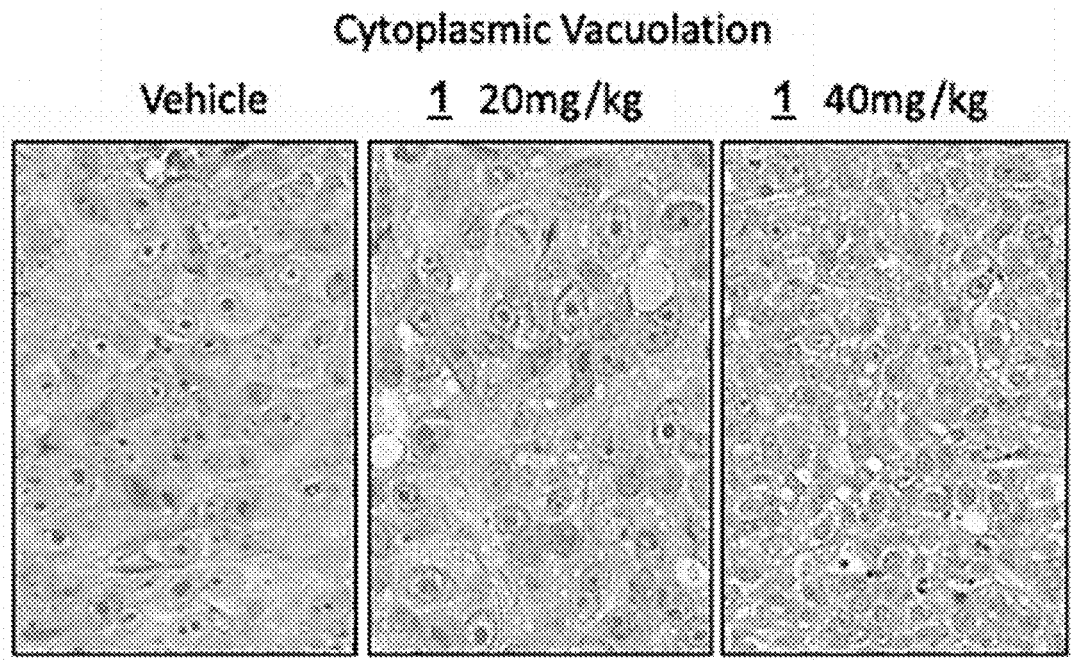
FIG. 21A shows photomicrographs of slices from tumors taken from mice that were stained with hematoxylin and eosin to visualize cellular structure. Cytoplasmic vacuolation was clear in tumors from compound 1-treated mice, and the extent of vacuolation was clearly greater at with greater concentrations of compound 1.
Figure 21B:
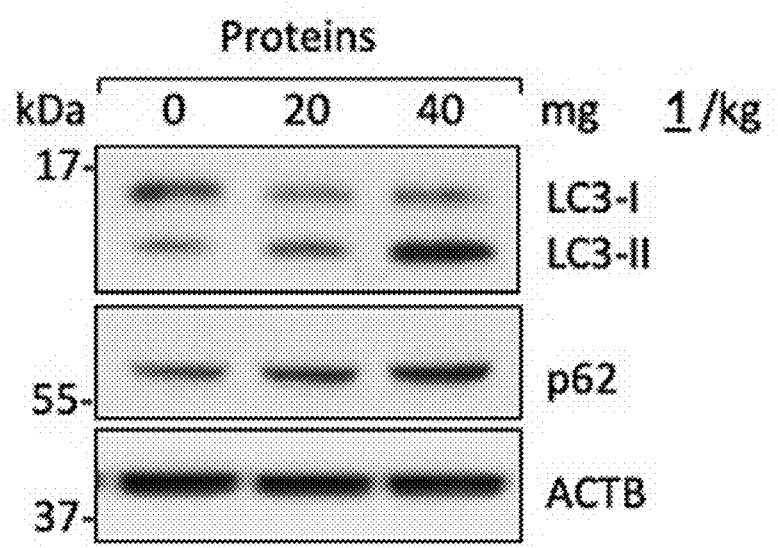
FIG. 21B shows that compound 1 also had disrupted autophagy within tumor, as evidenced by an increased in the relative amounts of LC3-II and p62 proteins in tumor lysate. β-actin was the loading control.
Figure 22A:
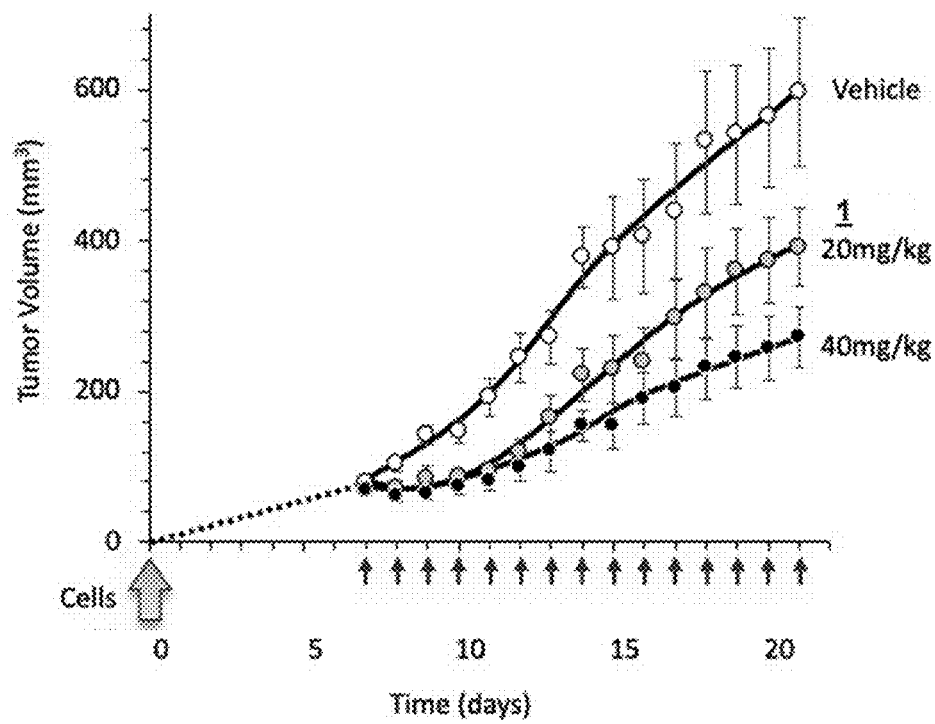
FIG. 22A shows that compound 1 inhibited growth of tumors in outbred nude mice. Melanoma A375 cells were inoculated subcutaneously into outbred nude mice on day 0 (broad arrow). Intraperitoneal injections (arrows) of vehicle (open circles), 20 mg compound 1 (grey circles), or 40 mg compound 1/kg (solid circle) of mouse weight were administered daily beginning with day 7 when palpable tumors were present. Each group contained three mice. SEMs are indicated. Mice were weighted each day during injections and the results shown in FIG. 22B. Error bars indicate the SEM for 6 tumors.

To determine whether or not compound 1 injected intraperitoneally was active within the tumor, tumor slices were stained with hematoxylin and eosin to visualize cellular structure. Cytoplasmic vacuolation was clearly evident in tumors from compound 1 treated mice, and the extent of vacuolation was clearly greater at higher concentrations of compound 1 (FIG. 21A). Compound 1 had also disrupted autophagy, as evidenced by increased levels of LC3-H and p62 proteins in tumor lystaes (FIG. 21B).

Figure 22B:
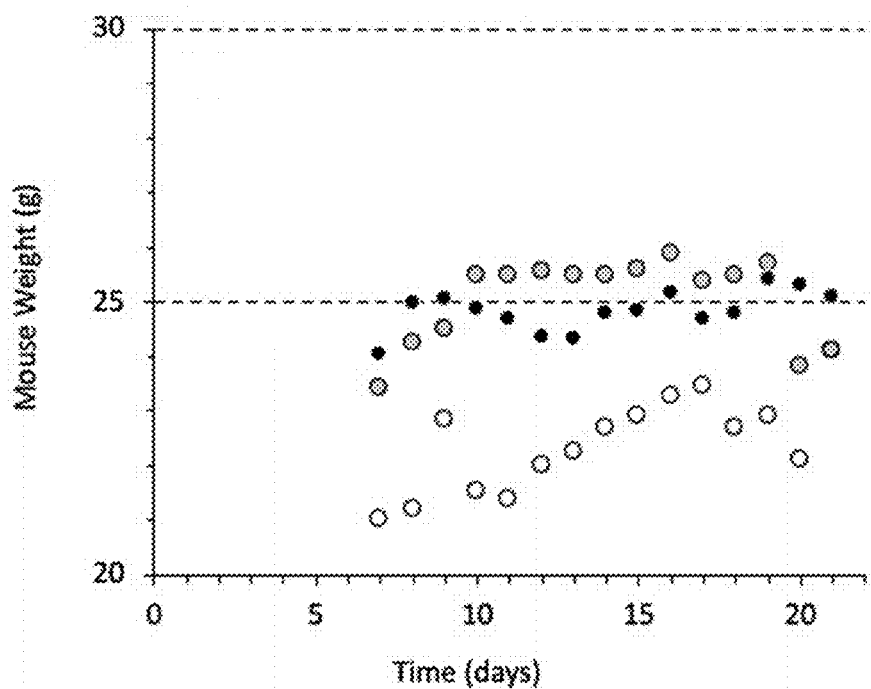

The genetic diversity of human populations is greater than the genetic diversity of inbred animals. Therefore, the experiment in FIG. 20 with inbred nude mice was repeated with outbred nude mice. The results were essentially the same; expansion of preformed tumors was inhibited by compound 1 in a dose dependent manner (FIG. 22A) with no visible ill effects to the mice (FIG. 22B). However, as expected, the response to compound 1 in outbred mice exhibited greater mouse to mouse variation in tumor than observed with inbred nude mice.

The invention can be characterized by the following embodiments.

EMBODIMENTS

1. A method for treating cancer in a mammal, comprising administering to a mammal in need thereof a compound or salt of the formula:

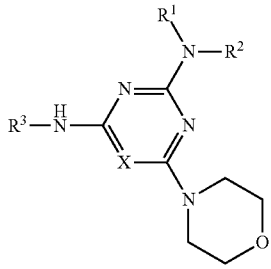

wherein $R^1$ and $R^2$ are independently H, optionally substituted $C_1$-$C_6$ alkyl, or optionally substituted $C_6$-$C_{10}$ aryl, or wherein $R^1$ and $R^2$, taken together with the N to which they are attached, form a 5- or 6-membered heterocyclyl ring, $R^3$ is optionally substituted $C_6$-$C_{10}$ aryl or a group of the formula: $R^4CH=N—$ wherein $R^4$ is $C_6$-$C_{10}$ aryl, heteroaryl, or fused bicyclic heteroaryl, X is CH or N, or a tautomer thereof, or a pharmaceutically acceptable salt thereof, wherein the cancer is an autophagy-dependent cancer, in an amount sufficient to induce autophagy in the cell and cause the death of cancer cells.

2. The method of embodiment 1, wherein X is N.

3. The method of embodiment 1 or 2, wherein $R^1$ and $R^2$, taken together with the N to which they are attached, form morpholinyl, and $R^3$ is optionally substituted $C_6$-$C_{10}$ aryl.

4. The method of embodiment 3, wherein the compound is:

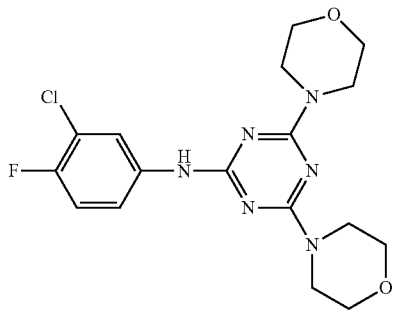

or

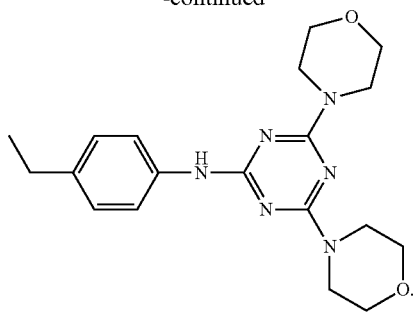

5. The method of embodiment 1 or 2, wherein $R^3$ is $R^4CH=N—$, $R^1$ is H, and $R^2$ is optionally substituted $C_6$-$C_{10}$ aryl.

6. The method of embodiment 5, wherein the compound is:

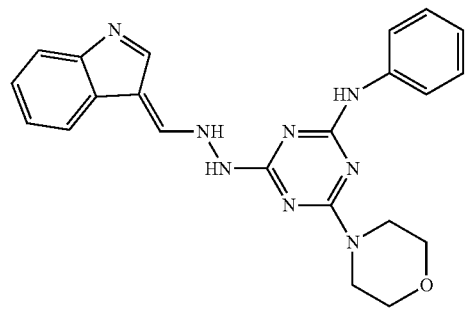

7. The method of embodiment 1, wherein X is CH.

8. The method of embodiment 7, wherein $R^3$ is $R^4CH=N—$ and wherein $R^1$ and $R^2$, taken together with the N to which they are attached, form morpholinyl.

9. The method of embodiment 8, wherein the compound is:

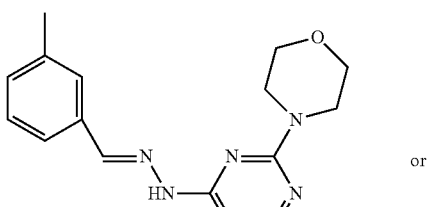

or

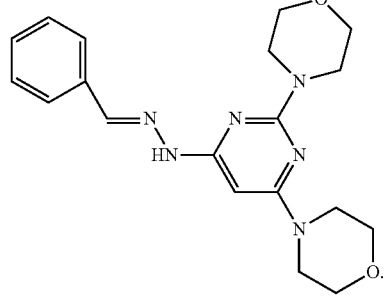

10. The method of any one of embodiments 1-10, wherein the cancer is a malignant, metastatic cancer.

11. The method of any one of embodiments 1-10, wherein the cancer is breast cancer, malignant melanoma, colorectal carcinoma, thyroid papillary carcinoma, glioma, ovarian serous carcinoma, lung adenocarcinoma, or hairy cell leukemia.

12. The method of any one of embodiments 1-11, wherein the cancer comprises cells having a BRAF$^{V600E}$ mutation.

13. The method of any one of embodiments 1-12, wherein the method further comprises administering an additional anti-cancer agent to the mammal.

14. A method for selectively killing cancer cells in a patient afflicted with cancer, comprising administering to the mammal a compound or salt of the formula:

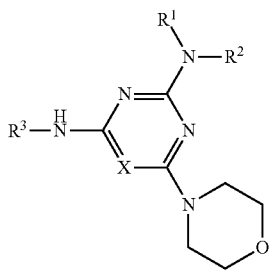

wherein $R^1$ and $R^2$ are independently H, optionally substituted $C_1$-$C_6$ alkyl, or optionally substituted $C_6$-$C_{10}$ aryl, or wherein $R^1$ and $R^2$, taken together with the N to which they are attached, form a 5- or 6-membered heterocyclyl ring, $R^3$ is optionally substituted $C_6$-$C_{10}$ aryl or a group of the formula: $R^4CH=N$— wherein $R^4$ is $C_6$-$C_{10}$ aryl, heteroaryl, or fused bicyclic heteroaryl, X is CH or N, or a tautomer thereof, or a pharmaceutically acceptable salt thereof, wherein the cancer cells are autophagy-dependent cancer cells, in an amount sufficient to induce autophagy in the cells and cause the death of the cancer cells.

15. The method of embodiment 14, wherein X is N.

16. The method of embodiment 14 or 15, wherein $R^1$ and $R^2$, taken together with the N to which they are attached, form morpholinyl, and $R^3$ is optionally substituted $C_6$-$C_{10}$ aryl.

17. The method of embodiment 16, wherein the compound is:

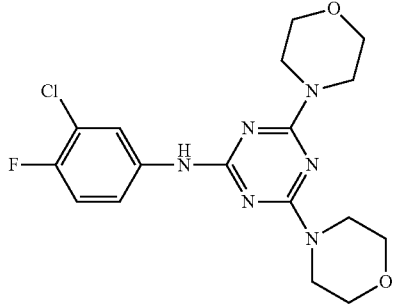

or

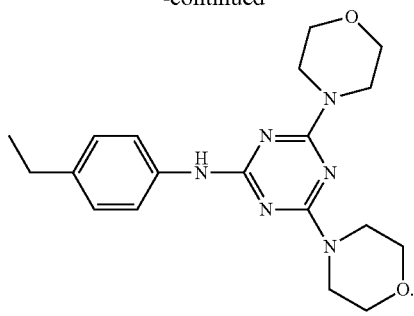

18. The method of embodiment 14 or 15, wherein $R^3$ is $R^4CH=N$—, $R^1$ is H, and $R^2$ is optionally substituted $C_6$-$C_{10}$ aryl.

19. The method of embodiment 18, wherein the compound is:

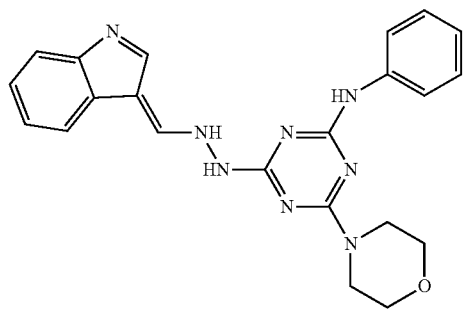

20. The method of embodiment 14, wherein X is CH.

21. The method of embodiment 20, wherein $R^3$ is $R^4CH=N$— and wherein $R^1$ and $R^2$, taken together with the N to which they are attached, form morpholinyl.

22. The method of embodiment 21, wherein the compound is:

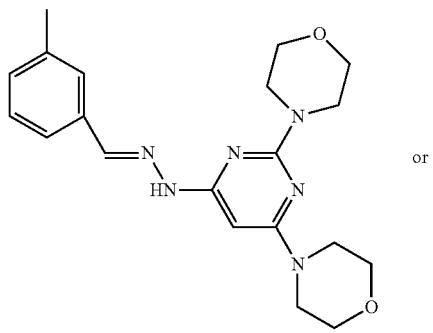

or

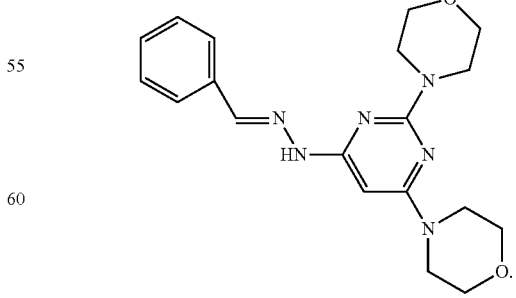

23. The method of any one of embodiments 14-22, wherein the cancer cells are breast cancer cells, malignant melanoma cells, colorectal carcinoma cells, thyroid papillary carcinoma cells, glioma cells, ovarian serous carcinoma cells, lung adenocarcinoma cells, or hairy cell leukemia cells.

24. The method of any one of embodiments 14-23, wherein the cancer cells comprise cells having a BRAF$^{V600E}$ mutation.

25. The method of any one of embodiments 14-24, wherein the method further comprises administering an additional anti-cancer agent to the mammal.

26. A compound of the formula:

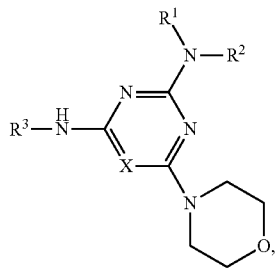

wherein $R^1$ and $R^2$ are independently H, optionally substituted $C_1$-$C_6$ alkyl, or optionally substituted $C_6$-$C_{10}$ aryl, or wherein $R^1$ and $R^2$, taken together with the N to which they are attached, form a 5- or 6-membered heterocyclyl ring, $R^3$ is optionally substituted $C_6$-$C_{10}$ aryl or a group of the formula: $R^4$CH=N— wherein $R^4$ is $C_6$-$C_{10}$ aryl, heteroaryl, or fused bicyclic heteroaryl, X is CH or N, or a tautomer thereof, or a pharmaceutically acceptable salt thereof, for use in treating cancer in a mammal, wherein the cancer is an autophagy-dependent cancer.

27. The compound for use according to embodiment 25, wherein the cancer is breast cancer, malignant melanoma, colorectal carcinoma, thyroid papillary carcinoma, glioma, ovarian serous carcinoma, lung adenocarcinoma, or hairy cell leukemia.

28. A compound of the formula:

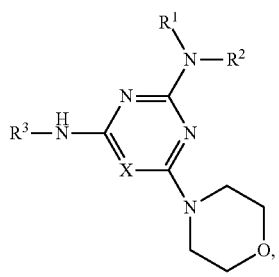

wherein $R^1$ and $R^2$ are independently H, optionally substituted $C_1$-$C_6$ alkyl, or optionally substituted $C_6$-$C_{10}$ aryl, or wherein $R^1$ and $R^2$, taken together with the N to which they are attached, form a 5- or 6-membered heterocyclyl ring, $R^3$ is optionally substituted $C_6$-$C_{10}$ aryl or a group of the formula: $R^4$CH=N— wherein $R^4$ is $C_6$-$C_{10}$ aryl, heteroaryl, or fused bicyclic heteroaryl, X is CH or N, or a tautomer thereof, or a pharmaceutically acceptable salt thereof, for use in selectively killing cancer cells in a patient afflicted with cancer, wherein the cancer cells are autophagy-dependent cancer cells.

29. The compound for use according to embodiment 28, wherein the cancer cells are breast cancer cells, malignant melanoma cells, colorectal carcinoma cells, thyroid papillary carcinoma cells, glioma cells, ovarian serous carcinoma cells, lung adenocarcinoma cells, or hairy cell leukemia cells.

EXAMPLES

The following examples further illustrate the invention but, of course, should not be construed as in any way limiting its scope.

Materials and Methods

Reagents

Compounds 1, 4, 5, 3, and 2 (Specs, ChemDiv, Life Chemicals) and Rapamycin (S1039, Selleck Chemicals) were dissolved in dimethyl sulfoxide (DMSO) at 20 mM concentrations and stored at −20° C. Compound 1 family compounds (FIG. 1) were assayed for purity by high pressure liquid chromatography and their identity confirmed by Mass spectroscopy. Solutions were stable for at least two years. Bafilomycin-A1 (B1793), Chloroquine (C6628), and Hydroxychloroquine (H0915) were purchased from Sigma. Cell-Titer Glo kit used for the assessment of cell viability was purchased from Promega (G7570). N-ethylmaleimide (NEM) was purchased from Sigma-Aldrich (E3876). ONTARGET SMART-pools and non-targeting (nt) control siRNAs against human VPS39 and VPS41 were obtained from GE Dharmacon. siRNA for PIKFYVE (Sc-39142) and PIP4K2C (Sc-29455), as well as transfection reagent (Sc-29528), were purchased from Santa Cruz Biotechnology. Premo Autophagy Sensors LC3-GFP (BacMam 2.0), Tandem Sensor RFP-GFP-LC3B, RFP-p62, LAMP1-RFP, LysoTracker Green DND-26 (L7526), LysoSensor Green DND-189 (L7535), BODIPY FL-pepstatin A (P12271), and Acridine Orange (A3568) were obtained from ThermoFisher.

Cell Culture

Cells were obtained from the American Type Culture Collection. BORCS5-KO HeLa cells have been described previously. Osteosarcoma U2OS were routinely seeded in 6-well plates (0.5×10$^5$ cells/well) and cultured in Dulbecco's Modified Eagle's medium supplemented with L-Glutamine, 4.5 g/L Glucose, Sodium Pyruvate, Phenol Red, and either heat-inactivated or normal 10% fetal calf serum at 37° C. in 5% CO$_2$. Approximately 15-19 hours later, the indicated compound was added in 1:1000 dilutions. Results were the same using either heat-inactivated or normal fetal calf serum. Melanoma A375, embryonic kidney 293T and human foreskin fibroblast Hs27 cells were cultured in the same medium, except that cells were seeded into 12-well plates at 10$^3$ cells/well.

Microscopy

Phase contrast photographs were taken on an Olympus CKX41 microscope. Confocal photographs were taken on a Leica TCS-SP5II. For immunofluorescence microscopy, the cells were fixed in 4% paraformaldehyde (Electron Microscopy Sciences, 15714) in PBS for 12 min, permeabilized with 0.2% Triton X-100 in PBS for 10 min, and blocked in 0.2% BSA (Sigma-Aldrich, A7030) in PBS for 30 min at 37° C. For endogenous LC3 staining, cells were permeabilized in methanol for 20 min at −20° C. after the paraformaldehyde fixation. The cells were sequentially incubated with primary antibodies (LAMP1: Developmental Studies Hybridoma Bank; LC3 and LAMTOR4: Cell Signaling Technology; FLAG epitope: Sigma-Aldrich) and secondary antibodies conjugated to Alexa Fluor dyes (Life Technologies) diluted with 0.2% BSA in PBS for 30 min at 37° C. Coverslips were mounted on glass slides using Fluoromount-G (Electron Microscopy Sciences, 17984-24). Cells were imaged using a Zeiss LSM880 with AiryScan confocal microscope (Carl Zeiss AG, Oberkochen, Germany) or a Leica TCS-SP5II. The final composite images were created and properly analyzed for lysosomal size examination using ImageJ (NIH).

RatioMetric Analysis of Lysosomal pH

To determine the pH of individual lysosomes, dual-wavelength ratio imaging was conducted as previously describe (102), with minor modifications. U2OS and RAW264.7 cells were cultured in imaging chambers (Cellvis, Mountain View Calif., Cat #C4-1.5/h-N) in complete culture medium at 37° C. and 5% $CO_2$. Cells were incubated overnight with 50 µg/mL Oregon Green 488 dextran (Invitrogen, Carlsbad, Calif., D7170). The following day, the cells were cultured with dextran-free complete culture medium for at least 2 h to ensure lysosomal targeting of the probe. Cells were then cultured with compound 1 for the indicated times and concentrations. These results were compared with cells cultured with DMSO at the same volume used to deliver compound 1 (vehicle), and with cells cultured with ammonium chloride to increase the pH of lysosomes (103) (positive control). Confocal micrographs were immediately acquired for each condition, followed by a pH calibration using buffers that span pH4 to pH7. pH calibration buffers were prepared fresh, as previously described (102), filter-sterilized, and then warmed to 37° C. The 488/440 nm ratios of 30-50 lysosomes per condition for each of three independent experiments were used to calculate lysosomal pH values from the calibration curve.

Western Immuno-Blotting Analysis

Total cell lysates were prepared (in 4× dye). Proteins were fractionated at 200V in a NuPAGE 4-12% bis-tris polyacrylamide gel (NP0323, Novex) using NuPAGE MES running buffer (NP0002, Novex) and then stained with PageBlue (24260, Thermo Scientific) in order to quantify the relative amount of histones in each sample. These data were then used to normalize loading of samples for Western immunoblotting analysis. Proteins were wet-transferred onto nitrocellulose membranes (162-0112, Bio-Rad) using NuPAGE transfer buffer (NP-0006-1, Novex) for 1 hour at 30V. Membranes were then stained with dilute Ponceau S solution, blocked in 5% milk for 30 minutes at room temperature, and incubated overnight at 4° C. in primary antibody. Membranes were washed with phosphate buffered saline with tween 20 (PBST) three times for 10 min. each, incubated with secondary antibodies in 5% milk for 1 hour, washed three times with PBST again, covered in ECL (SuperSignal West Pico chemiluminescent substrate, 34080, Thermo Scientific) and exposed to film (HyBlot ES, E3218, Denville Scientific).

Antibody dilutions were: p62 (8025, Cell Signaling Technology) 1:5,000, LC3 I/II (12741, Cell Signaling Technology) 1:5,000, PRPS6 S240/244 (5364, Cell Signaling Technology) 1:20,000, RPS6 (2217, Cell Signaling Technology) 1:20,000, CTSD (2284S, Cell Signaling Technology) 1:1,000, PIKFYVE (MABS522, Millipore), PIP4K2C (SAB1407977, Sigma) 1:10,000, LAMP1 (H4A3, Developmental studies hybridoma bank) 1:5,000, VPS39 (sc-514762, Santa Cruz Biotechnology) 1:1,000, VPS41 (sc-377118, Santa Cruz Biotechnology) 1:1,000, GAPDH (sc-20357, Santa Cruz Biotechnology) 1:1,000, and 3-actin (A5441, Sigma) 1:20,000, HRP-conjugated secondary anti-rabbit (7074, Cell Signalling Technology) 1:10,000 and anti-mouse (A4416, Sigma) 1:10,000.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Mony V K, Benjamin S, O'Rourke E J. A lysosome-centered view of nutrient homeostasis. Autophagy 2016; 12:619-31.
2. Galluzzi L, Bravo-San Pedro J M, Levine B, Green D R, Kroemer G. Pharmacological modulation of autophagy: therapeutic potential and persisting obstacles. Nat Rev Drug Discov 2017; 16:487-511.
3. Yu L, Chen Y, Tooze S A. Autophagy pathway: Cellular and molecular mechanisms. Autophagy 2017:1-9.
4. Hanahan D, Weinberg R A. Hallmarks of cancer: the next generation. Cell 2011; 144:646-74.
5. Gotink K J, Broxterman H J, Labots M, de Haas R R, Dekker H, Honeywell R J, et al. Lysosomal sequestration of sunitinib: a novel mechanism of drug resistance. Clin Cancer Res 2011; 17:7337-46.

6. Levy J M M, Towers C G, Thorburn A. Targeting autophagy in cancer. Nat Rev Cancer 2017; 17:528-42.
7. Mulcahy Levy J M, Zahedi S, Griesinger A M, Morin A, Davies K D, Aisner D L, et al. Autophagy inhibition overcomes multiple mechanisms of resistance to BRAF inhibition in brain tumors. Elife 2017; 6.
8. Cufi S, Vazquez-Martin A, Oliveras-Ferraros C, Corominas-Faja B, Cuyas E, Lopez-Bonet E, et al. The antimalarial chloroquine overcomes primary resistance and restores sensitivity to trastuzumab in HER2-positive breast cancer. Sci Rep 2013; 3:2469.
9. Foley M, Tilley L. Quinoline antimalarials: mechanisms of action and resistance and prospects for new agents. Pharmacol Ther 1998; 79:55-87.
10. Solomon V R, Lee H. Chloroquine and its analogs: a new promise of an old drug for effective and safe cancer therapies. Eur J Pharmacol 2009; 625:220-33.
11. Ma X H, Piao S, Wang D, McAfee Q W, Nathanson K L, Lum J J, et al. Measurements of tumor cell autophagy predict invasiveness, resistance to chemotherapy, and survival in melanoma. Clin Cancer Res 2011; 17:3478-89.
12. Yang S, Wang X, Contino G, Liesa M, Sahin E, Ying H, et al. Pancreatic cancers require autophagy for tumor growth. Genes Dev 2011; 25:717-29.
13. Pellegrini P, Strambi A, Zipoli C, Hagg-Olofsson M, Buoncervello M, Linder S, et al. Acidic extracellular pH neutralizes the autophagy-inhibiting activity of chloroquine: implications for cancer therapies. Autophagy 2014; 10:562-71.
14. Marino M L, Pellegrini P, Di Lernia G, Djavaheri-Mergny M, Brnjic S, Zhang X, et al. Autophagy is a protective mechanism for human melanoma cells under acidic stress. J Biol Chem 2012; 287:30664-76.
15. Piao S, Amaravadi R K. Targeting the lysosome in cancer. Ann N Y Acad Sci 2016; 1371:45-54.
16. Davidson S M, Vander Heiden M G. Critical Functions of the Lysosome in Cancer Biology. Annu Rev Pharmacol Toxicol 2017; 57:481-507.
17. Rebecca V W, Nicastri M C, McLaughlin N, Fennelly C, McAfee Q, Ronghe A, et al. A Unified Approach to Targeting the Lysosome's Degradative and Growth Signaling Roles. Cancer Discov 2017; 7:1266-83.
18. Lee C Y, Johnson R L, Wichterman-Kouznetsova J, Guha R, Ferrer M, Tuzmen P, et al. High-throughput screening for genes that prevent excess DNA replication in human cells and for molecules that inhibit them. Methods 2012; 57:234-48.
19. Zhu W, Lee C Y, Johnson R L, Wichterman J, Huang R, DePamphilis M L. An image-based, high-throughput screening assay for molecules that induce excess DNA replication in human cancer cells. Mol Cancer Res 2011; 9:294-310.
20. Chernomordik L V, Kozlov M M. Protein-lipid interplay in fusion and fission of biological membranes. Annu Rev Biochem 2003; 72:175-207.
21. Jia R, Guardia C M, Pu J, Chen Y, Bonifacino J S. BORC coordinates encounter and fusion of lysosomes with autophagosomes. Autophagy 2017; 13:1648-63.
22. Pu J, Schindler C, Jia R, Jarnik M, Backlund P, Bonifacino J S. BORC, a multisubunit complex that regulates lysosome positioning. Dev Cell 2015; 33:176-88.
23. Niwa S, Tao L, Lu S Y, Liew G M, Feng W, Nachury M V, et al. BORC Regulates the Axonal Transport of Synaptic Vesicle Precursors by Activating ARL-8. Curr Biol 2017; 27:2569-78 e4.
24. Khatter D, Raina V B, Dwivedi D, Sindhwani A, Bahl S, Sharma M. The small GTPase Arl8b regulates assembly of the mammalian HOPS complex on lysosomes. J Cell Sci 2015; 128:1746-61.
25. Pols M S, ten Brink C, Gosavi P, Oorschot V, Klumperman J. The HOPS proteins hVps41 and hVps39 are required for homotypic and heterotypic late endosome fusion. Traffic 2013; 14:219-32.
26. Orr A, Wickner W, Rusin S F, Kettenbach A N, Zick M. Yeast vacuolar HOPS, regulated by its kinase, exploits affinities for acidic lipids and Rab:GTP for membrane binding and to catalyze tethering and fusion. Mol Biol Cell 2015; 26:305-15.
27. Martens S, McMahon H T. Mechanisms of membrane fusion: disparate players and common principles. Nat Rev Mol Cell Biol 2008; 9:543-56.
28. Beckers C J, Block M R, Glick B S, Rothman J E, Balch W E. Vesicular transport between the endoplasmic reticulum and the Golgi stack requires the NEM-sensitive fusion protein. Nature 1989; 339:397-8.
29. Wang T, Li L, Hong W. SNARE proteins in membrane trafficking. Traffic 2017; 18:767-75.
30. Mindell J A. Lysosomal acidification mechanisms. Annu Rev Physiol 2012; 74:69-86.
31. Ho C Y, Choy C H, Wattson C A, Johnson D E, Botelho R J. The Fab1/PIKfyve phosphoinositide phosphate kinase is not necessary to maintain the pH of lysosomes and of the yeast vacuole. J Biol Chem 2015; 290:9919-28.
32. Yapici N B, Bi Y, Li P, Chen X, Yan X, Mandalapu S R, et al. Highly stable and sensitive fluorescent probes (LysoProbes) for lysosomal labeling and tracking. Sci Rep 2015; 5:8576.
33. Maxson M E, Grinstein S. The vacuolar-type H(+)-ATPase at a glance—more than a proton pump. J Cell Sci 2014; 127:4987-93.
34. Chen C S, Chen W N, Zhou M, Arttamangkul S, Haugland R P. Probing the cathepsin D using a BODIPY F L-pepstatin A: applications in fluorescence polarization and microscopy. J Biochem Biophys Methods 2000; 42:137-51.
35. Thome M P, Filippi-Chiela E C, Villodre E S, Migliavaca C B, Onzi G R, Felipe K B, et al. Ratiometric analysis of Acridine Orange staining in the study of acidic organelles and autophagy. J Cell Sci 2016; 129:4622-32.
36. Laurent-Matha V, Derocq D, Prebois C, Katunuma N, Liaudet-Coopman E. Processing of human cathepsin D is independent of its catalytic function and auto-activation: involvement of cathepsins L and B. J Biochem 2006; 139:363-71.
37. Mizushima N, Yamamoto A, Hatano M, Kobayashi Y, Kabeya Y, Suzuki K, et al. Dissection of autophagosome formation using Apg5-deficient mouse embryonic stem cells. J Cell Biol 2001; 152:657-68.
38. Pfeifer U. Inhibition by insulin of the formation of autophagic vacuoles in rat liver. A morphometric approach to the kinetics of intracellular degradation by autophagy. J Cell Biol 1978; 78:152-67.
39. Schworer C M, Shiffer K A, Mortimore G E. Quantitative relationship between autophagy and proteolysis during graded amino acid deprivation in perfused rat liver. J Biol Chem 1981; 256:7652-8.
40. Li Z, Ji X, Wang D, Liu J, Zhang X. Autophagic flux is highly active in early mitosis and differentially regulated throughout the cell cycle. Oncotarget 2016; 7:39705-18.

41. Kimura S, Noda T, Yoshimori T. Dissection of the autophagosome maturation process by a novel reporter protein, tandem fluorescent-tagged LC3. Autophagy 2007; 3:452-60.

42. Ravikumar B, Duden R, Rubinsztein D C. Aggregate-prone proteins with polyglutamine and polyalanine expansions are degraded by autophagy. Hum Mol Genet 2002; 11:1107-17.

43. Sarkar S, Ravikumar B, Floto R A, Rubinsztein D C. Rapamycin and mTOR-independent autophagy inducers ameliorate toxicity of polyglutamine-expanded huntingtin and related proteinopathies. Cell Death Differ 2009; 16:46-56.

44. Mauvezin C, Nagy P, Juhasz G, Neufeld T P. Autophagosome-lysosome fusion is independent of V-ATPase-mediated acidification. Nat Commun 2015; 6:7007.

45. Mauvezin C, Neufeld T P. Bafilomycin A1 disrupts autophagic flux by inhibiting both V-ATPase-dependent acidification and Ca-P60A/SERCA-dependent autophagosome-lysosome fusion. Autophagy 2015; 11:1437-8.

46. Luzio J P, Pryor P R, Bright N A. Lysosomes: fusion and function. Nat Rev Mol Cell Biol 2007; 8:622-32.

47. Compton L M, Ikonomov O C, Sbrissa D, Garg P, Shisheva A. Active vacuolar H+ATPase and functional cycle of Rab5 are required for the vacuolation defect triggered by PtdIns(3,5)P2 loss under PIKfyve or Vps34 deficiency. Am J Physiol Cell Physiol 2016; 311:C366-77.

48. Davis M I, Hunt J P, Herrgard S, Ciceri P, Wodicka L M, Pallares G, et al. Comprehensive analysis of kinase inhibitor selectivity. Nat Biotechnol 2011; 29:1046-51.

49. Ikonomov O C, Sbrissa D, Delvecchio K, Xie Y, Jin J P, Rappolee D, et al. The phosphoinositide kinase PIKfyve is vital in early embryonic development: preimplantation lethality of PIKfyve−/− embryos but normality of PIKfyve+/− mice. J Biol Chem 2011; 286:13404-13.

50. Ikonomov O C, Sbrissa D, Shisheva A. Localized PtdIns 3,5-P2 synthesis to regulate early endosome dynamics and fusion. Am J Physiol Cell Physiol 2006; 291:C393-404.

51. Sbrissa D, Ikonomov O C, Fu Z, Ijuin T, Gruenberg J, Takenawa T, et al. Core protein machinery for mammalian phosphatidylinositol 3,5-bisphosphate synthesis and turnover that regulates the progression of endosomal transport. Novel Sac phosphatase joins the ArPIKfyve-PIKfyve complex. J Biol Chem 2007; 282:23878-91.

52. Shim H, Wu C, Ramsamooj S, Bosch K N, Chen Z, Emerling B M, et al. Deletion of the gene Pip4k2c, a novel phosphatidylinositol kinase, results in hyperactivation of the immune system. Proc Natl Acad Sci USA 2016; 113:7596-601.

53. Mackey A M, Sarkes D A, Bettencourt I, Asara J M, Rameh L E. PIP4kgamma is a substrate for mTORC1 that maintains basal mTORC1 signaling during starvation. Sci Signal 2014; 7:ra104.

54. Al-Ramahi I, Giridharan S S P, Chen Y C, Patnaik S, Safren N, Hasegawa J, et al. Inhibition of PIP4Kgamma ameliorates the pathological effects of mutant huntingtin protein. Elife 2017; 6.

55. Laplante M, Sabatini D M. mTOR signaling at a glance. J Cell Sci 2009; 122:3589-94.

56. Huang S, Houghton P J. Inhibitors of mammalian target of rapamycin as novel antitumor agents: from bench to clinic. Curr Opin Investig Drugs 2002; 3:295-304.

57. Magnuson B, Ekim B, Fingar D C. Regulation and function of ribosomal protein S6 kinase (S6K) within mTOR signalling networks. Biochem J 2012; 441:1-21.

58. Strohecker A M, White E. Targeting mitochondrial metabolism by inhibiting autophagy in BRAF-driven cancers. Cancer Discov 2014; 4:766-72.

59. Goodall M L, Wang T, Martin K R, Kortus M G, Kauffman A L, Trent J M, et al. Development of potent autophagy inhibitors that sensitize oncogenic BRAF V600E mutant melanoma tumor cells to vemurafenib. Autophagy 2014; 10:1120-36.

60. Akan P, Alexeyenko A, Costea P I, Hedberg L, Solnestam B W, Lundin S, et al. Comprehensive analysis of the genome transcriptome and proteome landscapes of three tumor cell lines. Genome Med 2012; 4:86.

61. Ikonomov O C, Sbrissa D, Shisheva A. Mammalian cell morphology and endocytic membrane homeostasis require enzymatically active phosphoinositide 5-kinase PIKfyve. J Biol Chem 2001; 276:26141-7.

62. de Lartigue J, Polson H, Feldman M, Shokat K, Tooze S A, Urbe S, et al. PIKfyve regulation of endosome-linked pathways. Traffic 2009; 10:883-93.

63. Gayle S, Landrette S, Beeharry N, Conrad C, Hernandez M, Beckett P, et al. Identification of apilimod as a first-in-class PIKfyve kinase inhibitor for treatment of B-cell non-Hodgkin lymphoma. Blood 2017; 129:1768-78.

64. Sano O, Kazetani K, Funata M, Fukuda Y, Matsui J, Iwata H. Vacuolin-1 inhibits autophagy by impairing lysosomal maturation via PIKfyve inhibition. FEBS Lett 2016; 590:1576-85.

65. Jefferies H B, Cooke F T, Jat P, Boucheron C, Koizumi T, Hayakawa M, et al. A selective PIKfyve inhibitor blocks PtdIns(3,5)P(2) production and disrupts endomembrane transport and retroviral budding. EMBO Rep 2008; 9:164-70.

66. Cai X, Xu Y, Cheung A K, Tomlinson R C, Alcazar-Roman A, Murphy L, et al. PIKfyve, a class III P I kinase, is the target of the small molecular IL-12/IL-23 inhibitor apilimod and a player in Toll-like receptor signaling. Chem Biol 2013; 20:912-21.

67. Dove S K, Dong K, Kobayashi T, Williams F K, Michell R H. Phosphatidylinositol 3,5-bisphosphate and Fablp/PIKfyve underPPIn endo-lysosome function. Biochem J 2009; 419:1-13.

68. Nicot A S, Laporte J. Endosomal phosphoinositides and human diseases. Traffic 2008; 9:1240-9.

69. Shisheva A. PIKfyve: Partners, significance, debates and paradoxes. Cell Biol Int 2008; 32:591-604.

70. Hessvik N P, Overbye A, Brech A, Torgersen M L, Jakobsen I S, Sandvig K, et al. PIKfyve inhibition increases exosome release and induces secretory autophagy. Cell Mol Life Sci 2016; 73:4717-37.

71. Demirsoy S, Martin S, Motamedi S, van Veen S, Holemans T, Van den Haute C, et al. ATP13A2/PARK9 regulates endo-/lysosomal cargo sorting and proteostasis through a novel PI(3, 5)P2-mediated scaffolding function. Hum Mol Genet 2017; 26:1656-69.

72. Ho C Y, Alghamdi T A, Botelho R J. Phosphatidylinositol-3,5-bisphosphate: no longer the poor PIP2. Traffic 2012; 13:1-8.

73. Jin N, Lang M J, Weisman L S. Phosphatidylinositol 3,5-bisphosphate: regulation of cellular events in space and time. Biochem Soc Trans 2016; 44:177-84.

74. Vicinanza M, Korolchuk V I, Ashkenazi A, Puri C, Menzies F M, Clarke J H, et al. PI(5)P regulates autophagosome biogenesis. Mol Cell 2015; 57:219-34.

75. Hasegawa J, Iwamoto R, Otomo T, Nezu A, Hamasaki M, Yoshimori T. Autophagosome-lysosome fusion in neurons requires INPP5E, a protein associated with Joubert syndrome. EMBO J 2016; 35:1853-67.

76. Hasegawa J, Strunk B S, Weisman L S. PI5P and PI(3,5)P2: Minor, but Essential Phosphoinositides. Cell Struct Funct 2017; 42:49-60.
77. Yu L, McPhee C K, Zheng L, Mardones G A, Rong Y, Peng J, et al. Termination of autophagy and reformation of lysosomes regulated by mTOR. Nature 2010; 465:942-6.
78. Li X, Rydzewski N, Hider A, Zhang X, Yang J, Wang W, et al. A molecular mechanism to regulate lysosome motility for lysosome positioning and tubulation. Nat Cell Biol 2016; 18:404-17.
79. Wartosch L, Gunesdogan U, Graham S C, Luzio J P. Recruitment of VPS33A to HOPS by VPS16 Is Required for Lysosome Fusion with Endosomes and Autophagosomes. Traffic 2015; 16:727-42.
80. Vivona S, Cipriano D J, O'Leary S, Li Y H, Fenn T D, Brunger A T. Disassembly of all SNARE complexes by N-ethylmaleimide-sensitive factor (NSF) is initiated by a conserved 1:1 interaction between alpha-soluble NSF attachment protein (SNAP) and SNARE complex. J Biol Chem 2013; 288:24984-91.
81. Pu J, Guardia C M, Keren-Kaplan T, Bonifacino J S. Mechanisms and functions of lysosome positioning. J Cell Sci 2016; 129:4329-39.
82. Bissig C, Hurbain I, Raposo G, van Niel G. PIKfyve activity regulates reformation of terminal storage lysosomes from endolysosomes. Traffic 2017; 18:747-57.
83. Choy C H, Saffi G, Gray M A, Wallace C, Dayam R M, Ou Z A, et al. Lysosome enlargement during inhibition of the lipid kinase PIKfyve proceeds through lysosome coalescence. J Cell Sci 2018; 131.
84. Lu Y, Dong S, Hao B, Li C, Zhu K, Guo W, et al. Vacuolin-1 potently and reversibly inhibits autophagosome-lysosome fusion by activating RAB5A. Autophagy 2014; 10:1895-905.
85. Martin S, Harper C B, May L M, Coulson E J, Meunier F A, Osborne S L. Inhibition of PIKfyve by YM-201636 dysregulates autophagy and leads to apoptosis-independent neuronal cell death. PLoS One 2013; 8:e60152.
86. Kim G H, Dayam R M, Prashar A, Terebiznik M, Botelho R J. PIKfyve inhibition interferes with phagosome and endosome maturation in macrophages. Traffic 2014; 15:1143-63.
87. Tsuruta F, Dolmetsch R E. PIKfyve mediates the motility of late endosomes and lysosomes in neuronal dendrites. Neurosci Lett 2015; 605:18-23.
88. Baars T L, Petri S, Peters C, Mayer A. Role of the V-ATPase in regulation of the vacuolar fission-fusion equilibrium. Mol Biol Cell 2007; 18:3873-82.
89. Walter C, Clemens L E, Muller A J, Fallier-Becker P, Proikas-Cezanne T, Riess O, et al. Activation of AMPK-induced autophagy ameliorates Huntington disease pathology in vitro. Neuropharmacology 2016; 108:24-38.
90. Deretic V, Saitoh T, Akira S. Autophagy in infection, inflammation and immunity. Nat Rev Immunol 2013; 13:722-37.
91. Kimmelman A C, White E. Autophagy and Tumor Metabolism. Cell Metab 2017; 25:1037-43.
92. Nyfeler B, Eng C H. Revisiting autophagy addiction of tumor cells. Autophagy 2016; 12:1206-7.
93. Mainz L, Rosenfeldt M T. Autophagy and cancer—insights from mouse models. FEBS J 2017.
94. Mowers E E, Sharifi M N, Macleod K F. Autophagy in cancer metastasis. Oncogene 2017; 36:1619-30.
95. Mathew R, Karp C M, Beaudoin B, Vuong N, Chen G, Chen H Y, et al. Autophagy suppresses tumorigenesis through elimination of p62. Cell 2009; 137:1062-75.
96. Degenhardt K, Mathew R, Beaudoin B, Bray K, Anderson D, Chen G, et al. Autophagy promotes tumor cell survival and restricts necrosis, inflammation, and tumorigenesis. Cancer Cell 2006; 10:51-64.
97. Liu X D, Yao J, Tripathi D N, Ding Z, Xu Y, Sun M, et al. Autophagy mediates HIF2alpha degradation and suppresses renal tumorigenesis. Oncogene 2015; 34:2450-60.
98. Karantza-Wadsworth V, Patel S, Kravchuk O, Chen G, Mathew R, Jin S, et al. Autophagy mitigates metabolic stress and genome damage in mammary tumorigenesis. Genes Dev 2007; 21:1621-35.
99. Chude C I, Amaravadi R K. Targeting Autophagy in Cancer: Update on Clinical Trials and Novel Inhibitors. Int J Mol Sci 2017; 18.
100. Rangwala R, Chang Y C, Hu J, Algazy K M, Evans T L, Fecher L A, et al. Combined MTOR and autophagy inhibition: phase I trial of hydroxychloroquine and temsirolimus in patients with advanced solid tumors and melanoma. Autophagy 2014; 10:1391-402.
101. Xie X, Koh J Y, Price S, White E, Mehnert J M. Atg7 Overcomes Senescence and Promotes Growth of BrafV600E-Driven Melanoma. Cancer Discov 2015; 5:410-23.
102. Saric A, Grinstein S, Freeman S A. Measurement of Autolysosomal pH by Dual-Wavelength Ratio Imaging. Methods Enzymol 2017; 588:15-29.
103. Ohkuma S, Poole B. Fluorescence probe measurement of the intralysosomal pH in living cells and the perturbation of pH by various agents. Proc Natl Acad Sci USA 1978; 75:3327-31.
104. Crowley L C, Christensen M E, Waterhouse N J. Measuring Survival of Adherent Cells with the Colony-Forming Assay. Cold Spring Harb Protoc 2016; 2016.

The invention claimed is:
1. A method of (a) treating cancer in a mammal, wherein the cancer is an autophagy-dependent cancer or (b) selectively killing cancer cells in a mammal afflicted with cancer, wherein the cancer cells are autophagy-dependent cancer cells, comprising administering to the mammal an effective amount of a compound selected from:

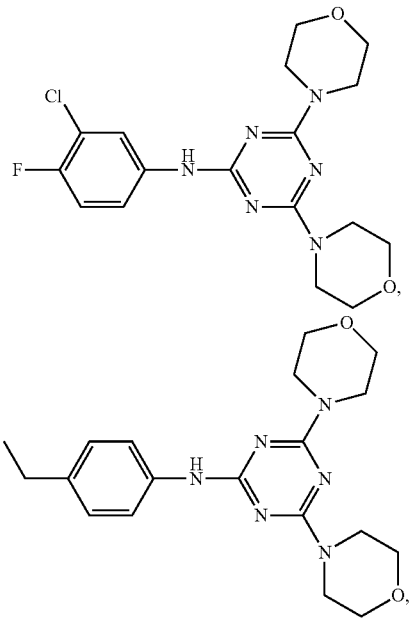

-continued

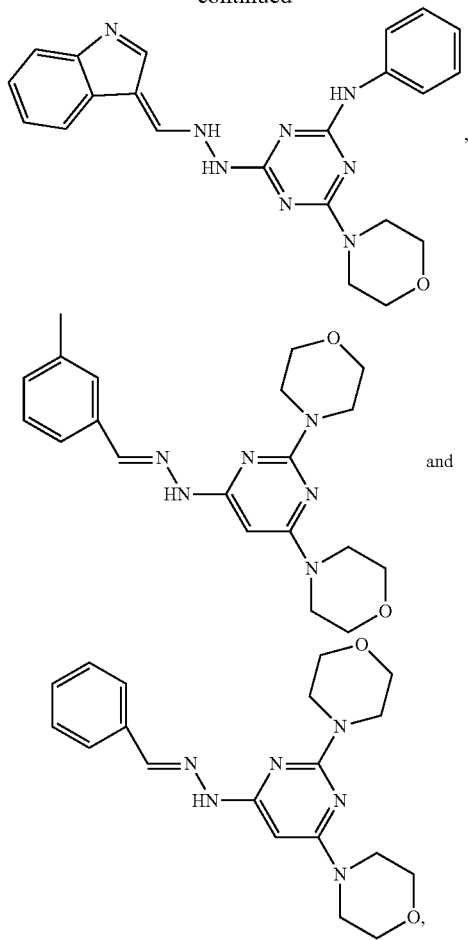

or a pharmaceutically acceptable salt thereof;

wherein the method selectively inhibits PIKFYVE (phosphoinositide kinase FYVE-type zinc finger containing).

2. The method according to claim 1, wherein the cancer is a malignant, metastatic cancer.

3. The method according to claim 2, wherein the cancer is breast cancer, malignant melanoma, colorectal carcinoma, thyroid papillary carcinoma, glioma, ovarian serous carcinoma, lung adenocarcinoma, or hairy cell leukemia.

4. The method according to claim 1, further comprising administering an additional anti-cancer agent to the mammal.

5. The method according to claim 1, wherein the autophagy-dependent cancer is treated and the autophagy-dependent cancer is selected from breast cancer, malignant melanoma, colorectal carcinoma, thyroid papillary carcinoma, glioma, ovarian serous carcinoma, lung adenocarcinoma, and hairy cell leukemia.

6. The method according to claim 5, wherein the cancer comprises cells having a $BRAF^{V600E}$ mutation.

7. The method according to claim 1, wherein the method selectively kills cancer cells in a patient afflicted with cancer, wherein the cancer cells are autophagy-dependent cancer cells selected from breast cancer cells, malignant melanoma cells, colorectal carcinoma cells, thyroid papillary carcinoma cells, glioma cells, ovarian serous carcinoma cells, lung adenocarcinoma cells, and hairy cell leukemia cells.

8. The method according to claim 7, wherein the cancer cells comprise cells having a $BRAF^{V600E}$ mutation.

* * * * *